(12) United States Patent
Danysz et al.

(10) Patent No.: US 7,947,689 B2
(45) Date of Patent: May 24, 2011

(54) SUBSTITUTED PYRAZOLO[1,5-A]PYRIMIDINES AS METABOTROPIC GLUTAMATE RECEPTOR MODULATORS

(75) Inventors: Wojciech Danysz, Nidderau (DE); Andrzej Dekundy, Schoneck (DE); Mirko Hechenberger, Frankfurt (DE); Markus Henrich, Munzenberg (DE); Claudia Jatzke, Frankfurt am Main (DE); Jens Nagel, Daxweiler (DE); Christopher Graham Raphael Parsons, Nidderau (DE); Tanja Weil, Frankfurt am Main (DE); Juris Fotins, Riga (LV); Aleksandrs Gutcaits, Riga (LV); Ivars Kalvinsh, Salaspils (LV); Ronalds Zemribo, Jurmala (LV); Valerjans Kauss, Riga (LV)

(73) Assignee: Merz Pharma GmbH & Co. KGaA, Frankfurt am Main (DE)

( * ) Notice: Subject to any disclaimer, the term of this patent is extended or adjusted under 35 U.S.C. 154(b) by 831 days.

(21) Appl. No.: 11/890,211

(22) Filed: Aug. 3, 2007

(65) Prior Publication Data
US 2008/0039476 A1   Feb. 14, 2008

Related U.S. Application Data

(60) Provisional application No. 60/835,820, filed on Aug. 4, 2006, provisional application No. 60/877,544, filed on Dec. 28, 2006.

(51) Int. Cl.
*C07D 487/04* (2006.01)
*A61K 31/519* (2006.01)
*A61P 25/28* (2006.01)
*A61P 25/02* (2006.01)
*A61P 35/00* (2006.01)
*A61P 25/22* (2006.01)

(52) U.S. Cl. ..................... 514/259.3; 544/281
(58) Field of Classification Search .................. 544/281; 514/259.3
See application file for complete search history.

(56) References Cited

U.S. PATENT DOCUMENTS

| | | | |
|---|---|---|---|
| 5,037,834 | A | 8/1991 | Brighty et al. |
| 6,177,443 | B1 | 1/2001 | Madsen et al. |
| 6,498,251 | B1 | 12/2002 | Kikuchi et al. |
| 6,573,381 | B1 | 6/2003 | Bousquet et al. |
| 2006/0089362 | A1 | 4/2006 | Seno et al. |

FOREIGN PATENT DOCUMENTS

| | | |
|---|---|---|
| WO | 99/26927 | 6/1999 |
| WO | 00/12074 | 3/2000 |
| WO | 02/088088 A1 | 11/2002 |
| WO | 03/037900 A2 | 5/2003 |
| WO | 03/091256 A1 | 11/2003 |
| WO | 03/101993 A1 | 12/2003 |
| WO | 2004/087153 A2 | 10/2004 |
| WO | 2004/089415 A2 | 10/2004 |
| WO | 2004/089416 A2 | 10/2004 |
| WO | 2004/089471 A2 | 10/2004 |
| WO | 2005/121175 A2 | 12/2005 |
| WO | 2006/015737 A1 | 2/2006 |
| WO | 2006/077401 A1 | 7/2006 |

OTHER PUBLICATIONS

Vippagunta, S.R., Adv. Drug. Delivery Rev., 2001, 48, p. 3-26.*
Netterwald, J., Drug Discovery and Dev., 2007, 9(9), p. 22-26.*
G. Hajos, et al., "Product class 5: Azaindolizines with two nitrogen atoms in the five-membered ring" Science of Synthesis, Vo. 109, p. 613-678, 2002.
Laura Bettinetti, "Solution and solid phase supported synthesis of 7a-Azaindoles as novel subtype selective dopamine receptor ligands" Ph. D. Thesis, University of Erlangen, Germanyy 2004.
ChemBridge Corporation: Registry No. 833441-66-0; of Feb. 18, 2005.
DE102004037445, Mar. 16, 2006, Abstract.
International Search Report for PCT/EP2007/058061 of Dec. 3, 2007.
Database CHEMCATS, XP 002460679, Accession No. 2033272150, 2007.

* cited by examiner

*Primary Examiner* — Susanna Moore
(74) *Attorney, Agent, or Firm* — Hueschen and Sage

(57) ABSTRACT

The invention relates to pyrazolopyrimidine derivatives of formula (I)

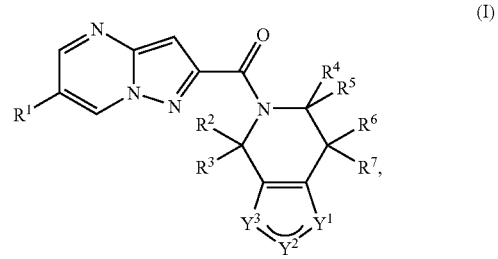

wherein
$Y^1$, $Y^2$ and $Y^3$ independently are e.g. $CR^{10}$, NH, S or O, whereby at least one of $Y^1$, $Y^2$ and $Y^3$ represents $CR^{10}$;
$R^1$ represents chloro or bromo;
$R^2$, $R^3$, $R^4$, $R^5$, $R^6$ and $R^7$ represent e.g. hydrogen or $C_1$-$C_6$-alkyl, and
$R^{10}$ represents e.g. hydrogen, halogen or phenyl;
which are potent mGluR5 modulators and are e.g. useful for the treatment of various neurological disorders.

19 Claims, No Drawings

SUBSTITUTED PYRAZOLO[1,5-A]PYRIMIDINES AS METABOTROPIC GLUTAMATE RECEPTOR MODULATORS

This application claims priority to U.S. Provisional Patent Applications Ser. No. 60/835,820, filed Aug. 4, 2006 and 60/877,544, filed Dec. 28, 2006.

FIELD OF THE INVENTION

The present invention relates to pyrazolopyrimidine derivatives, which can act as novel metabotropic glutamate receptor (mGluR) modulators, methods for their synthesis and their use as a medicament for the treatment of various diseases and/or prevention of disorders, e.g. neurological disorders, by administration of such substances.

BACKGROUND OF THE INVENTION

Neuronal stimuli are transmitted by the central nervous system (CNS) through the interaction of a neurotransmitter released by a neuron, which neurotransmitter has a specific effect on a neuroreceptor of another neuron. L-glutamic acid is considered to be a major excitatory neurotransmitter in the mammalian CNS, consequently playing a critical role in a large number of physiological processes. Glutamate-dependent stimulus receptors are divided into two main groups. The first group comprises ligand-controlled ion channels whereas the other comprises metabotropic glutamate receptors (mGluR). Metabotropic glutamate receptors are a subfamily of G-protein-coupled receptors (GPCR). There is increasing evidence for a peripheral role of both ionotropic and metabotropic glutamate receptors outside the CNS e.g., in chronic pain states.

At present, eight different members of these mGluRs are known. On the basis of structural parameters such as sequence homology, the second messenger system utilized by these receptors and their different affinity to low-molecular weight compounds, these eight receptors can be divided into three groups. MGluR1 and mGluR5 belong to Group I which are positively coupled to phospholipase C and their activation leads to a mobilization of intracellular calcium ions. MGluR2 and mGluR3 belong to Group II and mGluR4, mGluR6, mGluR7 and mGluR8 belong to Group III, both of which are negatively coupled to adenylyl cyclase, i.e., their activation causes a reduction in second messenger cAMP and thus a dampening of neuronal activity.

The mGluR5 modulators have been shown to modulate the effects of the presynaptically released neurotransmitter glutamate via postsynaptic mechanisms. Moreover, as these modulators can be both positive and/or negative mGluR5 modulators, such modulators may increase or inhibit the effects mediated through these metabotropic glutamate receptors.

Of particular interest are those modulators which are negative mGluR5 modulators. Such modulators decrease the effects mediated through metabotropic glutamate receptors. Since a variety of patho-physiological processes and disease states affecting the CNS are thought to be related to abnormal glutamate neurotransmission, and mGluR5 receptors are shown to be expressed in several areas of the CNS, modulators of these receptors could be therapeutically beneficial in the treatment of CNS diseases.

Therefore, mGluR5 positive or negative modulators may be administered to provide neuroprotection and/or disease modification in the following acute or chronic pathological conditions or to provide a symptomatological effect on the following conditions:

Alzheimer's disease, Creutzfeld-Jakob's syndrome/disease, bovine spongiform encephalopathy (BSE), prion related infections, diseases involving mitochondrial dysfunction, diseases involving β-amyloid and/or tauopathy, Down's syndrome, hepatic encephalopathy, Huntington's disease, motor neuron diseases, amyotrophic lateral sclerosis (ALS), olivoponto-cerebellar atrophy, post-operative cognitive deficit (POCD), systemic lupus erythematosus, systemic sclerosis, Sjogren's syndrome, Neuronal Ceroid Lipofuscinosis, neurodegenerative cerebellar ataxias, Parkinson's disease, Parkinson's dementia, mild cognitive impairment, cognitive deficits in various forms of mild cognitive impairment, cognitive deficits in various forms of dementia, dementia pugilistica, vascular and frontal lobe dementia, cognitive impairment, learning impairment, eye injuries, eye diseases, eye disorders, glaucoma, retinopathy, macular degeneration, head or brain or spinal cord injuries, head or brain or spinal cord trauma, trauma, hypoglycaemia, hypoxia, perinatal hypoxia, ischaemia, ischaemia resulting from cardiac arrest or stroke or bypass operations or transplants, convulsions, epileptic convulsions, epilepsy, temporal lobe epilepsy, myoclonic epilepsy, inner ear insult, inner ear insult in tinnitus, tinnitus, sound- or drug-induced inner ear insult, sound- or drug-induced tinnitus, L-dopa-induced dykinesias, L-dopa-induced dykinesias in Parkinson's disease therapy, dyskinesias, dyskinesia in Huntington's disease, drug induced dyskinesias, neuroleptic-induced dyskinesias, haloperidol-induced dyskinesias, dopaminomimetic-induced dyskinesias, chorea, Huntington's chorea, athetosis, dystonia, stereotypy, ballism, tardive dyskinesias, tic disorder, torticollis spasmodicus, blepharospasm, focal and generalized dystonia, nystagmus, hereditary cerebellar ataxias, corticobasal degeneration, tremor, essential tremor, abuse, addiction, nicotine addiction, nicotine abuse, alcohol addiction, alcohol abuse, opiate addiction, opiate abuse, cocaine addiction, cocaine abuse, amphetamine addiction, amphetamine abuse, anxiety disorders, panic disorders, anxiety and panic disorders, social anxiety disorder (SAD), attention deficit hyperactivity disorder (ADHD), attention deficit syndrome (ADS), restless leg syndrome (RLS), hyperactivity in children, autism, dementia, dementia in Alzheimer's disease, dementia in Korsakoff syndrome, Korsakoff syndrome, vascular dementia, dementia related to HIV infections, HIV-1 encephalopathy, AIDS encephalopathy, AIDS dementia complex, AIDS-related dementia, major depressive disorder, major depression, depression, depression resulting from Borna virus infection, major depression resulting from Borna virus infection, bipolar manic-depressive disorder, drug tolerance, drug tolerance to opioids, movement disorders, fragile-X syndrome, irritable bowel syndrome (IBS), migraine, multiple sclerosis (MS), muscle spasms, pain, chronic pain, acute pain, inflammatory pain, neuropathic pain, diabetic neuropathic pain (DNP), pain related to rheumatic arthritis, allodynia, hyperalgesia, nociceptive pain, cancer pain, post-traumatic stress disorder (PTSD), schizophrenia, positive or cognitive or negative symptoms of schizophrenia, spasticity, Tourette's syndrome, urinary incontinence, vomiting, pruritic conditions, pruritis, sleep disorders, micturition disorders, neuromuscular disorder in the lower urinary tract, gastroesophageal reflux disease (GERD), gastrointestinal dysfunction, lower esophageal sphincter (LES) disease, functional gastrointestinal disorders, dyspepsia, regurgitation, respiratory tract infection, bulimia nervosa, chronic laryngitis, asthma, reflux-related asthma, lung disease, eating disorders, obesity, obesity-related disorders, obesity abuse, food addiction, binge eating disorders, agoraphobia, generalized anxiety disorder, obsessive-compulsive disorder, panic disorder, posttraumatic stress disorder, social phobia, phobic disorders, substance-induced anxiety disorder, delusional disorder, schizoaffective disorder, schizophreniform disorder, substance-induced psychotic disorder, or delirium.

The mGluR5 negative or positive modulators may also be administered to provide inhibition of tumour cell growth, migration, invasion, adhesion and toxicity in the peripheral tissues, peripheral nervous system and CNS. MGluR5 modulators may be administered to provide therapeutic intervention in neoplasia, hyperplasia, dysplasia, cancer, carcinoma, sarcoma, oral cancer, squamous cell carcinoma (SCC), oral squamous cell carcinoma (SCC), lung cancer, lung adenocarcinoma, breast cancer, prostate cancer, gastric cancer, liver cancer, colon cancer, colorectal carcinoma, rhabdomyosarcoma, brain tumour, tumour of a nerve tissue, glioma, malignant glioma, astroglioma, neuroglioma, neuroblastoma, glioblastoma, medulloblastoma, cancer of skin cells, melanoma, malignant melanoma, epithelial neoplasm, lymphoma, myeloma, Hodgkin's disease, Burkitt's lymphoma, leukemia, thymoma, and other tumours.

Further indications for mGluR5 negative or positive modulators include those indications wherein a particular condition does not necessarily exist but wherein a particular physiological parameter may be improved through administration of the instant compounds, for example cognitive enhancement, learning impairment and/or neuroprotection.

Positive modulators may be particularly useful in the treatment of positive and negative symptoms in schizophrenia and cognitive deficits in various forms of dementia and mild cognitive impairment.

In the literature, several types of modulators of mGluR5 have already been described.

Furthermore, several types of pyrazolopyrimidine compounds have been disclosed in the prior art.

Various methods for preparing substituted pyrazolopyrimidine derivatives are known, e.g. from G. Hajos and Z. Riedl, Science of Synthesis 109, 613-678 (2002) and from Laura Bettinetti (Ph. D. Thesis, University of Erlangen, Germany, 2004).

In WO 2004/087153 various pyrazolopyrimidines of formula (XXII) are described, which can act as small molecule immune potentiators (SMIP) and which can be used e.g. for cancer treatment.

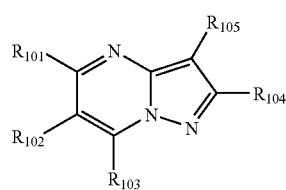

(XXII)

Furthermore, in WO 2004/089471, the use of substituted pyrazolo[1,5-a]pyrimidines or prodrugs or salts thereof are described for the preparation of a pharmaceutical composition for the treatment of disorders and diseases where it is desirable to modulate the activity of the enzyme 11βHSD1 or to inhibit 11βHSD1. In the document WO 2004/089471, pyrazolo(1,5-a)pyrimidine derivates of the following general formula (C) are disclosed:

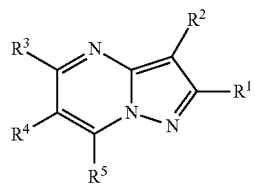

(c)

In WO 2003/037900, further specific pyrazolopyrimidine compounds are described as inhibitors of ion-channels in human cells. In this document compounds having the following general formula (X) are described:

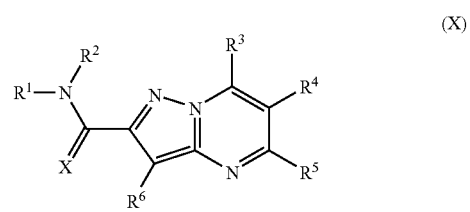

(X)

wherein
R$^1$ is e.g. alkyl; R$^2$ is a e.g. hydrogen or alkyl; or
R$^1$ and R$^2$ taken together with the nitrogen atom to which they are optionally joined to form a 4- to 8-membered heterocycloaryl ring;
R$^3$ is e.g. hydrogen, alkyl, halo, amino or aryl;
R$^4$ is e.g. hydrogen, halo, alkyl or aryl; and
R$^5$ is a member selected from substituted or unsubstituted alkyl, substituted or unsubstituted aryl, substituted or unsubstituted heteroaryl and substituted or unsubstituted heterocycloalkyl; R$^6$ is e.g. hydrogen, halo or aryl; and
X is a member selected from O and S.

Several pyrazolopyrimidine compounds according to the present invention, however have been tested which are found to be not significantly active as inhibitors of ion-channels in human cells. In this document WO 2003/037900, compounds of the following two structures are mentioned as example compounds (B308) and (B310), which however have shown no particular activity as metabotropic glutamate receptor (mGluR5) modulators:

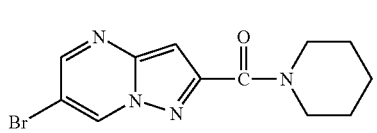

(B308)

(6-Bromopyrazolo[1,5-a]pyrimidin-2-yl)-piperidin-1-yl-methanone

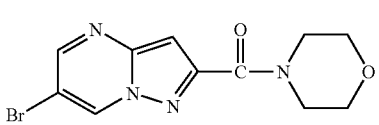

(B310)

(6-Bromopyrazolo[1,5-a]pyrimidin-2-yl)-morpholin-4-yl-methanone.

In WO 2003/101993 several types of pyrazolopyrimidine compounds and their use for the treatment of hepatitis infections are disclosed. WO 2003/101993 deals with compounds of the following general formula (Z)

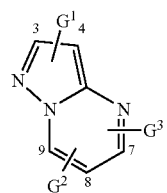

(Z)

wherein:
$G^1$ is selected e.g. from the group of —OH, cyano, —C(O)—OH, —C(O)—NR$^2$R$^3$, where R$^2$ and R$^3$ taken together from a 5- or 6-membered heteroaromatic or saturated or partially unsaturated heterocyclic ring, or
$G^2$ is independently are selected from the group consisting e.g. of alkyl, cycloalkyl, aryl, heteroaryl, saturated or partially unsaturated heterocyclic radical, trifluoromethyl,
$G^3$ can be absent or is independently selected from the group consisting of e.g. alkyl, cycloalkyl, aryl, heteroaryl, saturated or partially unsaturated heterocyclic radical,
$G^2$ and $G^3$, collectively, are attached at any two of positions C7, C8 and C9 of the pyrimidine ring, the remaining position being optionally substituted with alkyl, alkenyl, alkynyl, halo, fluoroalkyl, hydroxyl, alkoxy, or cyano;
wherein the ring portion of any of said cycloalkyl, aryl, aralkyl, heteroaryl, heteroarylalkyl, or heterocyclic radical in $G^1$, $G^2$ or $G^3$ can be optionally substituted.

In the document WO 2003/091256 particular pyrazolopyrimidine derivatives which have a NADPH-oxidase inhibitor activity are described. The compounds have the following general formula (Y)

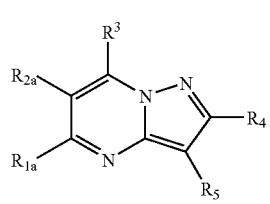

(Y)

wherein $R_{1a}$, $R_{2a}$, $R_3$-$R_5$ represent hydrogen, halogen, lower alkyl that may be substituted, lower alkenyl that may be substituted, lower alkynyl that may be substituted, cycloalkyl that may be substituted, cycloalkenyl that may be substituted, cycloalkynyl that may be substituted, aryl that may be substituted, heterocyclic group that may be substituted, hydroxyl, alkoxy that may be substituted, aryloxy that may be substituted, heterocyclic oxy that may be substituted, acyl that may be substituted, monosubstituted carbonyloxy that may be substituted, carbamoyl that may be substituted, diazo, amidino that may be substituted, azido, nitroso, nitro, amino that may be substituted, imino that may be substituted, cyano, mercapto, monosubstituted sulfinyl that may be substituted, monosubstituted sulfonyl that may be substituted, sulfo, or trisubstituted silyl, and any combinations of $R_{1a}$, $R_{2a}$, $R_3$-$R_5$ may together form a ring structure.

A further pyrazolopyrimidine compound which has already been described in the literature (see ChemBridge Corporation; Registry Nr. 833441-66-0; of Feb. 18, 2005), has the following structure (M):

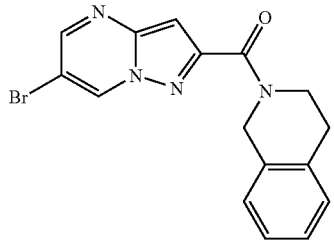

(M)

(6-Bromo-pyrazolo[1,5-a]pyrimidin-2-yl)-(1,2,3,4-tetrahydro-isoquinolin-2-yl)-methanon.

This compound, however has only a limited activity as metabotropic glutamate receptor (mGluR5) modulator and furthermore is not selective.

In WO 2006/015737 further heterocyclic compounds which can contain a carboxylic acid amid function are disclosed which have an activity at dopamine receptors and which can be used for the treatment of CNS-diseases. As one example structure, pyrazolopyrimidines are mentioned.

In WO 2002/088088 the synthesis of tetrahydro-isoquinolin compounds is disclosed which can serve as intermediates for the synthesis of pharmaceutically active compounds.

THE PRESENT INVENTION

It now has been found that certain pyrazolopyrimidine derivatives which differ in structure from the known pyrazolopyrimidines, are potent mGluR5 modulators. Therefore, these substances may be therapeutically beneficial in the treatment of conditions which involve abnormal glutamate neurotransmission or in which modulation of mGluR5 receptors results in therapeutic benefit. These substances are preferably administered in the form of a pharmaceutical composition, wherein they are present together with one or more pharmaceutically acceptable diluents, carriers, or excipients.

OBJECTS OF THE INVENTION

It is an object of the present invention to provide novel pharmaceutical compounds which are mGluR5 modulators and pharmaceutical compositions thereof. It is a further object of the invention to provide a novel method of treating, eliminating, alleviating, palliating, or ameliorating undesirable CNS disorders which involve, abnormal glutamate neurotransmission by employing a compound of the invention or a pharmaceutical composition containing the same.

An additional object of the invention is the provision of processes for producing the pyrazolopyrimidine derivatives.

SUMMARY OF THE INVENTION

The invention in general deals with:
A compound selected from those of formula (Ig)

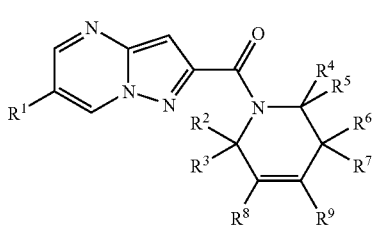

(Ig)

wherein
$R^1$ represents chloro or bromo;
$R^2$, $R^3$, $R^4$, $R^5$, $R^6$ and $R^7$, which may be the same or different, each independently represent hydrogen, $C_{1-6}$alkyl, amino, hydroxy, halogen, or trifluoromethyl;

$R^8$ represents hydrogen, or $C_{1-6}$alkyl;

$R^9$ represents aryl or heteroaryl, wherein the aryl or heteroaryl group may be optionally substituted by one or more substituents (e.g., 1, 2, or 3), which may be the same or different, selected independently from halogen, amino, hydroxy, nitro, cyano, trifluoromethyl, trifluoromethoxy, aminocarbonyl, N—$C_{1-6}$alkylaminocarbonyl, di-N,N—$C_{1-6}$alkylaminocarbonyl, $C_{1-6}$alkyl, hydroxy$C_{1-6}$alkyl, $C_{2-6}$alkenyl, $C_{1-6}$alkoxy, $C_{1-6}$alkoxycarbonyl, $C_{1-6}$alkylcarbonyloxy, $C_{1-6}$alkylamino, di-$C_{1-6}$alkylamino, $C_{1-6}$alkylcarbonylamino, $C_{1-6}$alkylenedioxy, aryl, heteroaryl, heterocyclyl, and cyclo$C_{3-12}$alkyl;

or $R^8$ and $R^9$ together with the carbon atoms to which they are attached may form an unsaturated cyclic ring system containing 5 to 7 (i.e. 5, 6 or 7) carbon atoms, wherein 0 to 4 (i.e. 0, 1, 2, 3 or 4) of the carbon atoms of the ring system formed by $R^8$ and $R^9$ may be replaced by heteroatoms independently selected from nitrogen, oxygen and sulfur and wherein the ring system may be optionally substituted by one or more (e.g., 1, 2, or 3) substituents, which may be the same or different, independently selected from halogen, amino, hydroxy, nitro, cyano, trifluoromethyl, trifluoromethoxy, aminocarbonyl, N—$C_{1-6}$alkylaminocarbonyl, di-N,N—$C_{1-6}$alkylaminocarbonyl, $C_{1-6}$alkyl, hydroxy$C_{1-6}$alkyl, $C_{2-6}$alkenyl, $C_{1-6}$alkoxy, $C_{1-6}$alkoxycarbonyl, $C_{1-6}$alkylcarbonyloxy, $C_{1-6}$alkylamino, di-$C_{1-6}$alkylamino, $C_{1-6}$alkylcarbonylamino, $C_{1-6}$alkylenedioxy, aryl, heteroaryl, heterocyclyl, and cyclo$C_{3-12}$alkyl;

and optical isomers, pharmaceutically acceptable salts, hydrates, solvates, and polymorphs thereof; it being understood that: the compound of Formula Ig does not represent: (6-Bromo-pyrazolo[1,5-a]pyrimidin-2-yl)-(3,4-dihydro-1H-isoquinolin-2-yl)-methanone.

Furthermore, a compound of Formula (Ig), wherein $R^8$ represents hydrogen or methyl;

$R^1$ represents chloro or bromo;

$R^2$, $R^3$, $R^4$, $R^5$, $R^6$ and $R^7$, which may be the same or different, each independently represent hydrogen, $C_{1-6}$alkyl, amino, hydroxy, halogen, or trifluoromethyl;

$R^9$ represents aryl or heteroaryl, wherein the aryl or heteroaryl group may be optionally substituted by one or more substituents (e.g., 1, 2, or 3), which may be the same or different, selected independently from halogen, amino, hydroxy, nitro, cyano, trifluoromethyl, trifluoromethoxy, aminocarbonyl, N—$C_{1-6}$alkylaminocarbonyl, di-N,N—$C_{1-6}$alkylaminocarbonyl, $C_{1-6}$alkyl, hydroxy$C_{1-6}$alkyl, $C_{2-6}$alkenyl, $C_{1-6}$alkoxy, $C_{1-6}$alkoxycarbonyl, $C_{1-6}$alkylcarbonyloxy, $C_{1-6}$alkylamino, di-$C_{1-6}$alkylamino, $C_{1-6}$alkylcarbonylamino, $C_{1-6}$alkylenedioxy, aryl, heteroaryl, heterocyclyl, and cyclo$C_{3-12}$alkyl;

or $R^8$ and $R^9$ together with the carbon atoms to which they are attached may form an unsaturated cyclic ring system containing 5 to 7 (i.e. 5, 6 or 7) carbon atoms, wherein 0 to 4 (i.e. 0, 1, 2, 3 or 4) of the carbon atoms of the ring system formed by $R^8$ and $R^9$ may be replaced by heteroatoms independently selected from nitrogen, oxygen and sulfur and wherein the ring system may be optionally substituted by one or more (e.g., 1, 2, or 3) substituents, which may be the same or different, independently selected from halogen, amino, hydroxy, nitro, cyano, trifluoromethyl, trifluoromethoxy, aminocarbonyl, N—$C_{1-6}$alkylaminocarbonyl, di-N,N—$C_{1-6}$alkylaminocarbonyl, $C_{1-6}$alkyl, hydroxy$C_{1-6}$alkyl, $C_{2-6}$alkenyl, $C_{1-6}$alkoxy, $C_{1-6}$alkoxycarbonyl, $C_{1-6}$alkylcarbonyloxy, $C_{1-6}$alkylamino, di-$C_{1-6}$alkylamino, $C_{1-6}$alkylcarbonylamino, $C_{1-6}$alkylenedioxy, aryl, heteroaryl, heterocyclyl, and cyclo$C_{3-12}$alkyl.

Such a compound of Formula (Ig), wherein $R^9$ represents phenyl or monocyclic heteroaryl, wherein the heteroaryl ring contains from 1 to 4 (i.e. 1, 2, 3 or 4) heteroatoms selected independently from oxygen, sulfur and nitrogen and wherein the phenyl or heteroaryl ring may be optionally substituted by one to three substituents, which may be the same or different, selected independently from halogen, amino, hydroxy, nitro, cyano, trifluoromethyl, trifluoromethoxy, aminocarbonyl, N—$C_{1-6}$alkylaminocarbonyl, di-N,N—$C_{1-6}$alkylaminocarbonyl, $C_{1-6}$alkyl, hydroxy$C_{1-6}$alkyl, $C_{2-6}$alkenyl, $C_{1-6}$alkoxy, $C_{1-6}$alkoxycarbonyl, $C_{1-6}$alkylcarbonyloxy, $C_{1-6}$alkylamino, di-$C_{1-6}$alkylamino, $C_{1-6}$alkylcarbonylamino, $C_{1-6}$alkylenedioxy, aryl, heteroaryl, heterocyclyl, and cyclo$C_{3-12}$alkyl;

$R^1$ represents chloro or bromo;

$R^2$, $R^3$, $R^4$, $R^5$, $R^6$ and $R^7$, which may be the same or different, each independently represent hydrogen, $C_{1-6}$alkyl, amino, hydroxy, halogen, or trifluoromethyl; and $R^8$ represents hydrogen, or methyl.

Such a compound of Formula (Ig), wherein $R^8$ represents hydrogen;

$R^9$ represents phenyl, optionally substituted by one to two substituents, which may be the same or different, selected independently from halogen, amino, hydroxy, nitro, cyano, trifluoromethyl, trifluoromethoxy, aminocarbonyl, N—$C_{1-6}$alkylaminocarbonyl, di-N,N—$C_{1-6}$alkylaminocarbonyl, $C_{1-6}$alkyl, $C_{1-6}$alkoxy, $C_{1-6}$alkylcarbonyloxy, and $C_{1-6}$alkylcarbonylamino;

$R^1$ represents chloro or bromo; and $R^2$, $R^3$, $R^4$, $R^5$, $R^6$ and $R^7$, which may be the same or different, each independently represent hydrogen, $C_{1-6}$alkyl, amino, hydroxy, halogen, or trifluoromethyl.

Such a compound of Formula (Ig), wherein $R^8$ represents hydrogen;

$R^9$ represents phenyl, optionally substituted by one to two substituents, which may be the same or different, selected independently from halogen, amino, hydroxy, nitro, cyano, trifluoromethyl, trifluoromethoxy, aminocarbonyl, N—$C_{1-6}$alkylaminocarbonyl, di-N,N—$C_{1-6}$alkylaminocarbonyl, $C_{1-6}$alkyl, $C_{1-6}$alkoxy, $C_{1-6}$alkylcarbonyloxy, and $C_{1-6}$alkylcarbonylamino;

$R^1$ represents chloro or bromo;

$R^2$, $R^3$, $R^4$ and $R^5$, which may be the same or different, each independently represent hydrogen or methyl; and $R^6$ and $R^7$ represent hydrogen.

Such a compound of Formula (Ig), wherein $R^8$ represents hydrogen;

$R^9$ represents phenyl, optionally substituted by one to two substituents, which may be the same or different, selected independently from halogen, amino, hydroxy, nitro, cyano, trifluoromethyl, trifluoromethoxy, aminocarbonyl, N—$C_{1-6}$alkylaminocarbonyl, di-N,N—$C_{1-6}$alkylaminocarbonyl, $C_{1-6}$alkyl, $C_{1-6}$alkoxy, $C_{1-6}$alkylcarbonyloxy, and $C_6$alkylcarbonylamino;

$R^1$ represents chloro or bromo;

$R^6$ and $R^7$ represent hydrogen; and one of $R^2$, $R^3$, $R^4$ and $R^5$ represents methyl and the remaining of $R^2$, $R^3$, $R^4$ and $R^5$ represent hydrogen.

Such a compound of Formula (Ig), wherein $R^8$ and $R^9$ together with the carbon atoms to which they are attached form an unsaturated cyclic ring system containing 6 carbon atoms, wherein 0 to 2 (i.e. 0, 1 or 2) of the carbon atoms of the ring system formed by $R^8$ and $R^9$, may be replaced by a heteroatom independently selected from nitrogen, oxygen and sulfur and wherein the ring system may be optionally substituted by one or more (e.g., 1, 2, or 3) substituents, which may be the same or different, independently selected from halogen, amino, hydroxy, nitro, cyano, trifluoromethyl, trifluoromethoxy, aminocarbonyl, N—$C_{1-6}$alkylaminocarbonyl, di-N,N—$C_{1-6}$alkylaminocarbonyl, $C_{1-6}$alkyl, hydroxy$C_{1-6}$alkyl, $C_{2-6}$alkenyl, $C_{1-6}$alkoxy, $C_{1-6}$alkoxycarbonyl, $C_{1-6}$alkylcarbonyloxy, $C_{1-6}$alkylamino, di-$C_{1-6}$alkylamino, $C_{1-6}$alkylcarbonylamino, $C_{1-6}$alkylenedioxy, aryl, heteroaryl, heterocyclyl, and cyclo-$C_{3-12}$alkyl;

$R^1$ represents chloro or bromo; and $R^2$, $R^3$, $R^4$, $R^5$, $R^6$ and $R^7$, which may be the same or different, each independently represent hydrogen, $C_{1-6}$alkyl, amino, hydroxy, halogen, or trifluoromethyl.

Such compound of Formula (Ig), wherein $R^8$ and $R^9$ together with the carbon atoms to which they are attached form a benzene ring system optionally substituted by one to two substituents, which may be the same or different, independently selected from halogen, amino, hydroxy, nitro, cyano, trifluoromethyl, trifluoromethoxy, aminocarbonyl, N—$C_{1-6}$alkylaminocarbonyl, di-N,N—$C_{1-6}$alkylaminocarbonyl, $C_{1-6}$alkyl, $C_{1-6}$alkoxy, $C_{1-6}$alkylcarbonyloxy and $C_{1-6}$alkylcarbonylamino;

$R^1$ represents chloro or bromo; and $R^2$, $R^3$, $R^4$, $R^5$, $R^6$ and $R^7$, which may be the same or different, each independently represent hydrogen, $C_{1-6}$alkyl, amino, hydroxy, halogen, or trifluoromethyl.

Such compound of Formula (Ig), wherein $R^8$ and $R^9$ together with the carbon atoms to which they are attached form a benzene ring system optionally substituted by one to two substituents, which may be the same or different, independently selected from halogen, amino, hydroxy, nitro, cyano, trifluoromethyl, trifluoromethoxy, aminocarbonyl, N—$C_{1-6}$alkylaminocarbonyl, di-N,N—$C_{1-6}$alkylaminocarbonyl, $C_{1-6}$alkyl, $C_{1-6}$alkoxy, $C_{1-6}$alkylcarbonyloxy and $C_{1-6}$alkylcarbonylamino;

$R^1$ represents chloro or bromo;

$R^2$, $R^3$, $R^4$ and $R^5$, which may be the same or different, independently represent hydrogen or methyl; and $R^6$ and $R^7$ represent hydrogen.

Furthermore, a compound of Formula (Ig), wherein $R^8$ and $R^9$ together with the carbon atoms to which they are attached form a benzene ring system optionally substituted by one to two substituents, which may be the same or different, independently selected from halogen, amino, hydroxy, nitro, cyano, trifluoromethyl, trifluoromethoxy, aminocarbonyl, N—$C_{1-6}$alkylaminocarbonyl, di-N,N—$C_{1-6}$alkylaminocarbonyl, $C_{1-6}$alkyl, $C_{1-6}$alkoxy, $C_{1-6}$alkylcarbonyloxy and $C_{1-6}$alkylcarbonylamino;

$R^1$ represents chloro or bromo;

$R^2$, $R^3$, $R^4$ and $R^5$, which may be the same or different, independently represent hydrogen or ethyl or trifluoromethyl; and $R^6$ and $R^7$ represent hydrogen.

Such compound of Formula (Ig), wherein $R^8$ and $R^9$ together with the carbon atoms to which they are attached form a benzene ring system optionally substituted by one to two substituents, which may be the same or different, independently selected from halogen, amino, hydroxy, nitro, cyano, trifluoromethyl, trifluoromethoxy, aminocarbonyl, N—$C_{1-6}$alkylaminocarbonyl, di-N,N—$C_{1-6}$alkylaminocarbonyl, $C_{1-6}$alkyl, $C_{1-6}$alkoxy, $C_{1-6}$alkylcarbonyloxy and $C_{1-6}$alkylcarbonylamino;

$R^1$ represents chloro or bromo;

$R^6$ and $R^7$ represent hydrogen; and one of $R^2$ and $R^3$ represents methyl and the remaining of $R^2$ and $R^3$, and $R^4$ and $R^5$, represent hydrogen.

Furthermore, a compound of Formula (Ig), wherein $R^8$ and $R^9$ together with the carbon atoms to which they are attached form a benzene ring system optionally substituted by one to two substituents, which may be the same or different, independently selected from halogen, amino, hydroxy, nitro, cyano, trifluoromethyl, trifluoromethoxy, aminocarbonyl, N—$C_{1-6}$alkylaminocarbonyl, di-N,N—$C_{1-6}$alkylaminocarbonyl, $C_{1-6}$alkyl, $C_{1-6}$alkoxy, $C_{1-6}$alkylcarbonyloxy and $C_{1-6}$alkylcarbonylamino;

$R^1$ represents chloro or bromo;

$R^6$ and $R^7$ represent hydrogen; and one of $R^2$ and $R^3$ represents ethyl or trifluoromethyl and the remaining of $R^2$ and $R^3$, and $R^4$ and $R^5$, represent hydrogen.

Such a compound of Formula (Ig), wherein $R^8$ and $R^9$ together with the carbon atoms to which they are attached form an unsaturated cyclic ring system containing 5 carbon atoms, wherein 0 to 3 (i.e. 0, 1, 2 or 3) of the carbon atoms of the ring formed by $R^8$ and $R^9$ may be replaced by a heteroatom independently selected from nitrogen, oxygen and sulfur and wherein the ring system may be optionally substituted by one to two substituents, which may be the same or different, independently selected from halogen, amino, hydroxy, nitro, cyano, trifluoromethyl, trifluoromethoxy, aminocarbonyl, N—$C_{1-6}$alkylaminocarbonyl, di-N,N—$C_{1-6}$alkylaminocarbonyl, $C_{1-6}$alkyl, hydroxy$C_{1-6}$alkyl, $C_{2-6}$alkenyl, $C_{1-6}$alkoxy, $C_{1-6}$alkoxycarbonyl, $C_{1-6}$alkylcarbonyloxy, $C_{1-6}$alkylamino, di-$C_{1-6}$alkylamino, $C_{1-6}$alkylcarbonylamino, $C_{1-6}$alkylenedioxy, aryl, heteroaryl, heterocyclyl, and cyclo$C_{3-12}$alkyl;

$R^1$ represents chloro or bromo; and $R^2$, $R^3$, $R^4$, $R^5$, $R^6$ and $R^7$, which may be the same or different, each independently represent hydrogen, $C_{1-6}$alkyl, amino, hydroxy, halogen, or trifluoromethyl.

Such a compound of Formula (Ig), which is selected from those of Formula (IgA),

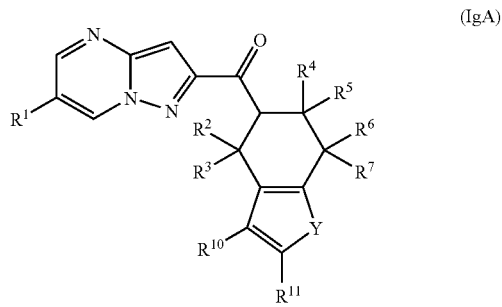

(IgA)

wherein

Y represents NH, S, or O;

$R^{10}$ and $R^{11}$, which may be the same or different, each independently represent hydrogen, halogen, amino, hydroxy, nitro, cyano, trifluoromethyl, trifluoromethoxy, aminocarbonyl, N—$C_{1-6}$alkylaminocarbonyl, di-N,N—$C_{1-6}$alkylaminocarbonyl, $C_{1-6}$alkyl, $C_{1-6}$alkoxy, $C_{1-6}$alkylcarbonyloxy, or $C_{1-6}$alkylcarbonylamino;

$R^1$ represents chloro or bromo; and $R^2$, $R^3$, $R^4$, $R^5$, $R^6$ and $R^7$, which may be the same or different, each independently represent hydrogen, $C_{1-6}$alkyl, amino, hydroxy, halogen, or trifluoromethyl.

Such a compound of Formula (IgA), wherein Y represents NH, S, or O;

$R^{10}$ and $R^{11}$, which may be the same or different, each independently represent hydrogen, halogen, amino, hydroxy, nitro, cyano, trifluoromethyl, trifluoromethoxy, aminocarbonyl, N—$C_{1-6}$alkylaminocarbonyl, di-N,N—$C_{1-6}$alkylaminocarbonyl, $C_{1-6}$alkyl, $C_{1-6}$alkoxy, $C_{1-6}$alkylcarbonyloxy, or $C_{1-6}$alkylcarbonylamino;

$R^1$ represents chloro or bromo;

$R^2$, $R^3$, $R^4$ and $R^5$, which may be the same or different, independently represent hydrogen or methyl; and $R^6$ and $R^7$ represent hydrogen.

Such a compound of Formula (IgA), wherein Y represents NH, S, or O;

$R^{10}$ and $R^{11}$, which may be the same or different, each independently represent hydrogen, halogen, amino, hydroxy, nitro, cyano, trifluoromethyl, trifluoromethoxy, aminocarbonyl, N—$C_{1-6}$alkylaminocarbonyl, di-N,N—$C_{1-6}$alkylaminocarbonyl, $C_{1-6}$alkyl, $C_{1-6}$alkoxy, $C_{1-6}$alkylcarbonyloxy, or $C_{1-6}$alkylcarbonylamino;

$R^1$ represents chloro or bromo;

$R^6$ and $R^7$ represent hydrogen; and one of $R^2$ and $R^3$ represents methyl and the remaining of $R^2$ and $R^3$, and $R^4$ and $R^5$, represent hydrogen.

Furthermore, a compound selected from those of Formula (Ig)

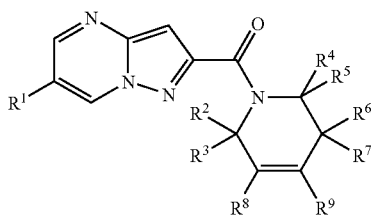

(Ig)

wherein $R^1$ represents chloro or bromo;

$R^2$, $R^3$, $R^4$, $R^5$, $R^6$ and $R^7$, which may be the same or different, each independently represent hydrogen, $C_{1-6}$alkyl, amino, hydroxy, halogen, or trifluoromethyl;

$R^8$ represents hydrogen, or $C_{1-6}$alkyl;

$R^9$ represents aryl or heteroaryl, wherein the aryl or heteroaryl group may be optionally substituted by one or more substituents (e.g., 1, 2, or 3), which may be the same or different, selected independently from halogen, amino, hydroxy, nitro, cyano, trifluoromethyl, trifluoromethoxy, aminocarbonyl, N—$C_{1-6}$alkylaminocarbonyl, di-N,N—$C_{1-6}$alkylaminocarbonyl, $C_{1-6}$alkyl, hydroxy$C_{1-6}$alkyl, $C_{2-6}$alkenyl, $C_{1-6}$alkoxy, $C_{1-6}$alkoxycarbonyl, $C_{1-6}$alkylcarbonyloxy, $C_{1-6}$alkylamino, di-$C_{1-6}$alkylamino, $C_{1-6}$alkylcarbonylamino, $C_{1-6}$alkylenedioxy, aryl, heteroaryl, heterocyclyl, and cyclo$C_{3-12}$alkyl;

or $R^8$ and $R^9$ together with the carbon atoms to which they are attached may form an unsaturated cyclic ring system containing 5 to 7 (i.e. 5, 6 or 7) carbon atoms, wherein 0 to 4 (i.e. 0, 1, 2, 3 or 4) of the carbon atoms of the ring system formed by $R^8$ and $R^9$ may be replaced by heteroatoms independently selected from nitrogen, oxygen and sulfur and wherein the ring system may be optionally substituted by one or more (e.g., 1, 2, or 3) substituents, which may be the same or different, independently selected from halogen, amino, hydroxy, nitro, cyano, trifluoromethyl, trifluoromethoxy, aminocarbonyl, N—$C_{1-6}$alkylaminocarbonyl, di-N,N—$C_{1-6}$alkylaminocarbonyl, $C_{1-6}$alkyl, hydroxy$C_{1-6}$alkyl, $C_{2-6}$alkenyl, $C_{1-6}$alkoxy, $C_{1-6}$alkoxycarbonyl, $C_{1-6}$alkylcarbonyloxy, $C_{1-6}$alkylamino, di-$C_{1-6}$alkylamino, $C_{1-6}$alkylcarbonylamino, $C_{1-6}$alkylenedioxy, aryl, heteroaryl, heterocyclyl, and cyclo$C_{3-12}$alkyl;

or an optical isomer, pharmaceutically acceptable salt, hydrate, solvate, or polymorph thereof for use as a medicament.

In the compounds of the invention $R^1$ defined by Formula (Ig) and Formula (IgA) may represent bromo. Alternatively, $R^1$ defined by Formula (Ig) and Formula (IgA) may represent chloro. It will be apparent to those skilled in the art that the invention also includes optical isomers, pharmaceutically acceptable salts, hydrates, solvates, and polymorphs of the described compounds.

Moreover the invention deals with a pharmaceutical composition comprising, together with one or more pharmaceutically acceptable excipients or vehicles, at least one compound of formula (Ig) or of formula (IgA), wherein the substituents are as defined above, or optical isomers, pharmaceutically acceptable salts, hydrates, solvates, and polymorphs thereof.

Moreover, a method for treating or preventing a condition or disease associated with abnormal glutamate neurotransmission or a method for modulating mGluR5 receptors to achieve therapeutic benefit, or a method for enhancing cognition, such method comprising the step of administering to a living animal, including a human, a therapeutically effective amount of a compound selected of those of formula (Ig) or formula (IgA).

Furthermore, the preparation of and the uses of a compound of formula (Ig) or formula (IgA) or optical isomers, pharmaceutically acceptable salts, hydrates, solvates, and polymorphs thereof or the manufacturing or preparation of a medicament are part of the invention.

The invention in particular relates to a compound selected from those of formula (I)

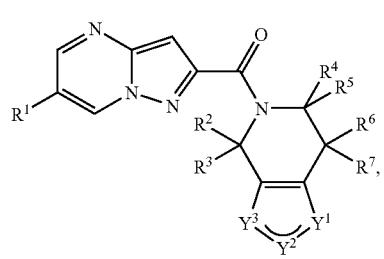

(I)

wherein:

$Y^1$, $Y^2$ and $Y^3$ independently represent $CR^{10}$, $CR^{11}$, $CR^{10}R^{11}$, $NR^{12}$, S or O, whereby at least one of $Y^1$, $Y^2$ and $Y^3$ represents $CR^{10}$;

or $Y^1$ and $Y^2$ together represent a group $R^{10}C=N$; $R^{10}C=CR^{11}$; $R^{10}R^{11}C—C(=O)$ or $R^{12}N—(C=O)$;

or $Y^2$ and $Y^3$ together represent a group $R^{10}C=N$; $R^{10}C=CR^{11}$; $R^{10}R^{11}C—C(=O)$ or $R^{12}N—(C=O)$;

$R^1$ represents chloro or bromo;

$R^2$ represents hydrogen, $C_{1-6}$alkyl, $C_{3-7}$cycloalkyl or trifluoromethyl;

$R^3$ represents hydrogen, $C_{1-6}$alkyl, $C_{3-7}$cycloalkyl or trifluoromethyl; or $R^2$ and $R^3$ together with the carbon atom of the ring represent a carbonyl group;

$R^4$ represents hydrogen, $C_{1-6}$alkyl, $C_{3-7}$cycloalkyl or trifluoromethyl;

$R^5$ represents hydrogen, $C_{1-6}$alkyl, $C_{3-7}$cycloalkyl or trifluoromethyl; or $R^4$ and $R^5$ together with the carbon atom of the ring represent a carbonyl group;

$R^6$ represents hydrogen, $C_{1-6}$alkyl, $C_{3-7}$cycloalkyl or trifluoromethyl;

$R^7$ represents hydrogen, $C_{1-6}$alkyl, $C_{3-7}$cycloalkyl or trifluoromethyl;

$R^6$ and $R^7$ together with the carbon atom of the ring represent a carbonyl group;

$R^2$ or $R^3$ together with $R^6$ or $R^7$ may form a bivalent radical of type $CH_2—CH_2$ or $CH_2—O$;

$R^{10}$ and $R^{11}$ independently represent hydrogen, halogen, amino, hydroxy, nitro, cyano, trifluoromethyl, trifluoromethoxy, aryl, $C_{1-6}$alkyl, $C_{3-7}$cycloalkyl, $C_{2-6}$alkenyl, $C_{2-6}$alkynyl, $C_{1-6}$alkoxy, $C_{3-7}$-cycloalkyloxy, $C_{2-6}$alkenyloxy, $C_{2-6}$alkynyloxy, heteroaryl, heterocyclyl, aryloxy, heteroaryloxy, heterocyclyloxy, $C_{1-6}$alkylamino, di-$C_{1-6}$alkylamino, $C_{3-7}$-cycloalkylamino, di-$C_{3-7}$-cycloalkylamino, $C_{1-6}$alkyl-$C_{3-7}$-cycloalkylamino, $C_{2-6}$alkenylamino, $C_{2-6}$alkynylamino, di-$C_{2-6}$alkenylamino, di-$C_{2-6}$alkynylamino, $C_{1-6}$alkyl-$C_{2-6}$-alkenylamino, $C_{1-6}$alkyl-$C_{2-6}$-alkynylamino, $C_{2-6}$alkenyl-$C_{3-7}$-cycloalkylamino, $C_{2-6}$alkynyl-$C_{3-7}$-cycloalkylamino, $C_{2-6}$alkenyl-$C_{2-6}$-alkynylamino arylamino, diarylamino, aryl-$C_{1-6}$alkylamino, aryl-$C_{2-6}$alkenylamino, aryl-$C_{2-6}$alkynylamino, aryl-$C_{3-7}$-cycloalkylamino, heteroarylamino, diheteroarylamino, heteroaryl-$C_{1-6}$alkylamino, heteroaryl-$C_{2-6}$alkenylamino, heteroaryl-$C_{2-6}$alkynylamino, heteroaryl-$C_{3-7}$-cycloalkylamino, heteroarylarylamino, heterocyclylamino, diheterocyclylamino, heterocyclyl-$C_{1-6}$alkylamino, heterocyclyl-$C_{2-6}$alkenylamino, heterocyclyl-$C_{2-6}$alkynylamino, heterocyclyl-$C_{3-7}$-cycloalkylamino, heterocyclylarylamino, heterocyclylhetero-arylamino, acyl, acyloxy, acylamino, $C_{1-6}$alkoxycarbonyl, $C_{3-7}$-cycloalkoxy-carbonyl, $C_{2-6}$alkenyloxycarbonyl, $C_{2-6}$alkynyloxycarbonyl, aryloxycarbonyl, heteroaryloxycarbonyl, heterocyclyloxycarbonyl, aminocarbonyl, $C_{1-6}$alkylamino-carbonyl, di-$C_{1-6}$alkylaminocarbonyl, $C_{3-7}$-cycloalkylaminocarbonyl, di-$C_{3-7}$-cycloalkylaminocarbonyl, $C_{1-6}$alkyl-$C_{3-7}$-cycloalkylaminocarbonyl, $C_{2-6}$alkenyl-aminocarbonyl, $C_{2-6}$alkynylaminocarbonyl, di-$C_{2-6}$alkenylaminocarbonyl, di-$C_{2-6}$alkynylaminocarbonyl, $C_{1-6}$alkyl-$C_{2-6}$-alkenylaminocarbonyl, $C_{1-6}$alkyl-$C_{2-6}$-alkynyl-aminocarbonyl, $C_{2-6}$alkenyl-$C_{3-7}$-cycloalkylaminocarbonyl, $C_{2-6}$alkynyl-$C_{3-7}$-cycloalkylaminocarbonyl, $C_{2-6}$alkenyl-$C_{2-6}$-alkynylaminocarbonyl, arylaminocarbonyl, diarylaminocarbonyl, aryl-$C_{1-6}$alkylaminocarbonyl, aryl-$C_{2-6}$alkenylaminocarbonyl, aryl-$C_{2-6}$alkynylaminocarbonyl, aryl-$C_{3-7}$-cycloalkylaminocarbonyl heteroarylaminocarbonyl, diheteroarylaminocarbonyl, heteroaryl-$C_{1-6}$alkylaminocarbonyl, heteroaryl-$C_{2-6}$alkenylaminocarbonyl, heteroaryl-$C_{2-6}$alkynylaminocarbonyl, heteroaryl-$C_{3-7}$-cycloalkylaminocarbonyl, heteroarylarylaminocarbonyl, heterocyclylaminocarbonyl, diheterocyclylaminocarbonyl, heterocyclyl-$C_{1-6}$alkylaminocarbonyl, heterocyclyl-$C_{2-6}$alkenylamino-carbonyl, heterocyclyl-$C_{2-6}$alkynylaminocarbonyl, heterocyclyl-$C_{3-7}$-cycloalkylaminocarbonyl, heterocyclylarylaminocarbonyl, heterocyclylheteroarylamino-carbonyl, $C_{1-6}$alkylsulfinyl, $C_{3-7}$-cycloalkylsulfinyl, $C_{2-6}$alkenylsulfinyl, $C_{2-6}$alkynylsulfinyl, arylsulfinyl, heteroarylsulfinyl, heterocyclylsulfinyl, $C_{1-6}$alkylsulfonyl, $C_{3-7}$-cycloalkylsulfonyl, $C_{2-6}$alkenylsulfonyl, $C_{2-6}$alkynylsulfonyl, arylsulfonyl, heteroarylsulfonyl, heterocyclylsulfonyl, $C_{1-6}$alkylsulfonylamino, or arylsulfonylamino; and $R^{12}$ represents hydrogen, $C_{1-6}$alkyl, $C_{3-7}$cycloalkyl, $C_{2-6}$alkenyl, $C_{2-6}$alkynyl, acyl, aryl, heteroaryl, heterocyclyl, $C_{1-6}$alkylamino-carbonyl, di-$C_{1-6}$alkylaminocarbonyl, $C_{1-6}$alkylsulfonyl, arylsulfonyl or heteroarylsulfonyl;

and optical isomers, pharmaceutically acceptable salts, hydrates, solvates, and polymorphs thereof.

Such a compound of formula (I), wherein $Y^2$ represents $CR^{10}$ and $Y^3$ represents $CR^{11}$ or wherein $Y^2$ and $Y^3$ together represent a group $R^{10}C=CR^{11}$.

Such a compound of formula (I) wherein $Y^2$ and $Y^3$ together represent a group $R^{10}C=CR^{11}$ and wherein $Y^1$ represents a group $CR^{11}$, $NR^{12}$, S or O (including pyrazolopyrimidines compounds in which the amino-part of the molecule have a dihydrothieno(3,2-c)pyridin-ring system or a dihydro-4H-furo(3,2-c)pyridin-system).

Such a compound of formula (I), wherein one of the groups $Y^1$, $Y^2$ and $Y^3$ represents a group $CR^{10}$ and one of the groups $Y^1$, $Y^2$ and $Y^3$ represents a group $CR^{11}$ wherein one of the two radicals $R^{10}$ and $R^{11}$ represents hydrogen and the other represents a group from halogen, amino, hydroxy, nitro, cyano, trifluoromethyl, trifluoromethoxy, phenyl, $C_{1-6}$alkyl and $C_{1-6}$alkoxy.

Such a compound of formula (I), wherein $R^1$ represents chloro or bromo;

$R^2$ represents hydrogen, $C_{1-6}$alkyl, $C_{3-7}$cycloalkyl or trifluoromethyl;

$R^3$ represents hydrogen, $C_{1-6}$alkyl, $C_{3-7}$cycloalkyl or trifluoromethyl;

$R^4$ represents hydrogen, $C_{1-6}$alkyl, $C_{3-7}$cycloalkyl or trifluoromethyl;

$R^5$ represents hydrogen, $C_{1-6}$alkyl, $C_{3-7}$cycloalkyl or trifluoromethyl;

$R^6$ represents hydrogen, $C_{1-6}$alkyl, $C_{3-7}$cycloalkyl or trifluoromethyl; and $R^7$ represents hydrogen, $C_{1-6}$alkyl, $C_{3-7}$cycloalkyl or trifluoromethyl.

Such a compound of formula (I), wherein $R^1$ represents chloro or bromo;

$R^2$ represents hydrogen, $C_6$alkyl or trifluoromethyl;

$R^3$ represents hydrogen, $C_{1-6}$alkyl or trifluoromethyl;

$R^4$ represents hydrogen, $C_{1-6}$alkyl or trifluoromethyl;

$R^5$ represents hydrogen, $C_{1-6}$alkyl or trifluoromethyl;

$R^6$ represents hydrogen, $C_{1-6}$alkyl or trifluoromethyl; and $R^7$ represents hydrogen, $C_{1-6}$alkyl or trifluoromethyl.

Such a compound of formula (I), wherein $R^{10}$ and $R^{11}$ independently represent the following groups: hydrogen, halogen, amino, hydroxy, nitro, cyano, trifluoromethyl, trifluoromethoxy, aryl, $C_{1-6}$alkyl, $C_{3-7}$-cycloalkyl, $C_{2-6}$alkenyl, $C_{2-6}$alkynyl, $C_{1-6}$alkoxy, $C_{3-7}$-cycloalkyloxy, $C_{2-6}$alkenyloxy, $C_{2-6}$alkynyloxy, heteroaryl, heterocyclyl, aryloxy, heteroaryloxy, heterocyclyloxy, $C_{1-6}$alkylamino, di-$C_{1-6}$alkylamino, $C_{3-7}$-cycloalkylamino, $C_{1-6}$alkyl-$C_{3-7}$-cycloalkylamino, $C_{2-6}$alkenylamino, $C_{2-6}$alkynylamino, aryl-$C_{1-6}$alkylamino, heteroarylamino, heteroaryl-$C_{1-6}$alkylamino, heterocyclylamino, heterocyclyl-$C_{1-6}$alkylamino, acyl, acyloxy, acylamino, $C_{1-6}$alkoxycarbonyl, $C_{3-7}$-cycloalkoxy-carbonyl, heterocyclyloxycarbonyl, aminocarbonyl, $C_{1-6}$alkylamino-carbonyl, di-$C_{1-6}$alkylaminocarbonyl, $C_{3-7}$-cycloalkylaminocarbonyl, arylaminocarbonyl, aryl-$C_{1-6}$alkylaminocarbonyl, aryl-$C_{2-6}$alkynylaminocarbonyl, heteroarylaminocarbonyl, heterocyclylaminocarbonyl, heterocyclyl-$C_{1-6}$alkylaminocarbonyl, alkylsulfinyl, alkylsulfonyl, $C_{1-6}$-alkylsulfonylamino and arylsulfonylamino.

Such a compound of formula (I), wherein $R^{12}$ represents hydrogen, methyl, ethyl, acyl, aryl, heteroaryl, heterocyclyl, $C_{1-6}$alkylamino-carbonyl or di-$C_{1-6}$alkylamino-carbonyl.

Such a compound of formula (I), wherein $R^2$, $R^3$, $R^4$ and $R^5$ independently represent hydrogen, methyl, ethyl or trifluoromethyl; and $R^6$ and $R^7$ represent hydrogen or methyl.

Such a compound of formula (I), wherein $R^2$, $R^3$, $R^4$, $R^5$, $R^6$ and $R^7$ independently represent hydrogen, methyl or ethyl.

Such a compound of formula (I), wherein $R^2$ and $R^3$ independently represent hydrogen, methyl or ethyl.

Such a compound of formula (I), wherein $R^2$ represents methyl or ethyl and $R^3$ represents hydrogen and which has at least one chiral carbon atom. These compounds can be prepared as racemic mixtures or as specific enantiomeric compounds. The compounds having one chiral atom only can be isolated as R-configured isomers or as S-configured isomers, which often do not have the same activity. The compounds having two or more chiral atoms can be prepared as mixtures of isomers or can be prepared as single stereoisomeric compound.

Such a compound of formula (I), wherein one of the groups $Y^2$ and $Y^3$ represents a group $CR^{10}$ and one of the groups $Y^2$ and $Y^3$ represents a group $CR^{11}$ wherein $R^{10}$ and $R^{11}$ are independently selected from hydrogen, methyl, fluoro, bromo, tri-fluoro-methyl and phenyl, and wherein $Y^1$ represents a group $CR^{11}$, NH, S or O. Moreover, such a compound of formula (I), wherein $Y^1$ represents O or S.

Such a compound of formula (I), wherein $R^1$ represents chloro. Moreover, such a compound of formula (I) wherein $R^1$ represents bromo.

Such a compound of formula (I) wherein $Y^1$ represents O, S or $NR^{12}$. Moreover, such a compound wherein $Y^1$ represents O, S or NH.

Such a compound of formula (I) wherein $Y^1$ represents O or S, and $Y^2$ and $Y^3$ together represent a group $R^{10}C=CR^{11}$ or $R^{10}C=N$.

Such a compound of formula (I) wherein $Y^1$ represents O or S, and $Y^2$ and $Y^3$ together represent a group $R^{10}C=CR^{11}$ wherein $R^{10}$ and $R^{11}$ often are both hydrogen.

Such a compound of formula (I) wherein $R^2$, $R^3$, $R^4$ and $R^5$ independently represent hydrogen, methyl, ethyl or trifluoromethyl; $R^6$ and $R^7$ represent hydrogen or methyl and $R^{10}$ and $R^{11}$ independently are selected from hydrogen, methyl, fluoro, bromo, trifluoromethyl or phenyl.

The invention includes compounds of formula (I) selected from the following compounds (or salts thereof):

(6-Bromo-pyrazolo[1,5-a]pyrimidin-2-yl)-(4-methyl-6,7-dihydro-4H-thieno[3,2-c]pyridin-5-yl)-methanone (6-Chloro-pyrazolo[1,5-a]pyrimidin-2-yl)-(4-methyl-6,7-dihydro-4H-thieno[3,2-c]pyridin-5-yl)-methanone (6-Chloro-pyrazolo[1,5-a]pyrimidin-2-yl)-(6,7-dihydro-4H-thieno[3,2-c]pyridin-5-yl)-methanone (6-Bromo-pyrazolo[1,5-a]pyrimidin-2-yl)-(6,7-dihydro-4H-thieno[3,2-c]pyridin-5-yl)-methanone (6-Chloro-pyrazolo[1,5-a]pyrimidin-2-yl)-(4,4-dimethyl-6,7-dihydro-4H-thieno[3,2-c]pyridin-5-yl)-methanone (6-Bromo-pyrazolo[1,5-a]pyrimidin-2-yl)-(4,4-dimethyl-6,7-dihydro-4H-thieno[3,2-c]pyridin-5-yl)-methanone (6-Chloro-pyrazolo[1,5-a]pyrimidin-2-yl)-(6-methyl-6,7-dihydro-4H-thieno[3,2-]pyridin-5-yl)-methanone (6-Bromo-pyrazolo[1,5-a]pyrimidin-2-yl)-(6-methyl-6,7-dihydro-4H-thieno[3,2-]pyridin-5-yl)-methanone (6-Bromo-pyrazolo[1,5-a]pyrimidin-2-yl)-(4-ethyl-6,7-dihydro-4H-thieno[3,2-c]pyridin-5-yl)-methanone (6-Chloro-pyrazolo[1,5-a]pyrimidin-2-yl)-(4-ethyl-6,7-dihydro-4H-thieno[3,2-c]pyridin-5-yl)-methanone (6-Bromo-pyrazolo[1,5-a]pyrimidin-2-yl)-(4-trifluoromethyl-6,7-dihydro-4H-thieno[3,2-c]pyridin-5-yl)-methanone (6-Chloro-pyrazolo[1,5-a]pyrimidin-2-yl)-(4-trifluoromethyl-6,7-dihydro-4H-thieno[3,2-c]pyridin-5-yl)-methanone 6-Bromo-pyrazolo[1,5-a]pyrimidin-2-yl)-(6,6-dimethyl-6,7-dihydro-4H-thieno[3,2-c]pyridin-5-yl)-methanone 6-Chloro-pyrazolo[1,5-a]pyrimidin-2-yl)-(6,6-dimethyl-6,7-dihydro-4H-thieno[3,2-c]pyridin-5-yl)-methanone (6-Bromo-pyrazolo[1,5-a]pyrimidin-2-yl)-(2,4-dimethyl-6,7-dihydro-4H-thieno[3,2-c]pyridin-5-yl)-methanone (6-Chloro-pyrazolo[1,5-a]pyrimidin-2-yl)-(2,4-dimethyl-6,7-dihydro-4H-thieno[3,2-c]pyridin-5-yl)-methanone (6-Bromo-pyrazolo[1,5-a]pyrimidin-2-yl)-(3,4-dimethyl-6,7-dihydro-4H-thieno[3,2-c]pyridin-5-yl)-methanone (6-Bromo-pyrazolo[1,5-a]pyrimidin-2-yl)-(2,3,4-trimethyl-6,7-dihydro-4H-thieno[3,2-c]pyridin-5-yl)-methanone (6-Chloro-pyrazolo[1,5-a]pyrimidin-2-yl)-(2,3,4-trimethyl-6,7-dihydro-4H-thieno[3,2-c]pyridin-5-yl)-methanone (6-Bromo-pyrazolo[1,5-a]pyrimidin-2-yl)-(2-fluoro-4-methyl-6,7-dihydro-4H-thieno[3,2-c]pyridin-5-yl)-methanone (6-Chloro-pyrazolo[1,5-a]pyrimidin-2-yl)-(2-fluoro-4-methyl-6,7-dihydro-4H-thieno[3,2-c]pyridin-5-yl)-methanone (6-Bromo-pyrazolo[1,5-a]pyrimidin-2-yl)-(3-fluoro-4-methyl-6,7-dihydro-4H-thieno[3,2-c]pyridin-5-yl)-methanone (6-Chloro-pyrazolo[1,5-a]pyrimidin-2-yl)-(3-fluoro-4-methyl-6,7-dihydro-4H-thieno[3,2-c]pyridin-5-yl)-methanone (6-Bromo-pyrazolo[1,5-a]pyrimidin-2-yl)-(2,3-difluoro-4-methyl-6,7-dihydro-4H-thieno[3,2-c]pyridin-5-yl)-methanone (6-Chloro-pyrazolo[1,5-a]pyrimidin-2-yl)-(2,3-difluoro-4-methyl-6,7-dihydro-4H-thieno[3,2-c]pyridin-5-yl)-methanone (6-Bromo-pyrazolo[1,5-a]pyrimidin-2-yl)-(4-methyl-2-trifluoromethyl-6,7-dihydro-4H-thieno[3,2-c]pyridin-5-yl)-methanone (6-Chloro-pyrazolo[1,5-a]pyrimidin-2-yl)-(4-methyl-2-trifluoromethyl-6,7-dihydro-4H-thieno[3,2-c]pyridin-5-yl)-methanone (6-Bromo-pyrazolo[1,5-a]pyrimidin-2-yl)-(4-methyl-6,7-dihydro-4H-furo[3,2-c]pyridin-5-yl)-methanone (6-Chloro-pyrazolo[1,5-a]pyrimidin-2-yl)-(4-methyl-6,7-dihydro-4H-furo[3,2-c]pyridin-5-yl)-methanone (6-Chloro-pyrazolo[1,5-a]pyrimidin-2-yl)-(6,7-dihydro-4H-furo[3,2-c]pyridin-5-yl)-methanone (6-Bromo-pyrazolo[1,5-a]pyrimidin-2-yl)-(6,7-dihydro-4H-furo[3,2-c]pyridin-5-yl)-methanone (6-Bromo-pyrazolo[1,5-a]pyrimidin-2-yl)-(6-methyl-6,7-dihydro-4H-furo[3,2-c]pyridin-5-yl)-methanone (6-Chloro-pyrazolo[1,5-a]pyrimidin-2-yl)-(6-methyl-6,7-dihydro-4H-furo[3,2-c]pyridin-5-yl)-methanone
(6-Chloro-pyrazolo[1,5-a]pyrimidin-2-yl)-(2,4-dimethyl-6,7-dihydro-4H-furo[3,2-c]pyridin-5-yl)-methanone
(6-Bromo-pyrazolo[1,5-a]pyrimidin-2-yl)-(2,4-dimethyl-6,7-dihydro-4H-furo[3,2-c]pyridin-5-yl)-methanone
(6-Bromo-pyrazolo[1,5-a]pyrimidin-2-yl)-(1,4,6,7-tetrahydro-pyrrolo[3,2-c]pyridin-5-yl)-methanone
(6-Chloro-pyrazolo[1,5-a]pyrimidin-2-yl)-(1,4,6,7-tetrahydro-pyrrolo[3,2-c]pyridin-5-yl)-methanone
(6-Chloro-pyrazolo[1,5-a]pyrimidin-2-yl)-(4-methyl-1,4,6,7-tetrahydro-pyrrolo[3,2-c]pyridin-5-yl)-methanone
(6-Bromo-pyrazolo[1,5-a]pyrimidin-2-yl)-(4-methyl-1,4,6,7-tetrahydro-pyrrolo[3,2-c]pyridin-5-yl)-methanone
(6-Bromo-pyrazolo[1,5-a]pyrimidin-2-yl)-(8-methyl-5,8-dihydro-6H-[1,7]naphthyridin-7-yl)-methanone
(6-Chloro-pyrazolo[1,5-a]pyrimidin-2-yl)-(8-methyl-5,8-dihydro-6H-[1,7]naphthyridin-7-yl)-methanone
(6-Bromo-pyrazolo[1,5-a]pyrimidin-2-yl)-(1-methyl-3,4-dihydro-1H-[2,7]naphthyridin-2-yl)-methanone
(6-Chloro-pyrazolo[1,5-a]pyrimidin-2-yl)-(1-methyl-3,4-dihydro-1H-[2,7]naphthyridin-2-yl)-methanone
(6-Bromo-pyrazolo[1,5-a]pyrimidin-2-yl)-(1-methyl-3,4-dihydro-1H-[2,6]naphthyridin-2-yl)-methanone
(6-Chloro-pyrazolo[1,5-a]pyrimidin-2-yl)-(1-methyl-3,4-dihydro-1H-[2,6]naphthyridin-2-yl)-methanone
5-[(6-Bromopyrazolo[1,5-a]pyrimidin-2-yl)carbonyl]-3-phenyl-4,5,6,7-tetrahydroisoazolo[4,5-c]pyridine;
5-[(6-Bromopyrazolo[1,5-a]pyrimidin-2-yl)carbonyl]-3-phenyl-4,5,6,7-tetrahydroisoxazolo[4,5-c]pyridine;
6-Bromo-2-[(4-methyl-6,7-dihydrothieno[3,2-c]pyridin-5(4H)-yl)carbonyl]pyrazolo[1,5-a]pyrimidine;
(6-Bromo-pyrazolo[1,5-a]pyrimidin-2-yl)-(2,4-dimethyl-6,7-dihydro-4H-thieno[3,2-c]pyridin-5-yl)-methanone;
(6-Bromo-pyrazolo[1,5-a]pyrimidin-2-yl)-(3,4-dimethyl-6,7-dihydro-4H-thieno[3,2-c]pyridin-5-yl)-methanone;
(6-Chloro-pyrazolo[1,5-a]pyrimidin-2-yl)-(2,4-dimethyl-6,7-dihydro-4H-thieno[3,2-c]pyridin-5-yl)-methanone;
(6-Bromo-pyrazolo[1,5-a]pyrimidin-2-yl)-(4-ethyl-6,7-dihydro-4H-thieno[3,2-c]pyridin-5-yl)-methanone;
(6-Chloro-pyrazolo[1,5-a]pyrimidin-2-yl)-(4-ethyl-6,7-dihydro-4H-thieno[3,2-c]pyridin-5-yl)-methanone;
(6-Chloro-pyrazolo[1,5-a]pyrimidin-2-yl)-(4-methyl-6,7-dihydro-4H-thieno[3,2-c]pyridin-5-yl)-methanone;
6-Chloro-2-[(4-methyl-6,7-dihydrofuro[3,2-c]pyridin-5(4H)-yl)carbonyl]pyrazolo[1,5-a]pyrimidine;
6-Chloro-2-[(2,3,4-trimethyl-6,7-dihydrothieno[3,2-c]pyridin-5(4H)-yl)carbonyl]pyrazolo-[1,5-a]pyrimidine;
6-Bromo-2-[(4-methyl-6,7-dihydrofuro[3,2-c]pyridin-5(4H)-yl)carbonyl]pyrazolo[1,5-a]pyrimidine;
6-Bromo-2-[(2,3,4-trimethyl-6,7-dihydrothieno[3,2-c]pyridin-5(4H)-yl)carbonyl]pyrazolo-[1,5-a]pyrimidine;
(6-Bromo-pyrazolo[1,5-a]pyrimidin-2-yl)-(4-methyl-6,7-dihydro-4H-thieno[3,2-c]pyridin-5-yl)-methanone;
(6-Bromo-pyrazolo[1,5-a]pyrimidin-2-yl)-(4-methyl-6,7-dihydro-4H-thieno[3,2-c]pyridin-5-yl)-methanone;
(6-Bromo-pyrazolo[1,5-a]pyrimidin-2-yl)-(6-methyl-6,7-dihydro-4H-thieno[3,2-c]pyridin-5-yl)-methanone;
(6-Chloro-pyrazolo[1,5-a]pyrimidin-2-yl)-(4-trifluoromethyl-6,7-dihydro-4H-thieno[3,2-c]pyridin-5-yl)-methanone;
(6-Chloro-pyrazolo[1,5-a]pyrimidin-2-yl)-(6-methyl-6,7-dihydro-4H-thieno[3,2-c]pyridin-5-yl)-methanone;
(6-Chloro-pyrazolo[1,5-a]pyrimidin-2-yl)-(2,4-dimethyl-6,7-dihydro-4H-furo[3,2-c]pyridin-5-yl)-methanone;
(6-Bromo-pyrazolo[1,5-a]pyrimidin-2-yl)-(2,4-dimethyl-6,7-dihydro-4H-furo[3,2-c]pyridin-5-yl)-methanone;
(6-Bromo-pyrazolo[1,5-a]pyrimidin-2-yl)-(4-methyl-6,7-dihydro-4H-oxazolo[4,5-c]pyridin-5-yl)-methanone;
(6-Bromo-pyrazolo[1,5-a]pyrimidin-2-yl)-(2-fluoro-4-methyl-6,7-dihydro-4H-oxazolo[4,5-c]pyridin-5-yl)-methanone;
(6-Bromo-pyrazolo[1,5-a]pyrimidin-2-yl)-(2-chloro-4-methyl-6,7-dihydro-4H-oxazolo-[4,5-c]pyridin-5-yl)-methanone;
(6-Bromo-pyrazolo[1,5-a]pyrimidin-2-yl)-(2,4-dimethyl-6,7-dihydro-4H-oxazolo[4,5-c]pyridin-5-yl)-methanone;
(6-Bromo-pyrazolo[1,5-a]pyrimidin-2-yl)-(2,4-dimethyl-6,7-dihydro-4H-oxazolo[4,5-c]pyridin-5-yl)-methanone;
(6-Bromo-pyrazolo[1,5-a]pyrimidin-2-yl)-(2-methoxy-4-methyl-6,7-dihydro-4H-oxazolo-[4,5-c]pyridin-5-yl)-methanone;
(6-Bromo-pyrazolo[1,5-a]pyrimidin-2-yl)-(1-methyl-1,3,4,5-tetrahydro-[2]pyrindin-2-yl)-methanone;
(6-Bromo-pyrazolo[1,5-a]pyrimidin-2-yl)-(1-methyl-1,3,4,7-tetrahydro-[2]pyrindin-2-yl)-methanone;
(6-Chloro-pyrazolo[1,5-a]pyrimidin-2-yl)-(1-methyl-1,3,4,5-tetrahydro-[2]pyrindin-2-yl)-methanone;
(6-Chloro-pyrazolo[1,5-a]pyrimidin-2-yl)-(1-methyl-1,3,4,7-tetrahydro-[2]pyrindin-2-yl)-methanone;
(6-Bromo-pyrazolo[1,5-a]pyrimidin-2-yl)-(1,5,5-trimethyl-1,3,4,5-tetrahydro-[2]pyrindin-2-yl)-methanone;
(6-Bromo-pyrazolo[1,5-a]pyrimidin-2-yl)-(1,7,7-trimethyl-1,3,4,7-tetrahydro-[2]pyrindin-2-yl)-methanone;
(6-Chloro-pyrazolo[1,5-a]pyrimidin-2-yl)-(1,5,5-trimethyl-1,3,4,5-tetrahydro-[2]pyrindin-2-yl)-methanone;
(6-Chloro-pyrazolo[1,5-a]pyrimidin-2-yl)-(1,7,7-trimethyl-1,3,4,7-tetrahydro-[2]pyrindin-2-yl)-methanone;
(6-Bromo-pyrazolo[1,5-a]pyrimidin-2-yl)-[7-methyl-1-(1H-tetrazol-5-yl)-1,4,5,7-tetrahydro-pyrrolo[2,3-c]pyridin-6-yl]-methanone;
(6-Chloro-pyrazolo[1,5-a]pyrimidin-2-yl)-[7-methyl-1-(1H-tetrazol-5-yl)-1,4,5,7-tetrahydro-pyrrolo[2,3-c]pyridin-6-yl]-methanone;
(6-Bromo-pyrazolo[1,5-a]pyrimidin-2-yl)-[4-methyl-1-(1H-tetrazol-5-yl)-1,4,6,7-tetrahydro-pyrrolo[3,2-c]pyridin-5-yl]-methanone;
(6-Chloro-pyrazolo[1,5-a]pyrimidin-2-yl)-[4-methyl-1-(1H-tetrazol-5-yl)-1,4,6,7-tetrahydro-pyrrolo[3,2-c]pyridin-5-yl]-methanone;
(6-Bromo-pyrazolo[1,5-a]pyrimidin-2-yl)-[4-methyl-1-(1H-tetrazol-5-yl)-2,4,6,7-tetrahydro-pyrrolo[3,4-c]pyridin-5-yl]-methanone;
(6-Chloro-pyrazolo[1,5-a]pyrimidin-2-yl)-[4-methyl-1-(1H-tetrazol-5-yl)-2,4,6,7-tetrahydro-pyrrolo[3,4-c]pyridin-5-yl]-methanone
and the optical isomers, polymorphs and pharmaceutically-acceptable acid and base addition salts, hydrates, and solvates thereof.

Such a compound of formula (I), which is selected from those of formula (IA):

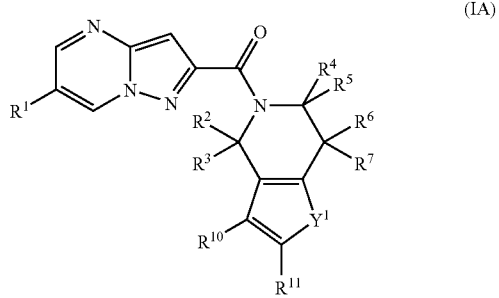

wherein
Y$^1$ represents NH, S, or O;
R$^1$ represents chloro or bromo;
R$^2$ represents hydrogen, C$_{1-6}$alkyl, amino, hydroxy, halogen or trifluoromethyl;
R$^3$ represents hydrogen, C$_{1-6}$alkyl, amino, hydroxy, halogen or trifluoromethyl;
R$^4$ represents hydrogen, C$_{1-6}$alkyl, amino, hydroxy, halogen or trifluoromethyl;
R$^5$ represents hydrogen, C$_{1-6}$alkyl, amino, hydroxy, halogen or trifluoromethyl;
R$^6$ represents hydrogen, C$_{1-6}$alkyl, amino, hydroxy, halogen or trifluoromethyl;
R$^7$ represents hydrogen, C$_{1-6}$alkyl, amino, hydroxy, halogen or trifluoromethyl and
R$^{10}$, R$^{11}$ independently represent hydrogen, halogen, amino, hydroxy, nitro, cyano, trifluoromethyl, trifluoromethoxy, phenyl, C$_{1-6}$alkyl or C$_{1-6}$alkoxy,
and the optical isomers, polymorphs and pharmaceutically-acceptable acid and base addition salts, hydrates, and solvates thereof.

Such a compound of formula (IA), wherein R$^2$, R$^3$, R$^4$ and R$^5$ independently represent hydrogen or methyl; R$^6$ and R$^7$ represent hydrogen; and R$^{10}$ and R$^{11}$ independently represent hydrogen, halogen, trifluoromethyl or C$_{1-6}$alkyl.

Such a compound of formula (IA), wherein R$^2$, R$^3$, R$^4$, R$^5$, R$^6$ and R$^7$ independently represent hydrogen, methyl, ethyl, fluoro or trifluoromethyl.

Such a compound of formula (IA), wherein R$^2$, R$^3$, R$^4$, R$^5$, R$^6$ and R$^7$ independently represent hydrogen or methyl.

Such a compound of formula (IA), wherein R$^2$, R$^3$, R$^4$ and R$^5$ independently represent hydrogen or methyl and R$^6$ and R$^7$ represent hydrogen.

Such a compound of formula (IA), wherein Y$^1$ represents S or O.

The invention also relates to compounds of the formula (I) or of the formula (Ia) which are marked by radioactive atoms. Typical compounds include those where one or more hydrogens are substituted by tritium, where one or more C$^{12}$ are substituted by C$^{14}$, where one or more fluor atoms are substituted by F$^{18}$ or other isotopes. These can be used for the treatment of diseases (e.g. cancer) but also for diagnostic purposes. The radioactive atoms exchanged in the molecule are often isotopes of carbon, hydrogen, halogen, sulphur or phosphor.

The invention in general relates to the use of a metabotropic glutamate receptor modulator (and in particular of a mGluR5 modulator) for the preparation of a medicament and for the treatment of various diseases as mentioned hereunder in a mammal, including humans.

Moreover, the invention relates to the use of a compound of formula (I) or of formula (Ia) as defined above or an optical isomer, pharmaceutically acceptable salt, hydrate, solvate or polymorph thereof for the preparation of a medicament and for the treatment of a mammal, including humans.

Further, the invention relates to the use of a compound for the preparation of a medicament for treating or preventing a condition or disease associated with abnormal glutamate neurotransmission. Such a use includes the use of a compound for the preparation of a medicament for the prevention and/or treatment of a condition or disease in an animal including a human being which condition or disease is affected or facilitated by the negative modulatory effect of mGluR5 modulators.

The invention is dealing with the use of a mGluR5 modulator and in particular a compound according to formula (I), for the preparation of a medicament, including for the conditions or diseases selected from those mentioned earlier in the description.

The invention also relates to the use of a mGluR5 modulator, in particular a compound according to formula (I) wherein the condition associated with abnormal glutamate neurotransmission is selected from those mentioned earlier in the description.

Further, the invention relates to the use of a compound wherein the condition associated with abnormal glutamate neurotransmission is selected from: neuropathic pain, diabetic neuropathic pain (DNP), cancer pain, pain related to rheumathic arthritis, inflammatory pain, L-dopa-induced and tardive dyskinesias, Parkinson's disease, anxiety disorders, Huntington's chorea, epilepsy, Alzheimer's disease, positive and negative symptoms of schizophrenia, cognitive impairment, reflux, migrane or for cognitive enhancement and/or neuroprotection.

Further, the invention relates to a pharmaceutical composition comprising as active ingredient at least one compound of formula (I) as defined above or an optical isomer, pharmaceutically acceptable salt, hydrate, solvate or polymorph thereof, together with one or more pharmaceutically acceptable excipients.

The invention also relates to the process for the synthesis or preparation of a compound of formula (I)

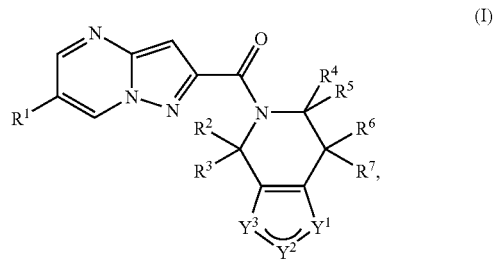

wherein
Y$^1$, Y$^2$ and Y$^3$ independently represent CR$^{10}$, CR$^{11}$, CR$^{10}$R$^{11}$, NR$^{12}$, S or O, whereby at least one of Y$^1$, Y$^2$ and Y$^3$ represents CR$^{10}$;
or Y$^1$ and Y$^2$ together represent a group R$^{10}$C=N; R$^{10}$C=CR$^{11}$; R$^{10}$R$^{11}$C—C(=O) or R$^{12}$N—(C=O);
or Y$^2$ and Y$^3$ together represent a group R$^{10}$C=N; R$^{10}$C=CR$^{11}$; R$^{10}$R$^{11}$C—C(=O) or R$^{12}$N—(C=O);
R$^1$ represents chloro or bromo;
R$^2$ represents hydrogen, C$_{1-6}$alkyl, C$_{3-7}$cycloalkyl or trifluoromethyl;
R$^3$ represents hydrogen, C$_{1-6}$alkyl, C$_{3-7}$cycloalkyl or trifluoromethyl; or
R$^2$ and R$^3$ together with the carbon atom of the ring represent a carbonyl group;
R$^4$ represents hydrogen, C$_{1-6}$alkyl, C$_{3-7}$cycloalkyl or trifluoromethyl;
R$^5$ represents hydrogen, C$_{1-6}$alkyl, C$_{3-7}$cycloalkyl or trifluoromethyl; or
R$^4$ and R$^5$ together with the carbon atom of the ring represent a carbonyl group;
R$^6$ represents hydrogen, C$_{1-6}$alkyl, C$_{3-7}$cycloalkyl or trifluoromethyl;
R$^7$ represents hydrogen, C$_{1-6}$alkyl, C$_{3-7}$cycloalkyl or trifluoromethyl; or
R$^6$ and R$^7$ together with the carbon atom of the ring represent a carbonyl group;

R² or R³ together with R⁶ or R⁷ may form a bivalent radical of type CH₂—CH₂ or CH₂—O;

$R^{10}$ and $R^{11}$ independently represent hydrogen, halogen, amino, hydroxy, nitro, cyano, trifluoromethyl, trifluoromethoxy, aryl, $C_{1-6}$alkyl, $C_{3-7}$-cycloalkyl, $C_{2-6}$alkenyl, $C_{2-6}$alkynyl, $C_{1-6}$alkoxy, $C_{3-7}$-cycloalkyloxy, $C_{2-6}$alkenyloxy, $C_{2-6}$alkynyloxy, heteroaryl, heterocyclyl, aryloxy, heteroaryloxy, heterocyclyloxy, $C_{1-6}$alkylamino, di-$C_{1-6}$alkylamino, $C_{3-7}$-cycloalkylamino, di-$C_{3-7}$-cycloalkylamino, $C_{1-6}$alkyl-$C_{3-7}$-cycloalkylamino, $C_{2-6}$alkenylamino, $C_{2-6}$alkynylamino, di-$C_{2-6}$alkenylamino, di-$C_{2-6}$alkynylamino, $C_{1-6}$alkyl-$C_{2-6}$-alkenylamino, $C_{1-6}$alkyl-$C_{2-6}$-alkynylamino, $C_{2-6}$alkenyl-$C_{3-7}$-cycloalkylamino, $C_{2-6}$alkynyl-$C_{3-7}$-cycloalkylamino, $C_{2-6}$alkenyl-$C_{2-6}$-alkynylamino arylamino, diarylamino, aryl-$C_{1-6}$alkylamino, aryl-$C_{2-6}$alkenylamino, aryl-$C_{2-6}$alkynylamino, aryl-$C_{3-7}$-cycloalkylamino, heteroarylamino, diheteroarylamino, heteroaryl-$C_{1-6}$alkylamino, heteroaryl-$C_{2-6}$alkenylamino, heteroaryl-$C_{2-6}$alkynylamino, heteroaryl-$C_{3-7}$-cycloalkylamino, heteroarylarylamino, heterocyclylamino, diheterocyclylamino, heterocyclyl-$C_{1-6}$alkylamino, heterocyclyl-$C_{2-6}$alkenylamino, heterocyclyl-$C_{2-6}$alkynylamino, heterocyclyl-$C_{3-7}$-cycloalkylamino, heterocyclylarylamino, heterocyclylheteroarylamino, acyl, acyloxy, acylamino, $C_{1-6}$alkoxycarbonyl, $C_{3-7}$-cycloalkoxy-carbonyl, $C_{2-6}$alkenyloxycarbonyl, $C_{2-6}$alkynyloxycarbonyl, aryloxycarbonyl, heteroaryloxycarbonyl, heterocyclyloxycarbonyl, aminocarbonyl, $C_{1-6}$alkylamino-carbonyl, di-$C_{1-6}$alkylaminocarbonyl, $C_{3-7}$-cycloalkylaminocarbonyl, di-$C_{3-7}$-cycloalkylaminocarbonyl, $C_{1-6}$alkyl-$C_{3-7}$-cycloalkylaminocarbonyl, $C_{2-6}$alkenyl-aminocarbonyl, $C_{2-6}$alkynylaminocarbonyl, di-$C_{2-6}$alkenylaminocarbonyl, di-$C_{2-6}$alkynylaminocarbonyl, $C_{1-6}$alkyl$C_{2-6}$-alkenylaminocarbonyl, $C_{1-6}$alkyl-$C_{2-6}$-alkynyl-aminocarbonyl, $C_{2-6}$alkenyl-$C_{3-7}$-cycloalkylaminocarbonyl, $C_{2-6}$alkynyl-$C_{3-7}$-cycloalkylaminocarbonyl, $C_{2-6}$alkenyl-$C_{2-6}$-alkynylaminocarbonyl, arylaminocarbonyl, diarylaminocarbonyl, aryl-$C_{6}$alkylaminocarbonyl, aryl-$C_{2-6}$alkenylaminocarbonyl, aryl-$C_{2-6}$alkynylaminocarbonyl, aryl-$C_{3-7}$-cycloalkylaminocarbonyl heteroarylaminocarbonyl, diheteroarylaminocarbonyl, heteroaryl-$C_{1-6}$alkylaminocarbonyl, heteroaryl-$C_{2-6}$alkenylaminocarbonyl, heteroaryl-$C_{2-6}$alkynylaminocarbonyl, heteroaryl-$C_{3-7}$-cycloalkylaminocarbonyl, heteroarylarylaminocarbonyl, heterocyclylaminocarbonyl, diheterocyclylaminocarbonyl, heterocyclyl-$C_{1-6}$alkylaminocarbonyl, heterocyclyl-$C_{2-6}$alkenylaminocarbonyl, heterocyclyl-$C_{2-6}$alkynylaminocarbonyl, heterocyclyl-$C_{3-7}$-cycloalkyl-aminocarbonyl, heterocyclylarylaminocarbonyl, heterocyclylheteroarylaminocarbonyl, $C_{1-6}$alkylsulfinyl, $C_{3-7}$-cycloalkylsulfinyl, $C_{2-6}$alkenylsulfinyl, $C_{2-6}$alkynylsulfinyl, arylsulfinyl, heteroarylsulfinyl, heterocyclylsulfinyl, $C_{1-6}$alkylsulfonyl, $C_{3-7}$-cycloalkylsulfonyl, $C_{2-6}$alkenylsulfonyl, $C_{2-6}$alkynylsulfonyl, arylsulfonyl, heteroarylsulfonyl, heterocyclylsulfonyl, $C_{1-6}$alkylsulfonylamino, or arylsulfonylamino; and $R^{12}$ represents hydrogen, $C_{1-6}$alkyl, $C_{3-7}$cycloalkyl, $C_{2-6}$alkenyl, $C_{2-6}$alkynyl, acyl, aryl, heteroaryl, heterocyclyl, $C_{1-6}$alkylamino-carbonyl, di-$C_{1-6}$alkylaminocarbonyl, $C_{1-6}$alkylsulfonyl, arylsulfonyl or heteroarylsulfonyl;

and optical isomers, pharmaceutically acceptable salts, hydrates, solvates, and polymorphs thereof, wherein a compound of formula (II)

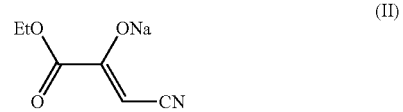

is suspended in a mixture of ethanol and water and treated with hydrochloric acid, followed by reaction with H₂NNHCOOCH₃ to yield a compound of formula (III)

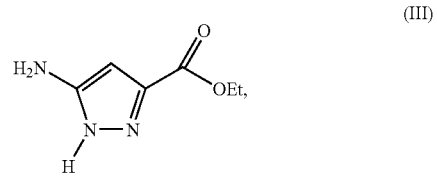

which then is reacted with a compound of formula (IV)

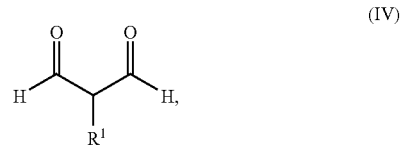

to yield a parazolopyrimidine compound of formula (V)

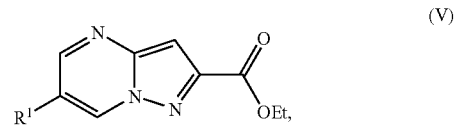

which is hydrolyzed under acidic conditions to yield a compound of formula (VI)

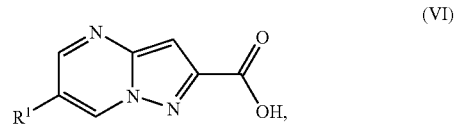

which then is treated with an amine of formula (VII)

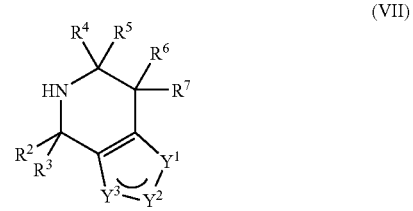

(e.g., in the presence of a condensing agent), to yield a compound of Formula (I), which is converted, if desired, to a pharmaceutically acceptable salt, hydrate, solvate, or polymorph.

The invention further relates to the compound of formula (VII), which, for example, can serve as an intermediate, (VII)

wherein
$Y^1$, $Y^2$ and $Y^3$ independently represent $CR^{10}$, $CR^{11}$, $CR^{10}R^{11}$, $NR^{12}$, S or O, whereby at least one of $Y^1$, $Y^2$ and $Y^3$ represents $CR^{10}$;
or $Y^1$ and $Y^2$ together represent a group $R^{10}C=N$; $R^{10}C=CR^{11}$; $R^{10}R^{11}C-C(=O)$ or $R^{12}N-(C=O)$;
or $Y^2$ and $Y^3$ together represent a group $R^{10}C=N$; $R^{10}C=CR^{11}$; $R^{10}R^{11}C-C(=O)$ or $R^{12}N-(C=O)$;
$R^1$ represents chloro or bromo;
$R^2$ represents hydrogen, $C_{1-6}$alkyl, $C_{3-7}$cycloalkyl or trifluoromethyl;
$R^3$ represents hydrogen, $C_{1-6}$alkyl, $C_{3-7}$cycloalkyl or trifluoromethyl; or
$R^2$ and $R^3$ together with the carbon atom of the ring represent a carbonyl group;
$R^4$ represents hydrogen, $C_{1-6}$alkyl, $C_{3-7}$cycloalkyl or trifluoromethyl;
$R^5$ represents hydrogen, $C_{1-6}$alkyl, $C_{3-7}$cycloalkyl or trifluoromethyl; or
$R^4$ and $R^5$ together with the carbon atom of the ring represent a carbonyl group;
$R^6$ represents hydrogen, $C_6$alkyl, $C_{3-7}$cycloalkyl or trifluoromethyl;
$R^7$ represents hydrogen, $C_{1-6}$alkyl, $C_{3-7}$cycloalkyl or trifluoromethyl; or
$R^6$ and $R^7$ together with the carbon atom of the ring represent a carbonyl group;
$R^2$ or $R^3$ together with $R^6$ or $R^7$ may form a bivalent radical of type $CH_2-CH_2$ or $CH_2-O$.

The invention also relates to a further process for the synthesis of a compound selected from those of formula (I)

(I)

wherein
$Y^1$, $Y^2$ and $Y^3$ independently represent $CR^{10}$, $CR^{11}$, $CR^{10}R^{11}$, $NR^{12}$, S or O, whereby at least one of $Y^1$, $Y^2$ and $Y^3$ represents $CR^{10}$;
or $Y^1$ and $Y^2$ together represent a group $R^{10}C=N$; $R^{10}C=CR^{11}$; $R^{10}R^{11}C-C(=O)$ or $R^{12}N-(C=O)$;
or $Y^2$ and $Y^3$ together represent a group $R^{10}C=N$; $R^{10}C=CR^{11}$; $R^{10}R^{11}C-C(=O)$ or $R^{12}N-(C=O)$;
$R^1$ represents chloro or bromo;
$R^2$ represents hydrogen, $C_{1-6}$alkyl, $C_{3-7}$cycloalkyl or trifluoromethyl;
$R^3$ represents hydrogen, $C_{1-6}$alkyl, $C_{3-7}$cycloalkyl or trifluoromethyl; or
$R^2$ and $R^3$ together with the carbon atom of the ring represent a carbonyl group;
$R^4$ represents hydrogen, $C_{1-6}$alkyl, $C_{3-7}$cycloalkyl or trifluoromethyl;
$R^5$ represents hydrogen, $C_{1-6}$alkyl, $C_{3-7}$cycloalkyl or trifluoromethyl; or
$R^4$ and $R^5$ together with the carbon atom of the ring represent a carbonyl group;
$R^6$ represents hydrogen, $C_{1-6}$alkyl, $C_{3-7}$cycloalkyl or trifluoromethyl;
$R^7$ represents hydrogen, $C_{1-6}$alkyl, $C_{3-7}$cycloalkyl or trifluoromethyl; or
$R^6$ and $R^7$ together with the carbon atom of the ring represent a carbonyl group;
$R^2$ or $R^3$ together with $R^6$ or $R^7$ may form a bivalent radical of type $CH_2-CH_2$ or $CH_2-O$;
$R^{10}$, $R^{11}$ independently represent hydrogen, halogen, amino, hydroxy, nitro, cyano, trifluoromethyl, trifluoromethoxy, aryl, $C_{1-6}$alkyl, $C_{3-7}$-cycloalkyl, $C_{2-6}$alkenyl, $C_{2-6}$alkynyl, $C_{1-6}$alkoxy, $C_{3-7}$-cycloalkyloxy, $C_{2-6}$alkenyloxy, $C_{2-6}$alkynyloxy, heteroaryl, heterocyclyl, aryloxy, heteroaryloxy, heterocyclyloxy, $C_{1-6}$alkylamino, di-$C_{1-6}$alkylamino, $C_{3-7}$-cycloalkylamino, di-$C_{3-7}$-cycloalkylamino, $C_{1-6}$alkyl-$C_{3-7}$-cycloalkylamino, $C_{2-6}$alkenylamino, $C_{2-6}$alkynylamino, di-$C_{2-6}$alkenylamino, di-$C_{2-6}$alkynylamino, $C_{1-6}$alkyl-$C_{2-6}$-alkenylamino, $C_{1-6}$alkyl-$C_{2-6}$-alkynylamino, $C_{2-6}$alkenyl-$C_{3-7}$-cycloalkylamino, $C_{2-6}$alkynyl-$C_{3-7}$-cycloalkylamino, $C_{2-6}$alkenyl-$C_{2-6}$-alkynylamino arylamino, diarylamino, aryl-$C_{1-6}$alkylamino, aryl-$C_{2-6}$alkenylamino, aryl-$C_{2-6}$alkynylamino, aryl-$C_{3-7}$-cycloalkylamino, heteroarylamino, diheteroarylamino, heteroaryl-$C_{1-6}$alkylamino, heteroaryl-$C_{2-6}$alkenylamino, heteroaryl-$C_{2-6}$alkynylamino, heteroaryl-$C_{3-7}$-cycloalkylamino, heteroarylarylamino, heterocyclylamino, diheterocyclylamino, heterocyclyl-$C_{1-6}$alkylamino, heterocyclyl-$C_{2-6}$alkenylamino, heterocyclyl-$C_{2-6}$alkynylamino, heterocyclyl-$C_{3-7}$-cycloalkylamino, heterocyclylarylamino, heterocyclylhetero-arylamino, acyl, acyloxy, acylamino, $C_{1-6}$alkoxycarbonyl, $C_{3-7}$-cycloalkoxy-carbonyl, $C_{2-6}$alkenyloxycarbonyl, $C_{2-6}$alkynyloxycarbonyl, aryloxycarbonyl, heteroaryloxycarbonyl, heterocyclyloxycarbonyl, aminocarbonyl, $C_{1-6}$alkylamino-carbonyl, di-$C_{1-6}$alkylaminocarbonyl, $C_{3-7}$-cycloalkylaminocarbonyl, di-$C_{3-7}$-cycloalkylaminocarbonyl, $C_{1-6}$alkyl-$C_{3-7}$-cycloalkylaminocarbonyl, $C_{2-6}$alkenyl-aminocarbonyl, $C_{2-6}$alkynylaminocarbonyl, di-$C_{2-6}$alkenylaminocarbonyl, di-$C_{2-6}$alkynylaminocarbonyl, $C_{1-6}$alkyl-$C_{2-6}$-alkenylaminocarbonyl, $C_{1-6}$alkyl-$C_{2-6}$-alkynyl-aminocarbonyl, $C_{2-6}$alkenyl-$C_{3-7}$-cycloalkylaminocarbonyl, $C_{2-6}$alkynyl-$C_{3-7}$-cycloalkylaminocarbonyl, $C_{2-6}$alkenyl-$C_{2-6}$-alkynylaminocarbonyl, arylaminocarbonyl, diarylaminocarbonyl, aryl-$C_{1-6}$alkylaminocarbonyl, aryl-$C_{2-6}$alkenylaminocarbonyl, aryl-$C_{2-6}$alkynylaminocarbonyl, aryl-$C_{3-7}$-cycloalkylaminocarbonyl heteroarylaminocarbonyl, diheteroarylaminocarbonyl, heteroaryl-$C_{1-6}$alkylaminocarbonyl, heteroaryl-$C_{2-6}$alkenylaminocarbonyl, heteroaryl-$C_{2-6}$alkynylaminocarbonyl, heteroaryl-$C_{3-7}$-cycloalkylaminocarbonyl, heteroarylarylaminocarbonyl, heterocyclylaminocarbonyl, diheterocyclylamino-carbonyl, heterocyclyl-$C_{1-6}$alkylaminocarbonyl, heterocyclyl-$C_{2-6}$alkenylamino-carbonyl, heterocyclyl-$C_{2-6}$alkynylaminocarbonyl, heterocyclyl-$C_{3-7}$-cycloalkyl-aminocarbonyl, heterocyclylarylaminocarbonyl, heterocyclylheteroarylaminocarbonyl, $C_{1-6}$alkylsulfinyl, $C_{3-7}$-cycloalkylsulfinyl, $C_{2-6}$alkenylsulfinyl, $C_{2-6}$alkynylsulfinyl, arylsulfinyl, heteroarylsulfinyl, heterocyclylsulfinyl, $C_{1-6}$alkylsulfonyl, $C_{3-7}$- cycloalkylsulfonyl, $C_{2-6}$alkenylsulfonyl, $C_{2-6}$alkynylsulfonyl, arylsulfonyl, heteroarylsulfonyl, heterocyclylsulfonyl; $C_1$-$C_6$alkylsulfonylamino or arylsulfonylamino; and
$R^{12}$ represents hydrogen, $C_{1-6}$alkyl, $C_{3-7}$cycloalkyl, $C_{2-6}$alkenyl, $C_{2-6}$alkynyl, acyl, aryl, heteroaryl, heterocyclyl, $C_{1-6}$alkylamino-carbonyl, di-$C_{1-6}$alkylamino-carbonyl, $C_{1-6}$alkylsulfonyl, arylsulfonyl or heteroarylsulfonyl;
and optical isomers, pharmaceutically acceptable salts, hydrates, solvates, and polymorphs thereof,
wherein a compound of Formula (VIII)

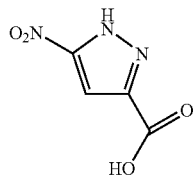
(VIII)

is dissolved in an alcoholic solvent and treated with an esterification facilitator (e.g. thionyl chloride) to yield a compound of Formula (IX)

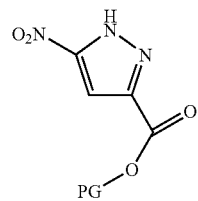
(IX)

wherein PG represents a protective group, such as a $C_{1-6}$alkyl group, which is reduced under standard conditions to yield a compound of Formula (X)

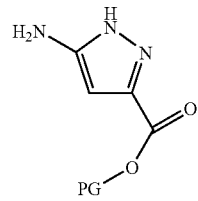
(X)

which then is reacted with a compound of Formula (IV)

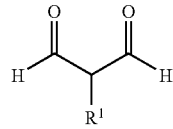
(IV)

to yield a pyrazolopyrimidine compound of Formula (XI)

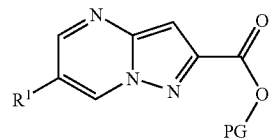
(XI)

which then is hydrolyzed (e.g., under acidic conditions) to yield a compound of Formula (VI)

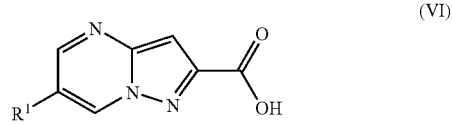
(VI)

which then is treated with an amine of Formula (VII)

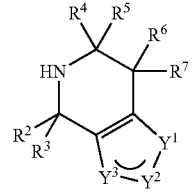
(VII)

(e.g., in the presence of a condensing agent), to yield a compound of Formula (I), which is converted, if desired, to a pharmaceutically acceptable salt, hydrate, solvate, or polymorph.

Moreover, the mGluR modulators as described above are expected to have a high activity when administered in combination with other substances exhibiting neurological effects via different mechanisms.

The invention also relates to a pharmaceutical composition comprising at least two different active ingredients, containing at least one compound of formula (I) as defined above, and furthermore containing at least one NMDA-antagonist, together with one or more pharmaceutically acceptable excipients. These compositions can be used for the treatment of CNS-related diseases, cognitive enhancement and for neuro-protection.

Simultaneous administration of Group I mGluR modulators and NMDA receptor antagonists has also been shown to provide neuroprotection in animal models (see e.g. Zieminska et al. Neurochemistry International, 2006, 66, 301-309; Zieminska et al. Neurochemistry International, 2003, 43, 481-492; Zieminska et al. Neurochemistry International, 2006, 48, 491-497).

With respect to the specific compounds as described above, the combined therapy exhibits a greater neuroprotective effect than monotherapy with either an mGluR modulator or an NMDA receptor antagonist. As particularly active NMDA receptor antagonist, the compound Memantine can be named, which is also known as 1-amino-3,5-dimethyladamantane (see U.S. Pat. No. 4,122,193; U.S. Pat. No. 4,273,774; and U.S. Pat. No. 5,061,703).

Furthermore, the compound Neramexane, which also is known as 1-amino-1,3,3,5,5-pentamethylcyclohexane, is a further active NMDA receptor antagonist and is disclosed in detail in U.S. Pat. No. 6,034,134 and U.S. Pat. No. 6,071,966. Memantine and Neramexane are systemically-active non-competitive NMDA receptor antagonists having moderate affinity for the receptor. They exhibit strong voltage dependent characteristics and fast blocking/unblocking kinetics (see e.g. Görtelmeyer et al., Arzneim-Forsch/Drug Res., 1992, 42:904-913; Winblad et al., Int. J. Geriat. Psychiatry, 1999, 14:135-146; Rogawski, Amino Acids, 2000, 19: 133-49; Danysz et al., Curr. Pharm. Des., 2002, 8:835-43; Jirgensons et. al. Eur. J. Med. Chem., 2000, 35: 555-565).

The combination of NMDA antagonists with mGluR5 modulators can be realized in a single pharmaceutical composition (as principally described in the prior art) comprising a mGluR5 modulator of the present invention and an NMDA receptor antagonist, in one pharmaceutical formulation, or in two separate pharmaceutical compositions or formulations, one comprising a mGluR5 modulator of the present invention and one comprising an NMDA receptor antagonist in a pharmaceutical formulation, to be administered conjointly (simultaneously or sequentially). For the sequential administration to be considered "conjoint", however, the mGluR5 modulator of the present invention and the NMDA receptor antagonist must be administered separated by a time interval that still permits the resultant beneficial effect in a mammal. For example, the mGluR5 modulator of the present invention and the NMDA receptor antagonist must be administered on the same day (e.g., each—once or twice daily), preferably within an hour of each other, and most preferably simultaneously.

This invention also relates to a pharmaceutical composition comprising a combination of a compound of formula (I) as described above and an NMDA receptor antagonist. Of particular interest is a composition, wherein the NMDA receptor antagonist is selected from Memantine and Neramexane (or a combination thereof) and pharmaceutically acceptable salts, polymorphs, hydrates and solvates thereof.

The invention also relates to a pharmaceutical composition comprising at least two different active ingredients, containing at least one compound of formula (I) as defined above, and furthermore containing at least one of L-DOPA, another dopaminomimetics (in particular an antiparkinsonian dopaminomimetics e.g. bromocriptine, cabergolin, ropinirole, pramiperole, pergolide, rotigotine), and a neuroleptic (in particular a classical neuroleptic, e.g. haloperidol, perphenazin, chlorpromazine, metoclopramide).

These combination products can e.g. be used for the treatment of CNS-related disorders and diseases. Because of the antidyskinetic effect of the compounds of formula (I), drug induced dyskinesias, neuroleptic-induced dyskinesias, haloperidol-induced dyskinesias, dopaminomi-metic-induced dyskinesias can be treated in addition to the conditions which are typically treated with L-Dopa, dopaminomimetics or neuroleptics.

The invention also relates to a method of providing neuroprotection to a living animal, including a human, comprising the step of administering to a living animal, including a human, a therapeutically effective amount of a composition as described.

This invention is also dealing with the compounds of formula (I) for the use as a medicament. Furthermore, the invention relates to the use of a compound of formula (I) for the manufacture of a medicament for the treatment of the diseases and conditions mentioned above.

Furthermore, the invention relates to the use of a composition as described for the manufacture of a medicament to provide neuroprotection in an animal, including a human.

Furthermore, the invention relates to the use of a compound of formula (I) in the manufacture of a medicament for treatment of a condition associated with abnormal glutamate neurotransmission or in which modulation of mGluR5 receptors results in therapeutic benefit. The disorders which can be treated have already been described above. Such conditions and indications include:

a) For mGluR5 modulators: chronic pain, neuropathic pain, diabetic neuropathic pain (DNP), cancer pain, pain related to rheumathic arthritis, inflammatory pain, L-dopa-induced dyskinesias, dopaminomimetic-induced dyskinesias, L-dopa-induced dyskinesias in Parkinson's disease therapy, dopaminomimetic-induced dyskinesias in Parkinson's disease therapy, tardive dyskinesias, Parkinson's disease, anxiety disorders, panic disorders, anxiety and panic disorders, social anxiety disorder (SAD), generalized anxiety disorder, substance-induced anxiety disorder, eating disorders, obesity, binge eating disorders, Huntington's chorea, epilepsy, Alzheimer's disease, positive and negative symptoms of schizophrenia, cognitive impairment, functional gastrointestinal disorders, gastroesophageal reflux disease (GERD), migraine, irritable bowel syndrome (IBS), or for cognitive enhancement and/or neuroprotection.

b) For negative modulation of mGluR5: chronic pain, neuropathic pain, diabetic neuropathic pain (DNP), cancer pain, pain related to rheumathic arthritis, inflammatory pain, L-dopa-induced dyskinesias, dopaminomimetic-induced dyskinesias, L-dopa-induced dyskinesias in Parkinson's disease therapy, dopaminomimetic-induced dyskinesias in Parkinson's disease therapy, tardive dyskinesias, Parkinson's disease, anxiety disorders, panic disorders, anxiety and panic disorders, social anxiety disorder (SAD), generalized anxiety disorder, substance-induced anxiety disorder, eating disorders, obesity, binge eating disorders, migraine, irritable bowel syndrome (IBS), functional gastrointestinal disorders, gastroesophageal reflux disease (GERD), Huntington's chorea and/or epilepsy.

c) For positive modulation of mGluR5: Alzheimer's disease, positive and/or negative symptoms of schizophrenia, cognitive impairment, or for cognitive enhancement and/or neuroprotection.

The mGluR5 negative modulators in general and in particular the compounds of formula (I) according to the invention can be used for the treatment of binge eating disorders.

DETAILED DESCRIPTION OF THE INVENTION

For the purpose of the present invention, in the compounds of formula (I) the carbon atom content of various hydrocarbon-containing moieties is indicated by a prefix designating the minimum and maximum number of carbon atoms in the moiety, i.e., the prefix $C_{i-j}$ indicates a moiety of the integer "i" to the integer "j" carbon atoms, inclusive. Thus, for example, $(C_{1-3})$alkyl refers to alkyl of one to three carbon atoms (i.e. 1, 2 or 3 carbon atoms), inclusive, (methyl, ethyl, propyl, and isopropyl), straight and branched forms thereof, $(C_{1-6})$ for instance refers to a radical of one to six carbon atoms (i.e. 1, 2, 3, 4, 5 or 6 carbon atoms).

As used herein, the following definitions are applicable unless otherwise described, the term "$C_{1-6}$alkyl" represents straight or branched chain alkyl groups which may be optionally substituted by one or more substituents selected from halogen, trifluoromethyl, $C_{1-6}$alkoxy, amino, hydroxy, $C_{1-6}$alkylamino, and di-($C_{1-6}$alkyl)amino. Examples of such alkyl groups include methyl, ethyl, n-propyl, 2-propyl, n-butyl, tert-butyl, —$CF_3$, —$C_2F_5$, —$CBr_3$ and —$CCl_3$.

The term "$C_{2-6}$alkenyl" represents straight or branched chain alkenyl groups. The term "$C_{1-6}$alkoxy" represents straight or branched chain —O—$C_{1-6}$alkyl groups which may be optionally substituted by one or more substituents selected from halogen, trifluoromethyl, amino, hydroxy, $C_{1-6}$alkylamino and di-($C_{1-6}$alkyl)amino. Examples of such alkoxy groups include methoxy, ethoxy, n-propoxy, i-propoxy, —$OCF_3$ and —$OC_2F_5$.

The term "cyclo$C_{3-12}$alkyl" represents monocyclic or bicyclic, or tricyclic alkyl groups, including cyclopropyl, cyclobutyl, cyclopentyl, cyclohexyl, bicyclo[2.2.1]heptyl and adamantanyl, which may be optionally substituted by one or more substituents, which may be the same or different, selected independently from halogen, trifluoromethyl, trifluoromethoxy, $C_{1-6}$alkyl, $C_{2-6}$alkenyl, $C_{1-6}$alkoxy, amino, hydroxy, nitro, cyano, cyanomethyl, $C_{1-6}$alkoxycarbonyl, $C_{1-6}$alkylamino, and di-($C_{1-6}$alkyl)amino, $C_{1-6}$alkylcarbonylamino, and $C_{1-6}$alkylenedioxy.

The term "aryl" represents phenyl or naphthyl, wherein the phenyl or naphthyl group is optionally substituted by one or more substituents, which may be the same or different, selected independently from halogen, trifluoromethyl, trifluoromethoxy, $C_{1-6}$alkyl, hydroxy$C_{1-6}$alkyl $C_{2-6}$alkenyl, $C_{1-6}$alkoxy, amino, hydroxy, nitro, cyano, cyanomethyl, $C_{1-6}$alkoxycarbonyl, $C_{1-6}$alkylcarbonyloxy, $C_{1-6}$alkylamino, di-($C_{1-6}$alkyl)amino, $C_{1-6}$alkylcarbonylamino, aminocarbonyl, N—$C_{1-6}$alkylaminocarbonyl, di-N,N—$C_{1-6}$alkylaminocarbonyl, pyrrolidinyl, piperidinyl, morpholinyl, and piperazinyl, cycloC$_{3-12}$alkyl or optionally C$_{1-6}$alkylenedioxy.

The term "acyl" includes —(C=O)-alkyl; —(C=O)aryl; —(C=O)-aralkyl, —(C=O)-heterocyclyl, C$_{1-6}$-alkylcarbonyl, C$_{3-7}$cycloalkylcarbonyl, C$_{2-6}$alkenylcarbonyl, C$_{2-6}$alkynylcarbonyl, arylcarbonyl, heteroarylcarbonyl or heterocyclylcarbonyl, wherein the terms alkyl, aryl and heterocyclyl are defined as above. Examples are acetyl, propionyl, benzoyl or pivaloyl.

The term "heteroaryl" represents an aromatic 5-6 membered ring containing from one to four heteroatoms selected from oxygen, sulfur and nitrogen, or a bicyclic group comprising a 5-6 membered ring containing from one to four heteroatoms selected from oxygen, sulfur and nitrogen fused with a benzene ring or a 5-6 membered ring containing from one to four heteroatoms selected from oxygen, sulfur and nitrogen, wherein the heteroaryl group may be optionally substituted by one or more substituents, which may be the same or different, selected independently from halogen, trifluoromethyl, trifluoromethoxy, C$_{1-6}$alkyl, hydroxyC$_{1-6}$alkyl, C$_{2-6}$alkenyl, C$_{1-6}$alkoxy, amino, hydroxy, nitro, cyano, C$_{1-6}$alkoxycarbonyl, C$_{1-6}$alkoxycarbonyloxy, C$_{1-6}$alkylamino, and di-(C$_{1-6}$alkyl)amino, C$_{1-6}$alkylcarbonylamino, aminocarbonyl, N—C$_{1-6}$alkylaminocarbonyl, di-N,N—C$_{1-6}$alkylaminocarbonyl, pyrrolidinyl, piperidinyl, morpholinyl, cycloC$_{3-12}$alkyl, C$_{1-6}$alkylenedioxy and aryl. Representative heteroaryl groups include furanyl, thienyl, pyrrolyl, oxazolyl, isoxazolyl, isothiazolyl, oxadiazolyl, triazolyl, thiadiazolyl, thiazolyl, imidazolyl, oxadiazolyl, tetrazolyl, pyridinyl, pyrimidinyl, pyridazinyl, pyrazinyl, triazinyl, pyrazolyl, benzofuryl, benzothienyl, indolyl, indolizinyl, isoindolyl, indolinyl, indazolyl, benzimidazolyl, benzoxazolyl, benzothiazolyl, quinolinyl, quinazolinyl, quinoxalinyl, cinnolinyl, naphtyridinyl, and isoquinolinyl. Examples are pyridyl, pyrimidyl, thienyl, furyl and others.

The term "heterocyclyl" represents a saturated or unsaturated non-aromatic 3 to 12 membered ring comprising one to four heteroatoms selected from oxygen, sulfur and nitrogen, and a saturated or unsaturated non-aromatic bicyclic ring system having 3 to 12 members comprising one to six heteroatoms selected from oxygen, sulfur and nitrogen, wherein the heterocyclic ring or ring system is optionally substituted by one or more substituents selected independently from a halogen, trifluoromethyl, C$_{1-6}$alkyl, C$_{2-6}$alkenyl, C$_{1-6}$alkoxy, amino, hydroxy, nitro, cyano, C$_{1-6}$alkoxycarbonyl, C$_{1-6}$alkylamino, di-C$_{1-6}$alkylamino, pyrrolidinyl, piperidinyl, morpholinyl, pyridinyl, and aryl; examples of such heterocyclyl groups include piperidinyl, morpholinyl, thiomorpholinyl, imidazolidinyl, pyrazolidinyl, pyrrolidinyl, or piperazinyl, wherein the heterocyclic ring or ring system is linked to the group to which it is attached optionally via nitrogen or a carbon atom.

The term "halogen" represents fluorine, chlorine, bromine and iodine.

The compounds of the present invention are usually named according to the IUPAC or CAS nomenclature system. Abbreviations which are well known to one of ordinary skill in the art may be used (e.g. "Ph" for phenyl, "Me" for methyl, "Et" for ethyl, "h" for hour or hours, and "rt" for room temperature).

The term "analog" or "derivative" is used herein in the conventional pharmaceutical sense, to refer to a molecule that structurally resembles a reference molecule, but has been modified in a targeted and controlled manner to replace one or more specific substituents of the referent molecule with an alternate substituent, thereby generating a molecule which is structurally similar to the reference molecule. Synthesis and screening of analogs (e.g., using structural and/or biochemical analysis), to identify slightly modified versions of a known compound which may have improved or biased traits (such as higher potency and/or selectivity at a specific targeted receptor type, greater ability to penetrate blood-brain barriers, fewer side effects, etc.) is a drug design approach that is well known in pharmaceutical chemistry.

In addition, using methods known to those skilled in the art, analogs and derivatives of the compounds of the invention can be created which have improved therapeutic efficacy, i.e., higher potency and/or selectivity at a specific targeted receptor type, either greater or lower ability to penetrate mammalian blood-brain barriers (e.g., either higher or lower blood-brain barrier permeation rate), fewer side effects, etc.

The phrase "pharmaceutically acceptable", as used in connection with compositions of the invention, refers to molecular entities and other ingredients of such compositions that are physiologically tolerable and do not typically produce untoward reactions when administered to a mammal (e.g., human). Preferably, as used herein, the term "pharmaceutically acceptable" means approved by a regulatory agency of the Federal or a state government or listed in the U.S. Pharmacopeia or other generally recognized pharmacopeia for use in mammals, and more particularly in humans.

Compounds of the present invention may be in the form of pharmaceutically acceptable salts. "Pharmaceutically acceptable salts" refers to those salts which possess the biological effectiveness and properties of the parent compound and which are not biologically or otherwise undesirable. The nature of the salt is not critical, provided that it is non-toxic and does not substantially interfere with the desired pharmacological activity.

It will be appreciated by those skilled in the art that compounds of the invention having a chiral center may exist in and be isolated in optically active and racemic forms. Some compounds may exhibit polymorphism. It is to be understood that the present invention encompasses any racemic, optically active, polymorphic, tautomeric, or stereoisomeric form, or mixture thereof, of a compound of the invention, which possesses the useful properties described herein.

All patents, applications, publications, test methods, literature, and other materials cited in this application are hereby incorporated by reference.

The following Schemes 1-3 describe the preparation of compounds of Formula (I) of the present invention. All of the starting materials may be prepared by procedures described in these schemes, by procedures well known to one of ordinary skill in organic chemistry, or may be obtained commercially. All of the final compounds of the present invention may be prepared by procedures described in these charts or by procedures analogous thereto, which would be well known to one of ordinary skill in organic chemistry. All of the variables used in the schemes are as defined below or as in the claims. The compounds containing one or more chiral centers can be prepared as racemates or mixtures of various stereoisomers and then separated. However, they also can be prepared by a special enantioselective synthesis. For several of the chiral compounds, the enantiomers differ in pharmacological activity.

Compounds of the present invention may be synthesized according to Scheme 1.

5-Nitro-1H-pyrazole-3-carboxylic acid 1 is reduced under standard conditions, such as treatment with hydrogen in the presence of palladium(0) on carbon in a solvent such as methanol, to yield 5-amino-1H-pyrazole-3-carboxylic acid 2. Compound 2 is reacted with di-aldehyde 3, carrying a bromo or chloro substituent at the R$^1$ position, under acid conditions, such as acetic acid, at elevated temperatures to give 6-bromo- or 6-chloro-pyrazolo[1,5-a]pyrimidine-2-carboxylic acid (4). A compound of Formula I is prepared from 4 via reaction with an appropriate secondary amine 5 in the presence of a condensation agent, including, for example, O-(benzotriazol-1-yl)-N,N,N',N'-tetramethyluronium tetrafluoroborate ("TBTU") or N-(3-dimethylaminopropyl)-N'-ethylcarbodiimide (EDC).

Scheme 1: General procedure towards compounds of Formula I.

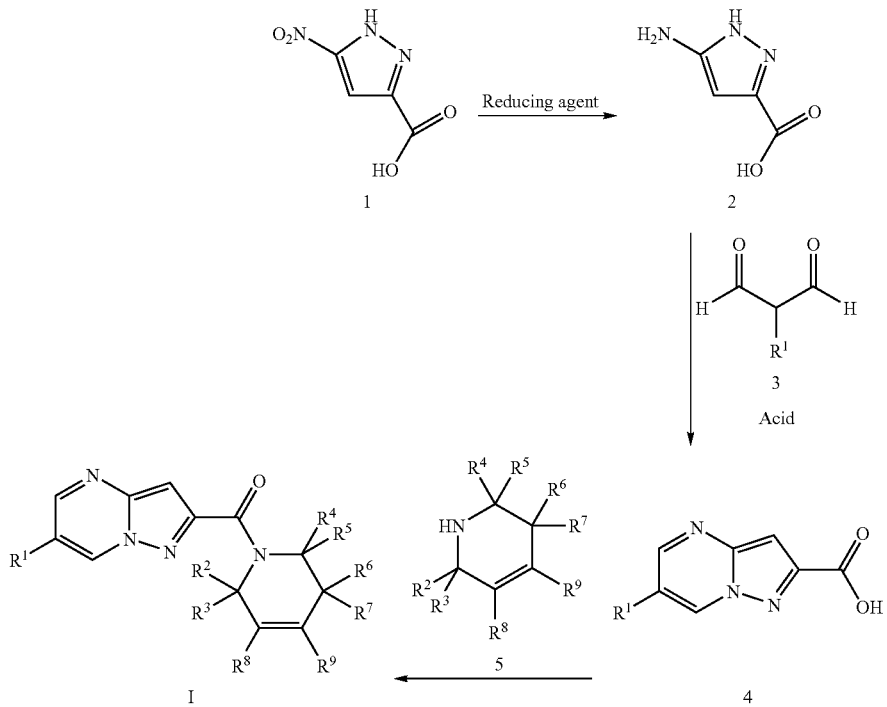

The amines (5) are commercially available or may be prepared according to literature procedures (see, for example, Bull. Soc. Chim. Belg., v.71, 1962; p. 592; US 2002/049223 A1 (2002/04/25); Chem. Ber., 84, 1951, p. 795-798; Bull. Soc. Chim. Fr.5, 4, 1937, p. 1265-1269; Zh. Obshch. Khim., 7, 1937, p. 1999-2004; Chem. Pharm. Bull., EN, 31, 8, 1983, p. 2583-2592; Tetrahedron, 28, 1972, p. 5999-6004; J. Org. Chem., 34, 8, 1969, p. 2478; Pharm. Chem. J. (Engl. Tran.); 5; 5; 1971, p. 260; Khfzan; Khim. Farm. Zh., 5, 5, 1971, p. 13).

Compound 4 may also be prepared according to Scheme 2.

Scheme 2: General procedure towards Compound 4.

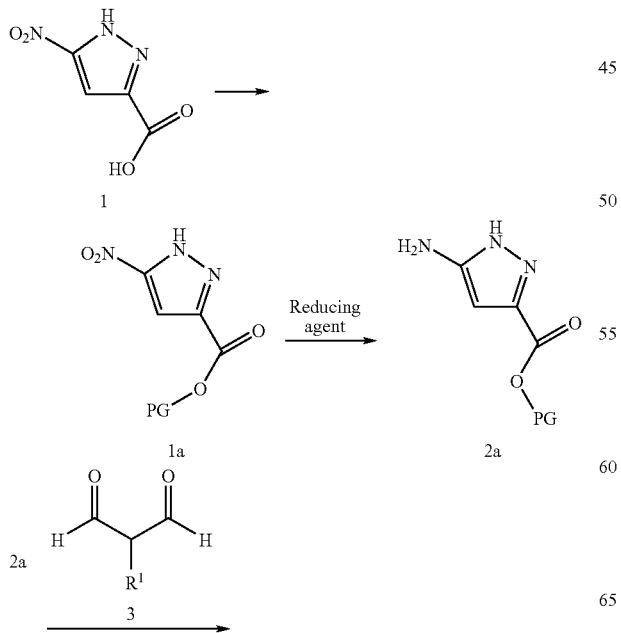

5-Nitro-3-pyrazole carboxylic acid 1 is dissolved in an alcoholic solvent, e.g. methanol or ethanol, and reacted with thionyl chloride to give compound 1a bearing an alkyl ester group. The term "PG" denotes any C1-6 alkyl chain, including branched alkyl chains, for example, methyl and ethyl groups. 5-Nitro-3-pyrazole-carboxylic acid alkyl ester 1a is reduced under standard conditions, such as treatment with hydrogen in the presence of palladium(0) on carbon in a solvent such as methanol, to yield 5-amino-1H-pyrazole-3-carboxylic acid alkyl ester 2a. Compound 2a is reacted with di-aldehyde 3, carrying a bromo or chloro substituent at the R1 position, under acid conditions, such as acetic acid, at elevated temperatures to give 6-bromo- or 6-chloro-pyrazolo [1,5-a]pyrimidine-2-carboxylic acid alkyl ester (4a). The ester 4a is hydrolyzed under acidic conditions such as sulphuric acid (30%) to yield 6-bromo- or 6-chloro-pyrazolo[1, 5-a]pyrimidine-2-carboxylic acid 4. A compound of Formula I is prepared from 4 via reaction with an appropriate secondary amine 5 as shown in Scheme 1.

Compound 4 may also be prepared according to Scheme 3. Ethyl 3-cyano-2-oxopropionate sodium salt ("NaCOPE") 6 is treated with methyl hydrazino formiate to yield ethyl 5-aminopyrazole-3-carboxylate 7. Compound 7 is reacted with dialdehyde 3, carrying a bromo or chloro substituent at the $R^1$ position, under acidic conditions, to yield ethyl 6-bromo- or 6-chloro-pyrazolo[1,5a]pyrimidine-2-carboxylate 8. The ester 8 is hydrolyzed under acidic conditions to yield 6-bromo- or 6-chloro-pyrazolo[1,5-a]pyrimidine-2-carboxylic acid 4. A compound of Formula I is prepared from 4 via reaction with an appropriate secondary amine 5 as shown in Scheme 1.

Scheme 3: General procedure towards Compound 4.

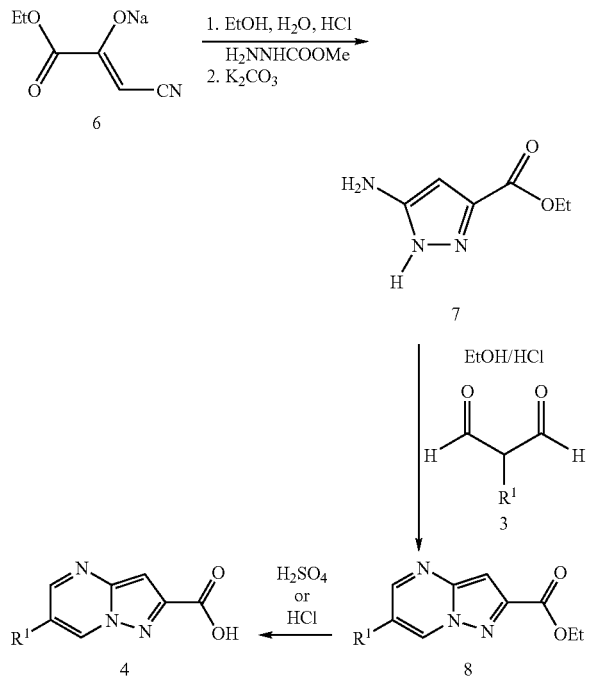

It will be appreciated that in the above transformations it may be necessary or desirable to protect any sensitive groups in the molecule of the compound in question in order to avoid undesirable side reactions.

EXPERIMENTAL PART

Hereinafter, "DMF" is defined as N,N-dimethylformamide, "HCl" as hydrochloric acid, "DMSO" as dimethylsulfoxide and "TBTU" as O-(benzotriazol-1-yl)-N,N,N',N'-tetra-methyluronium tetrafluoroborate.

Preparation 1

5-Nitro-3-pyrazole-carboxylic acid methyl ester

5-Nitro-3-pyrazol carboxylic acid (21.44 g, 136.5 mmol) is dissolved in dry methanol (200 mL). Then, thionyl chloride (9.9 mL, 136.5 mmol) is added slowly in a drop wise manner at RT. The reaction mixture is heated over night under reflux and under argon atmosphere. After cooling down, the solvent is evaporated under vacuum and the crude material is heated with boiling hexane (200 ml). After cooling down and removal of the hexane, the material is washed two times with 200 ml pentane. Then, the solvent is removed and the product is dried under vacuum to give 5-nitro-3-pyrazole-carboxylic acid methyl ester (22.35 g, 95.7%).

Preparation 2

5-Amino-3-pyrazole-carboxylic acid methyl ester

5-Nitro-3-pyrazole-carboxylic acid methyl ester (22.35 g, 130.61 mmol) is dissolved in each 160 mL THF und glacial acetic acid. Then, Pd—C (10%, 4.36 g) are added and the reaction is stirred for 6 days under hydrogen atmosphere at RT. Then, the mixture is filtered over celite and the solvent is removed under vacuum. The crude material is dissolved in methylene chloride (800 mL) and sodium hydrogen carbonate (200 g) are added, filtered and the solvent is again removed under vacuum. This procedure is repeated until the acetic acid smell is lost. 5-Amino-3-pyrazole-carboxylic acid methyl ester is isolated in high yields (16.91 g, 91.7%)

Preparation 3

6-Bromo-pyrazolo[1,5a]pyrimidine-2-carboxylic acid methyl ester

5-Amino-3-pyrazolcarboxylic acid methyl ester (16.91 g, 119.8 mmol) is dissolved in ethanol (2.4 L) and hydrochloric acid (37%, 12.5 mL, 150 mmol) is added. Then, a solution of 2-bromo-malonealdehyde (18.9 g, 125.2 mmol) is dissolved in ethanol (1.4 L) and is quickly added in a drop wise manner at RT. After 30 min, a precipitation is observed; after 6 hours the precipitate is removed and washed with 50 ml ethanol and thereafter with 50 ml diethyl ether. Here, 4.19 g of the clean product are isolated. After evaporation of the filtrate and crystallisation, additional 1.43 g product are obtained to yield 6-Bromo-pyrazolo[1,5a]pyrimidine-2-carboxylic acid methyl ester (5.62 g, 18.3% d.Th.). In case of a smaller scale reaction with only 1 g of the starting amine 5-amino-3-pyrazolcarboxylic acid methyl ester, the yield is much better e.g. 68%.

Preparation 4

6-Bromo-pyrazolo[1,5a]pyrimidine-2-carboxylic acid

6-Bromopyrazolo[1,5a]pyrimidin-2-carboxylic acid methyl ester (3.76 g, 14.68 mmol) is heated in 600 mL water, 190 mL sulphuric acid (30%) and 50 mL of the methanol/water mixture is removed from the reaction mixture via distillation. After cooling down, 50 mL water is added, the mixture is heated again and 50 mL of the alcohol-water mixture is removed. This cycle is repeated 6 times, the reaction mixture is cooled to RT and filtered over a glass filter. The crude material is washed with water (100 mL), acetone (20 mL) and ether (20 mL) and dried under vacuum to give 6-Bromo-pyrazolo[1,5a]pyrimidine-2-carboxylic acid (2.61 g, 10.78 mmol; 73.5%).

Physical characteristics are as follows: $^1$H NMR (DMSO): δ (ppm) 13.4, 9.7, 8.7, 7.2.

6-Chloro-pyrazolo[1,5a]pyrimidine-2-carboxylic acid

The hydrolysis of methyl 6-chloro-pyrazolo[1,5a]pyrimidine-2-carboxylate is performed under similar conditions as described above for methyl 6-bromo-pyrazolo[1,5a]pyrimidine-2-carboxylate.

Preparation 5

Ethyl 5-aminopyrazole-3-carboxylate

A 10 L three-necked flask is equipped with mechanical stirrer, reflux condenser and nitrogen inlet. To ethyl 3-cyano-2-oxopropionate sodium salt ("NaCOPE") (653.18 g; 4.0 mol), 585 mL of water, 3.6 L of ethanol and 350 mL of hydrochloric acid (12N, 4.2 mol) are added. The resulting suspension is stirred at RT for 15 min. Then, methyl hydrazino formiate (356.0 g; 3.95 mol) is added as a solid material. A slightly exothermic reaction occurs. After the mixture is stirred at RT for 6 h, another portion of methyl hydrazino formiate (12.0 g; 133.7 mmol) is added and the orange suspension is stirred at RT over night. Then potassium carbonate ($K_2CO_3$, 300.0 g; 2.17 mol) is added, followed by 250 mL of water. The internal temperature rises to 60° C. and a vigorous evolution of gas starts. The mixture is heated at reflux for four hours. After cooling to RT, the alcohol is evaporated to yield a red paste, which is taken up in 1 L of water and 3 L of ethyl acetate. The aqueous phase is extracted with another 500 mL portion of ethyl acetate. The organic extracts are washed with brine and dried over sodium sulfate ($Na_2SO_4$). After filtration the solvent is evaporated to yield 330 g of a brown paste. This crude product is mixed with 1 L of ether to give a light brown solid, which is separated from an orange liquid phase by filtration. The solid is dried under vacuum to yield 229.12 g (7). The liquid phase is evaporated; the residue is taken up in 250 mL of ether and cooled to −30° C. to yield another 15.09 g of 7. The total yield of 7 is 244.21 g (1.57 mol; 39.3%). Physical characteristics are as follows: $^1$H-NMR (DMSO): δ (ppm) 1.26, 4.21, 5.0, 5.76, 12.12.

Preparation 6

Ethyl 6-bromo-pyrazolo[1,5a]pyrimidine-2-carboxylate

A 2 L round bottom flask is charged with ethyl 5-aminopyrazole-3-carboxylate (7) (44.92 g; 289.50 mmol), 1.2 L of ethanol and 27 mL of hydrochloric acid (12N, 324.0 mmol). 2-Bromomalonaldehyde (43.71 g; 289.54 mmol) is added as a solid to the resulting yellow solution. A light brown solution is formed, from which a tan solid started to precipitate after 15 min. The suspension is stirred at RT over night and thereafter, filtered with suction. The solid is washed with 200 mL of ether to yield 62.50 g of (8a) after drying at 40° C./1 Torr. Additional crystals are isolated from the filtrate by concentration and cooling to −30° C. A total yield of 74.12 g (274.4 mmol; 94.8%) of 8a is obtained with a HPLC-purity>97%.

Physical characteristics are: $^1$H-NMR (DMSO): δ (ppm) 1.35, 4.39, 7.24, 8.74, 9.68.

Preparation 7

Sodium Salt of Chloromalonaldehyde

A 2 L Schlenk flask equipped with a 500 mL addition funnel is charged with mucochloric acid (100.0 g; 592.0 mmol) dissolved in 400 mL of ethanol. Then, a solution of aniline (108 mL; 1.18 mmol) in 400 mL of ethanol is added over a period of 5 min. The reaction proceeds exothermic via the formation of large amounts of carbon dioxide. Thereafter, the orange solution is heated to reflux for 5 min and then cooled down to RT. Overnight, a yellow precipitate is formed. 500 mL of HCl (1N) are added and the suspension is filtered with suction. The residue is washed with 200 mL of ethanol and 500 mL of ether. It is dried at 40° C./1 Torr to yield the hydrochloride of the dianilide (A) (107.8 g; 313.8 mmol; 53.7%) as a yellow solid which is used for the next step without further purification. In a 10 L three necked flask, 5 L of water are heated to reflux and the crude dianilide (A) (81.2 g; 239.3 mmol) is added in 6 portions over 15 min. The foaming suspension is heated for a further 15 min. Then, the mixture is cooled to RT overnight. After filtration with suction, the residue is suspended in 150 mL of ethanol and treated in an ultrasonic bath for 2 min. The mixture is filtered again with suction and washed with 200 mL of ether. The pale yellow residue is dried at 40° C./1 Torr to yield 39.68 g of the monoanilide of chloromalonaldehyde (B) (218.5 mmol; 91.2%) with a HPLC-purity>97%. A 1 L round bottom flask is charged with 39.68 g (B) (218.5 mmol) and 200 mL of NaOH (2N solution). It is heated to reflux for about 5 min until the solid is dissolved. At an internal temperature of 45° C., ethyl acetate (40 mL) is added. The alkaline aqueous layer is washed with a 40 mL portion of ethyl acetate and cooled to 5° C. After 12 hrs, the colorless needles are filtered off and washed with 50 mL of ethanol and 200 mL of ether. Concentration and cooling of the mother liquor yielded another crop of crystals. In total, 29.16 g (159.7 mmol; 73.1%) of the trihydrate of the sodium salt of chloromalonaldehyde (C) are isolated after drying at 40° C./1 Torr.

Preparation 8

Ethyl 6-chloro-pyrazolo[1,5a]pyrimidine-2-carboxylate

A 100 mL round bottom flask is charged with ethyl 5-aminopyrazole-3-carboxylate (7) (2.0 g; 12.89 mmol) and 50 mL of ethanol. To this solution hydrogen chloride (12 N, 1.2 mL; 14.4 mmol) is added. Then, the sodium salt of chloromalonaldehyde (C) (2.35 g; 12.89 mmol) is added as a solid in one portion. The resulting suspension is stirred at RT over night. Thereafter, it is filtered with suction and washed with 50 mL of ether. The residue is extracted with 120 mL of chloroform in a soxleth apparatus for 5 h. Then, the solvent is evaporated from the organic extract yielding 2.44 g of 8b (10.8 mmol; 83.9%) with >97% by HPLC.

Physical characteristics are: $^1$H-NMR (DMSO): δ (ppm) 1.35, 4.39, 7.25, 8.72, 9.63.

Preparation 9

6-Halogeno-pyrazolo[1,5a]pyrimidine-2-carboxylic acids

The hydrolysis of the ethyl 6-halogeno-pyrazolo[1,5a]pyrimidine-2-carboxylates (8) with aqueous acids leads to the carboxylic acids (4) in good yields (>80%). Hydrochloric acid is used to hydrolyze the 6-chloro-ester. The 6-bromo-derivative is hydrolyzed using sulfuric acid. In a typical hydrolysis the compounds (8) are suspended in water and the acid is added. Then, small amounts of alcohol-water-azeotrope are distilled off until no more ester is detected by TLC (MeCN+H2O=10+2, plate type: Alugram☐SIL G/UV254). The suspensions are cooled by means of an ice-water bath and filtered with suction. The residues are washed with water, acetone and ether. After drying at 40° C./1 Torr the 6-halogenopyrazolo[1,5a]pyrimidine-2-carboxylic acids (6) are examined by HPLC.

6-Bromo-pyrazolo[1,5a]pyrimidine-2-carboxylic acid

5 A 500 mL round bottom flask is charged with ethyl 6-bromo-pyrazolo[1,5a]pyrimidine-2-carboxylate (2.0 g;

7.41 mmol) and 240 mL of water. After addition of diluted sulfuric acid (30 vol %; 62 mL) the suspension is heated to reflux and 20 mL of an ethanol-waterazeotrope is distilled off. 20 mL of water are added to the suspension and another 20 mL portion is distilled off. After eight of these cycles, no more ester is detected by TLC. The mixture is cooled to 10° C. by means of an ice-bath. It is filtered with suction and washed with 100 mL of water, followed by 20 mL of acetone and 100 mL of ether. The residue is dried at 40° C./1 Torr to yield 1.54 g (6a) (6.36 mmol; 83.5) as a beige powder.

Physical characteristics are as follows: $^1$H-NMR (DMSO): δ (ppm) 7.21, 8.75, 9.70, 13.44.

6-Chloro-pyrazolo[1,5a]pyrimidine-2-carboxylic acid

The hydrolysis of ethyl 6-chloro-pyrazolo[1,5a]pyrimidine-2-carboxylate is performed under similar conditions as described above for ethyl 6-bromo-pyrazolo[1,5a]pyrimidine-2-carboxylate.

In order to prepare the amine component of the pyrazolopyrimidine compounds of formula (I) the following General Schemes can be used:

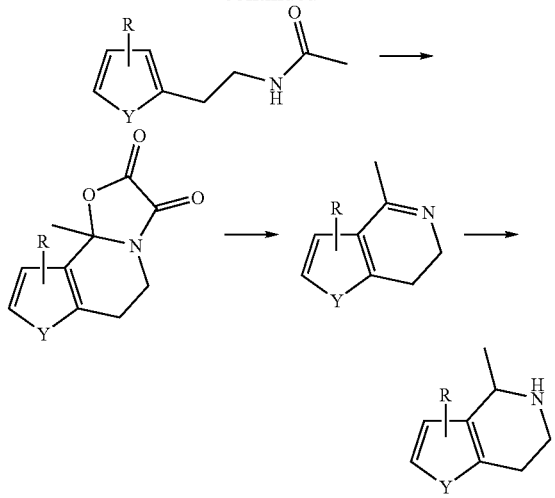

Separation via Chiral Column Chromatography

The racemate of the amino building block 9 is reacted with tert. butyl dicarbonate (Boc$_2$O) in dichloromethane leading to 4-Methyl-6,7-dihydro-4H-thieno[3,2-c]pyridine-5-carboxylic acid tert-butyl ester 2 in good yields. The separation of the boc-protected derivative 10 by preparative HPLC on chiral column Chiralpak AD-H 20×250 leads to the S and R enantiomers 11a and 11b.

The hydrochloride salt is formed by reaction with hydrochloric acid in dioxane at room temperature. The chiral purity of the enantiomers is confirmed by analytical HPLC (Chiralcel OD-H 4.6×250 mm).

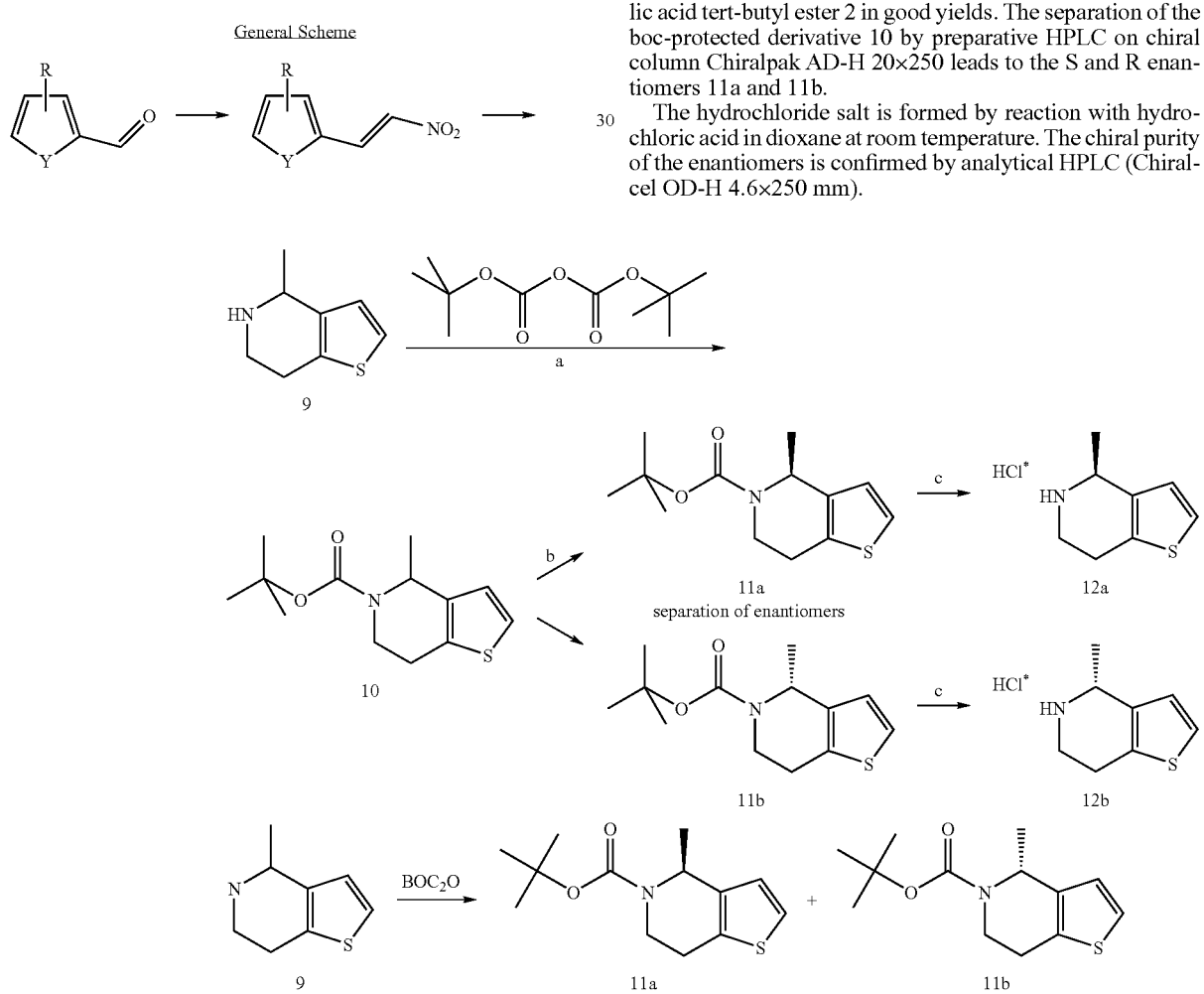

a) Boc$_2$O, DCM; b) chiral HPLC; c) HCl/dioxane.
(S)-4-Methyl-4,5,6,7-tetrahydro-thieno[3,2-c]pyridine (3a) and
(R)-4-Methyl-4,5,6,7-tetrahydro-thieno[3,2-c]pyridine (3b) hydrochlorides.

An amine 9 (624 mg, 4.007 mmol) is dissolved in dry dichloromethane, and Boc$_2$O (1068 mg, 4.9 mmol) is added. The reaction is stirred for 4 hrs at r.t. The reaction is monitored by TLC. When the reaction is over the reaction mixture is washed with 10% solution of K$_2$CO$_3$, with water and a saturated solution of NaCl in separation funnel, dried over Na$_2$SO$_4$, and concentrated under reduced pressure. As a result, 0.469 g of the mixture 11a and 11b is obtained as transparent oil. The isomers are separated by preparative column Chiralpak AD-H 20×250 (particle size 5 μm, eluent hexane/isopropyl alcohol, 95/5, flow speed 10 mL/min, detection by UV 230 nm).

The isomer 11a which has the S-configuration, has been isolated in the amount of 120 mg (~24%; RT 5.143 min; 3-61 mg; ~12%; RT 5.975 min).

Cleavage of Boc-Protective Group:

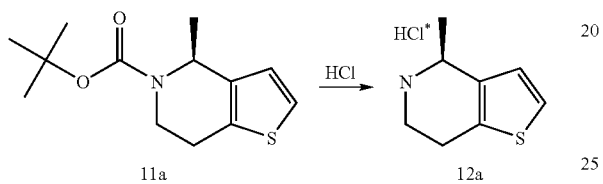

The compound 11a (120 mg) is stirred in dioxane saturated by HCl (content of HCl is 12%) for 3 hrs at r.t., and concentrated under reduced pressure. As a result, 12a having the S-configuration is obtained in the amount of 81 mg (~89% counting on hydrochloride) as white powder.

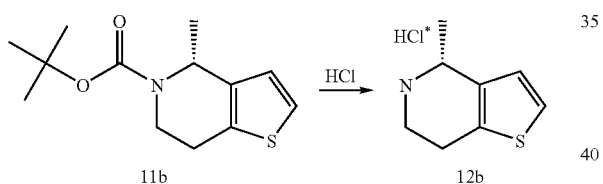

The compound 12b having the R-configuration is synthesized according to the same method as 12a in the amount 43 mg (~93%) (counting on hydrochloride).

General Schemes:

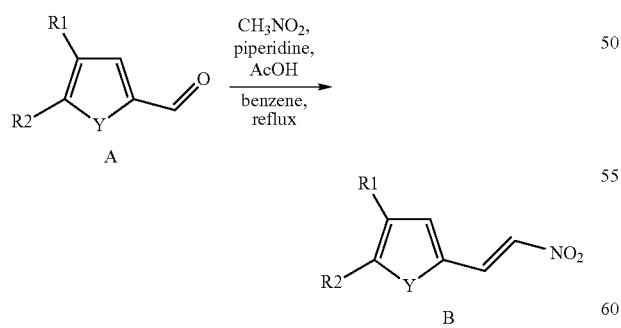

To a solution of aldehyde A (1 mol) in benzene (approx. 20 ml per 1 g of the starting compound) nitromethane (1.2 mol), piperidine (0.1 mol) and acetic acid (0.1 mol) were added. The reaction mixture is refluxed for 2.5 h with azeotrope removing of water. Then, the solvent is evaporated in vacuo. The residue is triturated with cold methanol, filtered, washed with cold methanol that resulted in product crystals in good to moderate yields.

2-Methyl-5-(2-nitro-vinyl)-thiophene

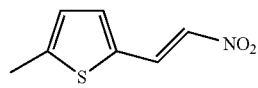

In close analogy to the procedure described above, 5-Methyl-thiophene-2-carbaldehyde is reacted with nitromethane to provide the title compound.

Yield: 76%

LC/MS: m/z=170 (MH$^+$)

4-Methyl-2-(2-nitro-vinyl)-thiophene

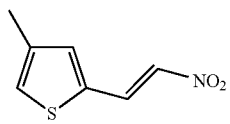

In close analogy to the procedure described above, 4-Methyl-thiophene-2-carbaldehyde is reacted with nitromethane to provide the title compound.

Yield: 78%

LC/MS: m/z=170 (MH$^+$)

2,3-Dimethyl-5-(2-nitro-vinyl)-thiophene

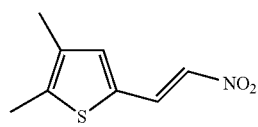

In close analogy to the procedure described above, 2,3-dimethyl-thiophene-2-carbaldehyde is reacted with nitromethane to provide the title compound.

Yield: 58%

LC/MS: m/z=184 (MH$^+$)

2-Methyl-5-(2-nitro-vinyl)-furan

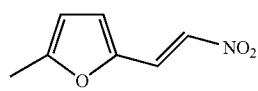

In close analogy to the procedure described above, 5-Methyl-furan-2-carbaldehyde is reacted with nitromethane to provide the title compound.

Yield: 88%

LC/MS: m/z=154 (MH$^+$)

$^1$H NMR (CDCl$_3$) δ: 2.25, 2.39, 4.37-4.40, 4.79, 6.21, 6.81, 7.48, 7.71.

General Scheme:

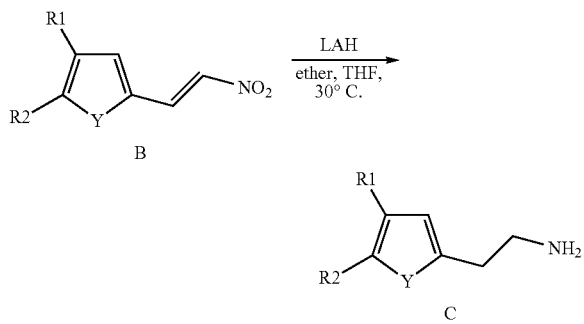

To a suspension of lithium aluminium hydride (2 mol) in diethyl ether (approx. 20 ml per 1 g of LAH) solution of the corresponding nitro derivative B (1 mol) in dry THF is added dropwise at stirring within 30 min. The reaction mixture is stirred at 35° C. for 2 h, and then, cooled with ice water. Then, 20% aqueous NaOH and water (n ml, n ml, 3 n ml per n g LAH) were added step by step carefully. The resulting mixture is stirred for 30 min, filtered and concentrated on rotary evaporator. The residue is purified by flash column chromatography on silica gel (eluent: chloroform/methanol—0→20%) that gave products in good to moderate yields.

2-(5-Methyl-thiophen-2-yl)-ethylamine

In close analogy to the procedure described above, 2-Methyl-5-(2-nitro-vinyl)-thiophene is reacted with lithium aluminium hydride to provide the title compound.
Yield: 85%
LC/MS: m/z=142 (MH$^+$)

2-(4-Methyl-thiophen-2-yl)-ethylamine

In close analogy to the procedure described above, 4-Methyl-2-(2-nitro-vinyl)-thiophene is reacted with lithium aluminium hydride to provide the title compound.
Yield: 85%
LC/MS: m/z=142 (MH$^+$)

2-(4,5-Dimethyl-thiophen-2-yl)-ethylamine

In close analogy to the procedure described above, 2,3-Dimethyl-5-(2-nitro-vinyl)-thiophene is reacted with lithium aluminium hydride to provide the title compound.
Yield: 55%
LC/MS: m/z=156 (MH$^+$)

2-(5-Methyl-furan-2-yl)-ethylamine

In close analogy to the procedure described above, 2-Methyl-5-(2-nitro-vinyl)-furan is reacted with lithium aluminium hydride to provide the title compound.
LC/MS: m/z=126 (MH$^+$)

General Scheme:

To a solution of the amine C (1 mol) in CH$_2$Cl$_2$ (approx. 10 ml per 1 g of the starting compound) triethylamine (1.1 mol) and acetic anhydride (1.2 mol) were added. The reaction mixture is stirred at room temperature for 1 h and concentrated on rotary evaporator. The residue is triturated with hexane, filtered, washed with hexane to give a crystalline compound in good yields.

N-(2-Thiophen-2-yl-ethyl)-acetamide

In close analogy to the procedure described above, 2-Thiophen-2-yl-ethylamine is reacted with acetic anhydride to provide the title compound.
Yield: 90%
LC/MS: m/z=170 (MH$^+$)

N-[2-(5-Methyl-thiophen-2-yl)-ethyl]-acetamide

In close analogy to the procedure described above, 2-(5-Methyl-thiophen-2-yl)-ethylamine is reacted with acetic anhydride to provide the title compound.
Yield: 78%
LC/MS: m/z=184 (MH$^+$)

N-[2-(4-Methyl-thiophen-2-yl)-ethyl]-acetamide

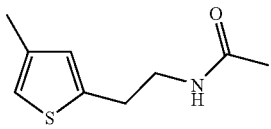

In close analogy to the procedure described above, 2-(4-Methyl-thiophen-2-yl)-ethylamine is reacted with acetic anhydride to provide the title compound.
Yield: 95%
LC/MS: m/z=184 (MH$^+$)

N-[2-(4,5-Dimethyl-thiophen-2-yl)-ethyl]-acetamide

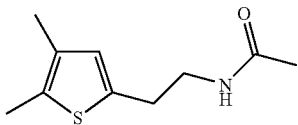

In close analogy to the procedure described above, 2-(4,5-Dimethyl-thiophen-2-yl)-ethylamine is reacted with acetic anhydride to provide the title compound.
Yield: 79%
LC/MS: m/z=198 (MH$^+$)

N-(2-Furan-2-yl-ethyl)-acetamide

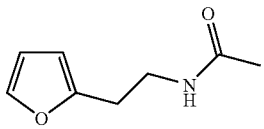

In close analogy to the procedure described above, 2-Furan-2-yl-ethylamine is reacted with acetic anhydride to provide the title compound.
Yield: 41%
LC/MS: m/z=154 (MH$^+$)
$^1$H NMR (CDCl$_3$) δ: 2.05, 2.85, 3.53, 5.68, 6.07, 6.31, 7.34

2,2,2-Trifluoro-N-(2-thiophen-2-yl-ethyl)-acetamide

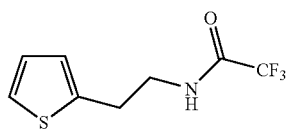

In close analogy to the procedure described above, 2-Thiophen-2-yl-ethylamine is reacted with ethyl trifluoracetate to provide the title compound.
Yield: 86%
LC/MS: m/z=224 (MH$^+$)

N-[2-(5-Methyl-furan-2-yl)-ethyl]-acetamide

In close analogy to the procedure described above, 2-(5-Methyl-furan-2-yl)-ethylamine is reacted with acetic anhydride to provide the title compound.
Yield: 55%
LC/MS: m/z=167 (MH$^+$)
$^1$H NMR (d$_6$-DMSO) δ: 1.97, 2.26, 2.78, 3.51, 5.62, 5.86, 5.94

General Scheme:

To a solution of the amide D (1 mol) in toluene (approx. 10 ml per 1 g of the starting compound) phosphorus pentoxide (approx. 1.5 g per 1 g of the starting compound) and phosphorus oxychloride (2-3 mol) were added. The reaction mixture is refluxed for 3 h and cooled to 0° C. Some ice is carefully added to the reaction mixture, and it is stirred for 1 h. Then, the mixture is filtered. The organic layer is separated and washed with water. The combined aqueous layers were washed with benzene, then alkalified with 25% sodium hydroxide, extracted with benzene, dried over Na$_2$SO$_4$ and concentrated on rotary evaporator. Resulting oil is used in the next step without purification.

4-Methyl-6,7-dihydro-thieno[3,2-c]pyridine

In close analogy to the procedure described above, N-(2-Thiophen-2-yl-ethyl)-acetamide is reacted with phosphorus pentoxide to provide the title compound.
LC/MS: m/z=152 (MH$^+$)

2,4-Dimethyl-6,7-dihydro-thieno[3,2-c]pyridine

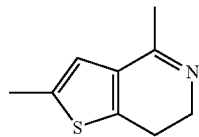

In close analogy to the procedure described above, N-[2-(5-Methyl-thiophen-2-yl)-ethyl]-acetamide is reacted with phosphorus pentoxide to provide the title compound.

LC/MS: m/z=166 (MH$^+$)

3,4-Dimethyl-6,7-dihydro-thieno[3,2-c]pyridine

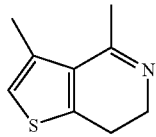

In close analogy to the procedure described above, N-[2-(4-Methyl-thiophen-2-yl)-ethyl]-acetamide is reacted with phosphorus pentoxide to provide the title compound.

LC/MS: m/z=167 (MH$^+$)

2,3,4-Trimethyl-6,7-dihydro-thieno[3,2-c]pyridine

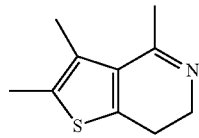

In close analogy to the procedure described above, N-[2-(4,5-Dimethyl-thiophen-2-yl)-ethyl]-acetamide is reacted with phosphorus pentoxide to provide the title compound.

LC/MS: m/z=180 (MH$^+$)

4-Methyl-6,7-dihydro-furo[3,2-c]pyridine

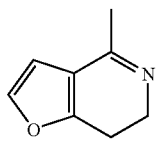

In close analogy to the procedure described above, N-(2-Furan-2-yl-ethyl)-acetamide is reacted with phosphorus pentoxide to provide the title compound.

Yield: 94%

LC/MS: m/z=136 (MH$^+$)

4-Methyl-6,7-dihydro-thieno[3,2-c]pyridine

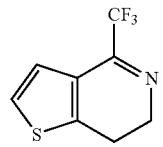

In close analogy to the procedure described above, 2,2,2-Trifluoro-N-(2-thiophen-2-yl-ethyl)-acetamide is reacted with phosphorus pentoxide to provide the title compound.

Yield: 25%

LC/MS: m/z=206 (MH$^+$)

2,4-Dimethyl-6,7-dihydro-furo[3,2-c]pyridine

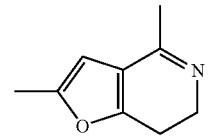

In close analogy to the procedure described above, N-[2-(5-Methyl-furan-2-yl)-ethyl]-acetamide is reacted with phosphorus pentoxide to provide the title compound.

LC/MS: m/z=150 (MH$^+$)

$^1$H NMR (CDCl$_3$) δ: 2.18, 2.30, 2.70, 3.84, 3.88, 6.01.

General Scheme:

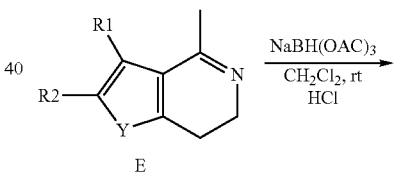

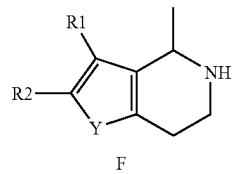

To a solution of compound E (1 mol) in CH$_2$Cl$_2$ (approx. 20 ml per 1 g of the starting compound) sodium triacetoxyborohydride (1.5 mol) is added. The reaction mixture is stirred for 12 h at room temperature. The reaction mixture is poured into saturated sodium bicarbonate solution and stirred for 30 min. The organic layer is separated, and aqueous layer is extracted with chloroform. The combined organic phases were dried over Na$_2$SO$_4$ and concentrated on rotary evaporator. The residue is purified by flash column chromatography on silica gel (eluent: chloroform/methanol—0→20%) to give yellowish oil. Then, 6 N isopropanolic HCl is added to the oil, stirred for 5 min, concentrated on rotary evaporator, triturated with diethyl ether, filtered off, washed with ether and dried in vacuo to give crystalline compound in acceptable yields on 2 steps.

4-Methyl-4,5,6,7-tetrahydro-thieno[3,2-c]pyridine

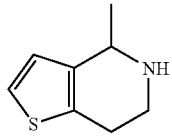

In close analogy to the procedure described above, 4-Methyl-6,7-dihydro-thieno[3,2-c]pyridine is reacted with sodium triacetoxyborohydride to provide the title compound.
Yield: 22% for two steps
LC/MS: m/z=155 (MH$^+$)
$^1$H NMR (d$_6$-DMSO) δ: 1.59, 2.95-3.57, 4.49-4.52, 6.99, 7.42, 9.70.

2,4-Dimethyl-4,5,6,7-tetrahydro-thieno[3,2-c]pyridine

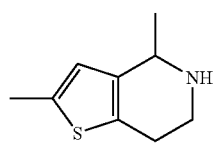

In close analogy to the procedure described above, 2,4-Dimethyl-6,7-dihydro-thieno[3,2-c]pyridine is reacted with sodium triacetoxyborohydride to provide the title compound.
Yield: 14% for two steps
LC/MS: m/z=169 (MH$^+$)
$^1$H NMR (d$_6$-DMSO) δ: 1.51, 2.48, 2.83-3.55, 6.65, 9.62.

3,4-Dimethyl-4,5,6,7-tetrahydro-thieno[3,2-c]pyridine

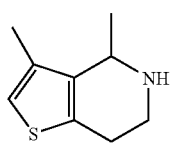

In close analogy to the procedure described above, 3,4-Dimethyl-6,7-dihydro-thieno[3,2-c]pyridine is reacted with sodium triacetoxyborohydride to provide the title compound.
Yield: 8% for two steps
LC/MS: m/z=169 (MH$^+$)

2,3,4-Trimethyl-4,5,6,7-tetrahydro-thieno[3,2-c]pyridine

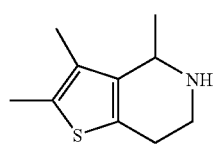

In close analogy to the procedure described above, 2,3,4-Trimethyl-6,7-dihydrothieno[3,2-c]pyridine is reacted with sodium triacetoxyborohydride to provide the title compound.
Yield: 14% for two steps
LC/MS: m/z=183 (MH$^+$)
$^1$H NMR (d$_6$-DMSO) δ: 1.68, 2.00, 2.28, 2.89-3.60, 4.50-4.61, 10.09

4-Methyl-4,5,6,7-tetrahydro-furo[3,2-c]pyridine

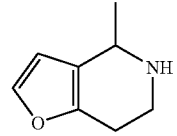

In close analogy to the procedure described above, 4-Methyl-6,7-dihydro-furo[3,2-c]pyridine is reacted with sodium triacetoxyborohydride to provide the title compound.
LC/MS: m/z=138 (MH$^+$)

4-Methyl-4,5,6,7-tetrahydro-thieno[3,2-c]pyridine

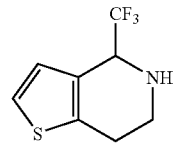

In close analogy to the procedure described above, 4-Methyl-6,7-dihydro-thieno[3,2-c]pyridine is reacted with sodium triacetoxyborohydride to provide the title compound.
Yield: 25%
LC/MS: m/z=206 (MH$^+$)

2,4-Dimethyl-4,5,6,7-tetrahydro-furo[3,2-c]pyridine

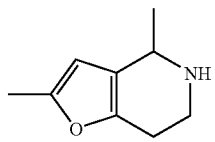

In close analogy to the procedure described above, 2,4-Dimethyl-6,7-dihydro-furo[3,2-c]pyridine is reacted with sodium triacetoxyborohydride to provide the title compound.
Yield: 45% for two steps
LC/MS: m/z=151 (MH$^+$)

2-(2-Isocyanato-propyl)-thiophene

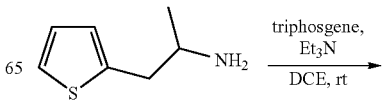

-continued

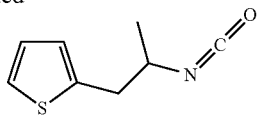

To a solution of 1-methyl-2-thiophen-2-ylethylamine (2 g, 14.2 mmol) in dichloroethane (30 ml) triethylamine (4.3 g, 42.6 mmol) and triphosgene (2.1 g, 7.1 mmol) were added. The reaction mixture stirred for 1 h and concentrated on rotary evaporator. Diethyl ether is added, and the resulting mixture is filtered. Ether solution is concentrated, and the resulting oil is used in the next step without purification.

6-Methyl-6,7-dihydro-5H-thieno[3,2-c]pyridin-4-one

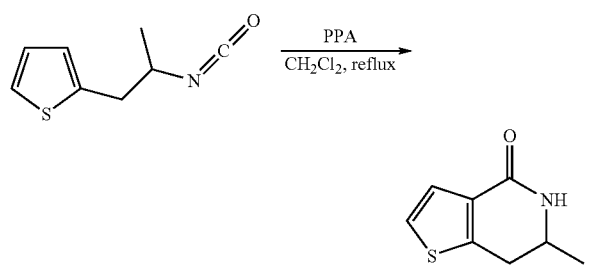

To PPA (15 ml) a solution of 2-(2-isocyanatopropyl)-thiophene in CH$_2$Cl$_2$ (15 ml) was added. The reaction mixture was stirred under reflux for 3 h, cooled, poured into ice and alkalified with concentrated ammonia. Then, the mixture was extracted with chloroform, dried over Na$_2$SO$_4$ and concentrated on rotary evaporator. The residue was purified by flash column chromatography on silica gel (eluent: chloroform/acetone—0→30%) to give 0.5 g of the target compound as a white solid.

Yield: 22% for two steps
LC/MS: m/z=168 (MH$^+$)

6-Methyl-4,5,6,7-tetrahydro-thieno[3,2-c]pyridine

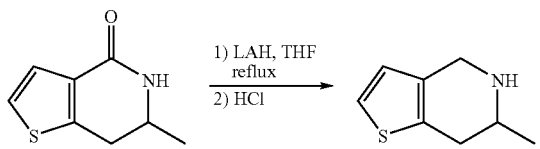

To a suspension of LAH (0.38 g, 10 mmol) in THF (10 ml) a solution of 6-methyl-6,7-dihydro-5H-thieno[3,2-c]pyridin-4-one (0.5 g, 3 mmol) in THF (10 ml) was added dropwise. The mixture was stirred for 3 h under reflux and cooled to 0° C. with ice. The solution of 0.4 ml of water in 2 ml THF, 25% NaOH (0.4 ml) and water (1.2 ml) were added carefully step by step. The mixture was stirred for 30 min, filtered and concentrated on rotary evaporator. The residue was purified by flash column chromatography on silica gel (eluent: chloroform/methanol—0→20%) to give yellowish oil. Then, 6 N isopropanolic HCl was added to the oil, stirred for 5 min, concentrated on rotary evaporator, triturated with diethyl ether, filtered, washed with ether and dried in vacuo to give 0.37 g of crystalline compound.

Yield: 67%
LC/MS: m/z=155 (MH$^+$)
$^1$H NMR (d$_6$-DMSO) δ: 1.40, 2.76-3.19, 3.49-3.65, 4.08-4.37, 6.93, 7.44, 9.69.

The following compounds according to the invention are prepared as examples, which are intended as an illustration of and not a limitation upon the scope of the invention:

Example 1

6-Bromo-2-[(4-methyl-6,7-dihydrothieno[3,2-c]pyridin-5(4H)-yl)carbonyl]pyrazolo[1,5-a]pyrimidine

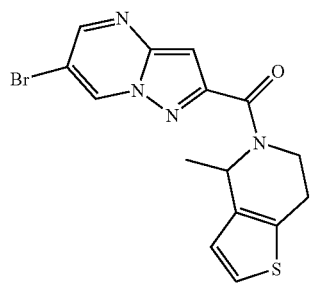

To a solution of 6-bromo-pyrazolo[1,5-a]pyrimidine-2-carboxylic acid (0.7 g, 2.9 mmol, 1.0 equiv) and TBTU (1.0 g, 3.1 mmol, 1.1 equiv) in dry acetonitrile (20 mL), triethylamine (1 mL, 7.25 mmol, 2.5 equiv) and 4-methyl-4,5,6,7-tetrahydro-thieno[3,2-c]pyridine (0.45 g, 2.9 mmol, 1 equiv) are added. The reaction mixture is stirred at 50° C. for 2 h and then at room temperature for 8 h. The reaction mixture is diluted with water (10 ml). The precipitate is filtered, washed sequentially with 50% aqueous ethanol, water, 5% aqueous ammonia, and diethyl ether, and then dried to provide 0.524 g of the title compound.

Yield: 48%
LC/MS: m/z=377 (MH$^+$)
$^1$H NMR (d$_6$-DMSO) δ: 1.46, 2.70-3.00, 3.32-3.52, 4.37, 4.65-4.82, 5.18-5.33, 5.57, 6.70-7.10, 7.20-7.40, 8.66, 9.53.

The stereo-isomers of this compound are separated. The S-configurated compound has a different activity than the R-configurated compound.

Example 2

(6-Chloro-pyrazolo[1,5-a]pyrimidin-2-yl)-(4-methyl-6,7-dihydro-4H-thieno[3,2-c]pyridin-5-yl)-methanone

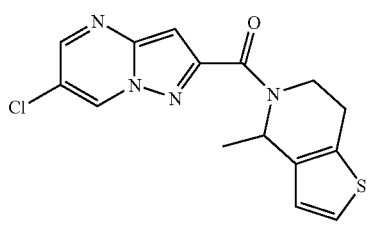

In close analogy to the procedure described in Example 1, 6-chloro-pyrazolo[1,5-a]pyrimidine-2-carboxylic acid is reacted with 4-Methyl-4,5,6,7-tetrahydro-thieno[3,2-c]pyridine to provide the title compound.

Yield: 57%

LC/MS: m/z=333 (MH+)

¹H NMR (d₆-DMSO) δ: 1.46, 2.70-3.00, 3.32-3.52, 4.37, 4.65-4.82, 5.18-5.33, 5.57, 6.70-7.10, 7.20-7.40, 8.66, 9.53.

The stereo-isomers of this compound are separated. The S-configurated compound has a different activity than the R-configurated compound.

Example 3

(6-Chloro-pyrazolo[1,5-a]pyrimidin-2-yl)-(6,7-dihydro-4H-thieno[3,2-c]pyridin-5-yl)-methanone

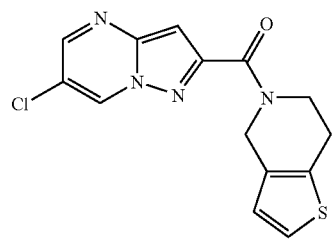

In close analogy to the procedure described in Example 1, 6-chloro-pyrazolo[1,5-a]pyrimidine-2-carboxylic acid is reacted with 4,5,6,7-tetrahydro-thieno[3,2-c]pyridine to provide the title compound in moderate yield.

LC/MS: m/z=320 (MH+)

Example 4

(6-Bromo-pyrazolo[1,5-a]pyrimidin-2-yl)-(6,7-dihydro-4H-thieno[3,2-c]pyridin-5-yl)-methanone

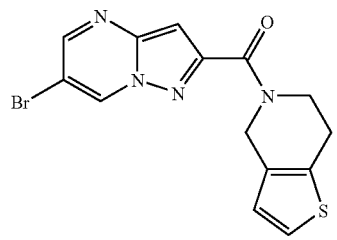

In close analogy to the procedure described in Example 1, 6-bromo-pyrazolo[1,5-a]pyrimidine-2-carboxylic acid is reacted with 4,5,6,7-tetrahydro-thieno[3,2-c]pyridine to provide the title compound in moderate yield.

LC/MS: m/z=364 (MH+)

Example 5

(6-Chloro-pyrazolo[1,5-a]pyrimidin-2-yl)-(4,4-dimethyl-6,7-dihydro-4H-thieno[3,2-c]pyridin-5-yl)-methanone

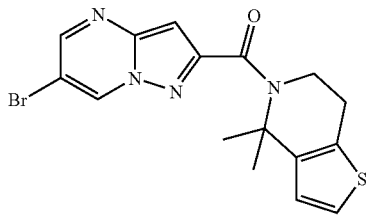

In close analogy to the procedure described in Example 1, 6-chloro-pyrazolo[1,5-a]pyrimidine-2-carboxylic acid is reacted with 4,4-dimethyl-4,5,6,7-tetrahydro-thieno[3,2-c]pyridine to provide the title compound in moderate yield.

LC/MS: m/z=348 (MH+)

Example 6

(6-Bromo-pyrazolo[1,5-a]pyrimidin-2-yl)-(4,4-dimethyl-6,7-dihydro-4H-thieno[3,2-c]pyridin-5-yl)-methanone

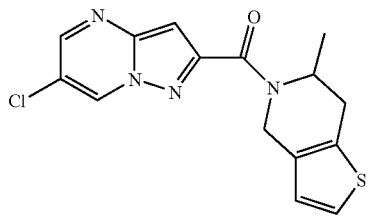

In close analogy to the procedure described in Example 1, 6-chloro-pyrazolo[1,5-a]pyrimidine-2-carboxylic acid is reacted with 4,4-dimethyl-4,5,6,7-tetrahydro-thieno[3,2-c]pyridine to provide the title compound in moderate yield.

LC/MS: m/z=392 (MH+)

Example 7

(6-Chloro-pyrazolo[1,5-a]pyrimidin-2-yl)-(6-methyl-6,7-dihydro-4H-thieno[3,2-c]pyridin-5-yl)-methanone In close analogy to the procedure described in Example 1, 6-chloro-pyrazolo[1,5-a]pyrimidine-2-carboxylic acid is reacted with 6-methyl-4,5,6,7-tetrahydro-thieno[3,2-c]pyridine to provide the title compound.

Yield: 51%

LC/MS: m/z=333 (MH+)

$^1$H NMR (d$_6$-DMSO) δ: 1.10-1.25, 2.60-2.85, 3.00-3.15, 4.05-4.50, 4.70-5.40, 6.70-7.10, 7.22-7.42, 8.66, 9.54.

The stereo-isomers of this compound are separated. The S-configured compound has a different activity than the R-configured compound.

Example 8

(6-Bromo-pyrazolo[1,5-a]pyrimidin-2-yl)-(6-methyl-6,7-dihydro-4H-thieno[3,2-c]pyridin-5-yl)-methanone In close analogy to the procedure described in Example 1, 6-bromo-pyrazolo[1,5-a]pyrimidine-2-carboxylic acid is reacted with 6-Methyl-4,5,6,7-tetrahydro-thieno[3,2-c]pyridine to provide the title compound.

Yield: 62%

LC/MS: m/z=378 (MH+)

$^1$H NMR (d$_6$-DMSO) δ: 1.10-1.27, 2.60-2.90, 3.00-3.20, 4.05-4.50, 4.70-5.40, 6.70-7.10, 7.22-7.42, 8.68, 9.60.

The stereo-isomers of this compound are separated. The S-configured compound has a different activity than the R-configured compound.

Example 9

(6-Bromo-pyrazolo[1,5-a]pyrimidin-2-yl)-(4-ethyl-6,7-dihydro-4H-thieno[3,2-c]pyridin-5-yl)-methanone In close analogy to the procedure described in Example 1, 6-bromo-pyrazolo[1,5-a]pyrimidine-2-carboxylic acid is reacted with 4-ethyl-4,5,6,7-tetrahydro-thieno[3,2-c]pyridine to provide the title compound.

Yield: 79%

LC/MS: m/z=392 (MH$^+$)

$^1$H NMR (d$_6$-DMSO) δ: 0.98, 1.70-2.00, 2.70-3.00, 3.36-3.51, 4.25-4.37, 5.50-5.62, 6.70-7.10, 7.25-7.38, 8.67, 9.59.

The stereo-isomers of this compound are separated. The S-configured compound has a different activity than the R-configured compound.

Example 10

(6-Chloro-pyrazolo[1,5-a]pyrimidin-2-yl)-(4-ethyl-6,7-dihydro-4H-thieno[3,2-c]pyridin-5-yl)-methanone In close analogy to the procedure described in Example 1, 6-chloro-pyrazolo[1,5-a]pyrimidine-2-carboxylic acid is reacted with 4-ethyl-4,5,6,7-tetrahydro-thieno[3,2-c]pyridine to provide the title compound.

Yield: 60%

LC/MS: m/z=347 (MH$^+$)

$^1$H NMR (d$_6$-DMSO) δ: 0.98, 1.70-2.00, 2.70-3.00, 3.37-3.52, 4.25-4.37, 5.50-5.62, 6.70-7.10, 7.23-7.37, 8.66, 9.56.

The stereo-isomers of this compound are separated. The S-configured compound has a different activity than the R-configured compound.

Example 11

(6-Bromo-pyrazolo[1,5-a]pyrimidin-2-yl)-(4-trifluoromethyl-6,7-dihydro-4H-thieno[3,2-c]pyridin-5-yl)-methanone In close analogy to the procedure described in Example 1, 6-bromo-pyrazolo[1,5-a]pyrimidine-2-carboxylic acid is reacted with 4-trifluoromethyl-4,5,6,7-tetrahydrothieno[3,2-c]pyridine to provide the title compound in moderate yield.

LC/MS: m/z=378 (MH$^+$)

The stereo-isomers of this compound are separated. The S-configured compound has a different activity than the R-configured compound.

Example 12

(6-Chloro-pyrazolo[1,5-a]pyrimidin-2-yl)-(4-trifluoromethyl-6,7-dihydro-4H-thieno[3,2-c]pyridin-5-yl)-methanone

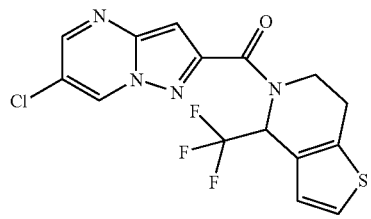

In close analogy to the procedure described in Example 1, 6-chloro-pyrazolo[1,5a]pyrimidine-2-carboxylic acid is reacted with 4-Trifluoromethyl-4,5,6,7-tetrahydro-thieno[3,2-c]pyridine to provide the title compound.
Yield: 28%
LC/MS: m/z=387 (MH+)
$^1$H NMR (d$_6$-DMSO) δ: 2.85-3.12, 3.48-3.63, 4.58-4.72, 6.30-6.45, 7.00-7.20, 7.43-7.55, 8.70, 9.58.

The stereo-isomers of this compound are separated. The S-configurated compound has a different activity than the R-configurated compound.

Example 13

6-Bromo-pyrazolo[1,5-a]pyrimidin-2-yl)-(6,6-dimethyl-6,7-dihydro-4H-thieno[3,2-c]pyridin-5-yl)-methanone

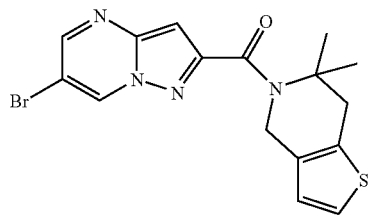

In close analogy to the procedure described in Example 1, 6-bromo-pyrazolo[1,5-a]pyrimidine-2-carboxylic acid is reacted with 6,6-dimethyl-4,5,6,7-tetrahydro-thieno[3,2-c]pyridine to provide the title compound in moderate yield.
LC/MS: m/z=392 (MH+)

Example 14

6-Chloro-pyrazolo[1,5-a]pyrimidin-2-yl)-(6,6-dimethyl-6,7-dihydro-4H-thieno[3,2-c]pyridin-5-yl)-methanone

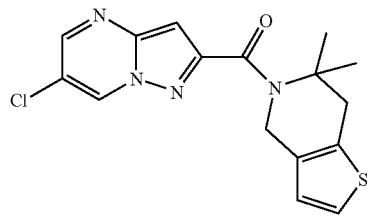

In close analogy to the procedure described in Example 1, 6-chloro-pyrazolo[1,5-a]pyrimidine-2-carboxylic acid is reacted with 6,6-dimethyl-4,5,6,7-tetrahydro-thieno[3,2-c]pyridine to provide the title compound in moderate yield.
LC/MS: m/z=348 (MH+)

Example 15

(6-Bromo-pyrazolo[1,5-a]pyrimidin-2-yl)-(2,4-dimethyl-6,7-dihydro-4H-thieno[3,2-c]pyridin-5-yl)-methanone

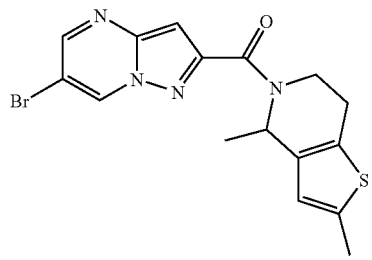

In close analogy to the procedure described in Example 1, 6-bromo-pyrazolo[1,5-a]pyrimidine-2-carboxylic acid is reacted with 2,4-dimethyl-4,5,6,7-tetrahydro-thieno[3,2-c]pyridine to provide the title compound.
Yield: 40%
LC/MS: m/z=392 (MH+)
$^1$H NMR (d$_6$-DMSO) δ: 1.41, 2.36, 2.60-2.95, 3.32-3.47, 4.25-4.37, 5.40-5.52), 6.64, 7.00, 8.68, 9.58.

The stereo-isomers of this compound are separated. The S-configurated compound has a different activity than the R-configurated compound.

Example 16

(6-Chloro-pyrazolo[1,5-a]pyrimidin-2-yl)-(2,4-dimethyl-6,7-dihydro-4H-thieno[3,2-c]pyridin-5-yl)-methanone

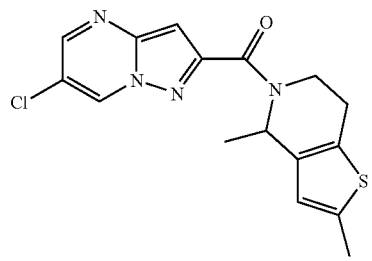

In close analogy to the procedure described in Example 1, 6-chloro-pyrazolo[1,5-a]pyrimidine-2-carboxylic acid is reacted with 2,4-dimethyl-4,5,6,7-tetrahydro-thieno[3,2-c]pyridine to provide the title compound.
Yield: 46%
LC/MS: m/z=347 (MH+)
$^1$H NMR (d$_6$-DMSO) δ: 1.41, 2.36, 2.60-2.95, 3.30-3.45, 4.25-4.37, 5.40-5.52, 6.65, 7.02, 8.66, 9.55.

The stereo-isomers of this compound are separated. The S-configurated compound has a different activity than the R-configurated compound.

Example 17

(6-Bromo-pyrazolo[1,5-a]pyrimidin-2-yl)-(3,4-dimethyl-6,7-dihydro-4H-thieno[3,2-c]pyridin-5-yl)-methanone

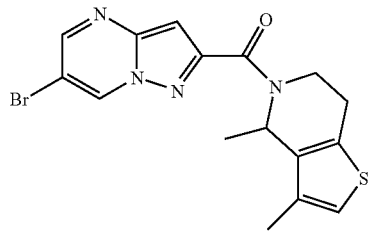

In close analogy to the procedure described in Example 1, 6-bromo-pyrazolo[1,5-a]pyrimidine-2-carboxylic acid is reacted with 2,5-dimethyl-4,5,6,7-tetrahydro-thieno[3,2-c]pyridine to provide the title compound.

Yield: 71%

LC/MS: m/z=392 (MH$^+$)

$^1$H NMR (d$_6$-DMSO) δ: 1.41, 2.16, 2.70-3.00, 3.42-3.55, 4.25-4.37, 5.46-5.59), 6.86-7.10, 8.68, 9.59.

The stereo-isomers of this compound are separated. The S-configurated compound has a different activity than the R-configurated compound.

Example 18

6-Bromo-2-[(2,3,4-trimethyl-6,7-dihydrothieno[3,2-c]pyridin-5(4H)-yl)carbonyl]-pyrazolo[1,5-a]pyrimidine

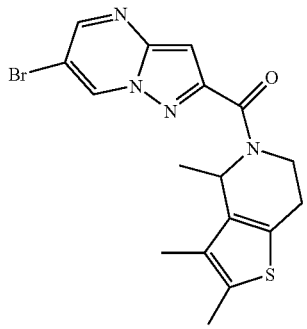

In close analogy to the procedure described in Example 1, 6-bromo-pyrazolo[1,5-a]pyrimidine-2-carboxylic acid is reacted with 2,3,4-Trimethyl-4,5,6,7-tetrahydrothieno[3,2-c]pyridine to provide the title compound.

Yield: 64%

LC/MS: m/z=406 (MH+)

$^1$H NMR (d$_6$-DMSO) δ: 1.39, 2.02, 2.24, 2.60-2.95, 3.41-3.55, 4.20-4.35, 5.40-5.52, 7.00, 8.68, 9.58.

The stereo-isomers of this compound are separated. The S-configurated compound has a different activity than the R-configurated compound.

Example 19

6-Chloro-2-[(2,3,4-trimethyl-6,7-dihydrothieno[3,2-c]pyridin-5(4H)-yl)carbonyl]-pyrazolo[1,5-a]pyrimidine

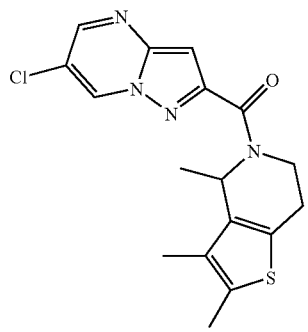

In close analogy to the procedure described in Example 1, 6-chloro-pyrazolo[1,5-a]pyrimidine-2-carboxylic acid is reacted with 2,3,4-Trimethyl-4,5,6,7-tetrahydrothieno[3,2-c]pyridine to provide the title compound.

Yield: 57%

LC/MS: m/z=361 (MH$^+$)

$^1$H NMR (d$_6$-DMSO) δ: 1.40, 2.01, 2.23, 2.60-2.95, 3.41-3.55, 4.20-4.35, 5.40-5.52, 7.01, 8.66, 9.53.

The stereo-isomers of this compound are separated. The S-configurated compound has a different activity than the R-configurated compound.

Example 20

(6-Bromo-pyrazolo[1,5-a]pyrimidin-2-yl)-(2-fluoro-4-methyl-6,7-dihydro-4H-thieno[3,2-c]pyridin-5-yl)-methanone

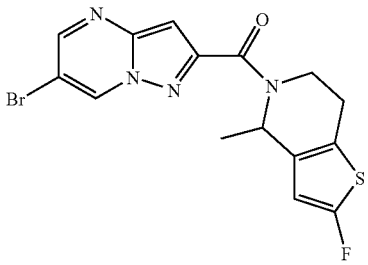

In close analogy to the procedure described in Example 1, 6-bromo-pyrazolo[1,5-a]pyrimidine-2-carboxylic acid is reacted with 2-fluoro-4-methyl-4,5,6,7-tetrahydrothieno[3,2-c]pyridine to provide the title compound in moderate yield.

LC/MS: m/z=396 (MH$^+$)

The stereo-isomers of this compound are separated. The S-configurated compound has a different activity than the R-configurated compound.

Example 21

(6-Chloro-pyrazolo[1,5-a]pyrimidin-2-yl)-(2-fluoro-4-methyl-6,7-dihydro-4H-thieno[3,2-c]pyridin-5-yl)-methanone

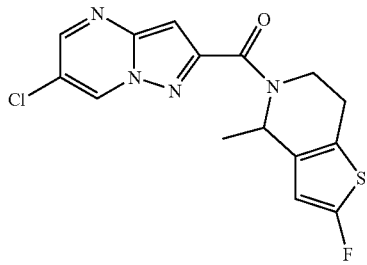

In close analogy to the procedure described in Example 1, 6-chloro-pyrazolo[1,5-a]pyrimidine-2-carboxylic acid is reacted with 2-fluoro-4-methyl-4,5,6,7-tetrahydrothieno[3,2-c]pyridine to provide the title compound in moderate yield.

LC/MS: m/z=352 (MH$^+$)

The stereo-isomers of this compound are separated. The S-configurated compound has a different activity than the R-configurated compound.

Example 22

(6-Bromo-pyrazolo[1,5-a]pyrimidin-2-yl)-(3-fluoro-4-methyl-6,7-dihydro-4H-thieno[3,2-c]pyridin-5-yl)-methanone

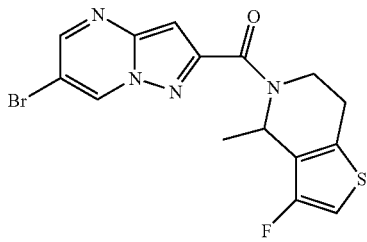

In close analogy to the procedure described in Example 1, 6-bromo-pyrazolo[1,5-a]pyrimidine-2-carboxylic acid is reacted with 3-fluoro-4-methyl-4,5,6,7-tetrahydrothieno[3,2-c]pyridine to provide the title compound in moderate yield.

LC/MS: m/z=396 (MH$^+$)

The stereo-isomers of this compound are separated. The S-configurated compound has a different activity than the R-configurated compound.

Example 23

(6-Chloro-pyrazolo[1,5-a]pyrimidin-2-yl)-(3-fluoro-4-methyl-6,7-dihydro-4H-thieno[3,2-c]pyridin-5-yl)-methanone

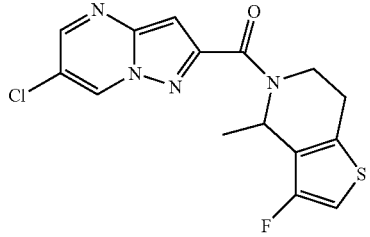

In close analogy to the procedure described in Example 1, 6-chloro-pyrazolo[1,5-a]pyrimidine-2-carboxylic acid is reacted with 3-fluoro-4-methyl-4,5,6,7-tetrahydrothieno[3,2-c]pyridine to provide the title compound in moderate yield.

LC/MS: m/z=352 (MH$^+$)

The stereo-isomers of this compound are separated. The S-configurated compound has a different activity than the R-configurated compound.

Example 24

(6-Bromo-pyrazolo[1,5-a]pyrimidin-2-yl)-(2,3-difluoro-4-methyl-6,7-dihydro-4H-thieno[3,2-c]pyridin-5-yl)-methanone

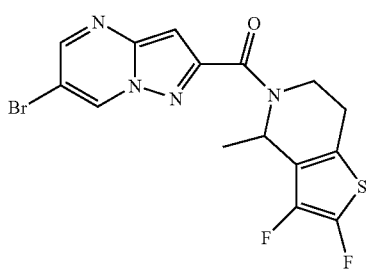

In close analogy to the procedure described in Example 1, 6-bromo-pyrazolo[1,5-a]pyrimidine-2-carboxylic acid is reacted with 2,3-difluoro-4-methyl-4,5,6,7-tetrahydrothieno[3,2-c]pyridine to provide the title compound in moderate yield.

LC/MS: m/z=414 (MH$^+$)

The stereo-isomers of this compound are separated. The S-configurated compound has a different activity than the R-configurated compound.

Example 25

(6-Chloro-pyrazolo[1,5-a]pyrimidin-2-yl)-(2,3-difluoro-4-methyl-6,7-dihydro-4H-thieno[3,2-c]pyridin-5-yl)-methanone

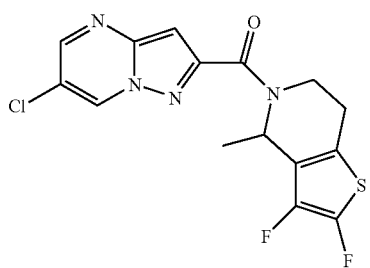

In close analogy to the procedure described in Example 1, 6-chloro-pyrazolo[1,5-a]pyrimidine-2-carboxylic acid is reacted with 2,3-difluoro-4-methyl-4,5,6,7-tetrahydrothieno[3,2-c]pyridine to provide the title compound in moderate yield.

LC/MS: m/z=370 (MH+)

The stereo-isomers of this compound are separated. The S-configurated compound has a different activity than the R-configurated compound.

Example 26

(6-Bromo-pyrazolo[1,5-a]pyrimidin-2-yl)-(4-methyl-2-trifluoromethyl-6,7-dihydro-4H-thieno[3,2-c]pyridin-5-yl)-methanone

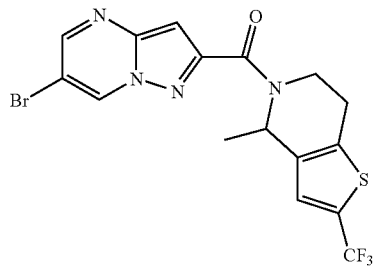

In close analogy to the procedure described in Example 1, 6-bromo-pyrazolo[1,5-a]pyrimidine-2-carboxylic acid is reacted with 4-methyl-2-trifluoromethyl-4,5,6,7-tetrahydrothieno[3,2-c]pyridine to provide the title compound in moderate yield.

LC/MS: m/z=392 (MH+). The stereo-isomers of this compound are separated. The S-configurated compound has a different activity than the R-configurated compound.

Example 27

(6-Chloro-pyrazolo[1,5-a]pyrimidin-2-yl)-(4-methyl-2-trifluoromethyl-6,7-dihydro-4H-thieno[3,2-c]pyridin-5-yl)-methanone

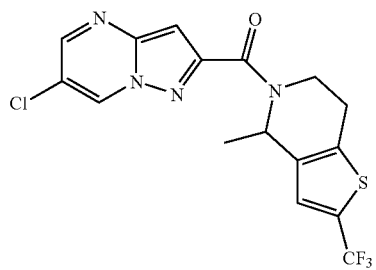

In close analogy to the procedure described in Example 1, 6-chloro-pyrazolo[1,5-a]pyrimidine-2-carboxylic acid is reacted with 4-methyl-2-trifluoromethyl-4,5,6,7-tetrahydrothieno[3,2-c]pyridine to provide the title compound in moderate yield.

LC/MS: m/z=348 (MH+)

Example 28

6-Bromo-2-[(4-methyl-6,7-dihydrofuro[3,2-c]pyridin-5(4H)-yl)carbonyl]pyrazolo[1,5-a]pyrimidine

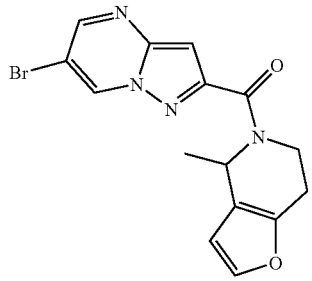

In close analogy to the procedure described in Example 1, 6-bromo-pyrazolo[1,5-a]pyrimidine-2-carboxylic acid is reacted with 4-Methyl-4,5,6,7-tetrahydro-furo[3,2-c]pyridine to provide the title compound.

Yield: 39%

LC/MS: m/z=362 (MH+)

$^1$H NMR (d$_6$-DMSO) δ: 1.40, 2.52-2.93, 3.33-3.53, 4.31, 5.38-5.53, 6.45, 7.02, 7.40-7.55, 8.68, 9.59.

The stereo-isomers of this compound are separated. The S-configurated compound has a different activity than the R-configurated compound.

Example 29

6-Chloro-2-[(4-methyl-6,7-dihydrofuro[3,2-c]pyridin-5(4H)-yl)carbonyl]pyrazolo[1,5-a]pyrimidine

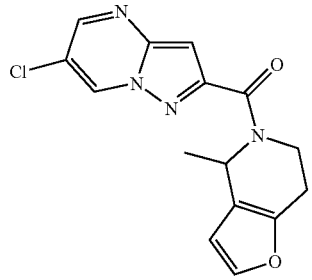

In close analogy to the procedure described in Example 1, 6-chloro-pyrazolo[1,5-a]pyrimidine-2-carboxylic acid is reacted with 4-Methyl-4,5,6,7-tetrahydro-furo[3,2-c]pyridine to provide the title compound.

Yield: 49%

LC/MS: m/z=317 (MH+)

$^1$H NMR (d$_6$-DMSO) δ: 1.41, 2.50-2.90, 3.30-3.55, 4.31, 5.45, 6.46, 7.02, 7.40-7.60, 8.66, 9.55.

The stereo-isomers of this compound are separated. The S-configurated compound has a different activity than the R-configurated compound.

Example 30

(6-Chloro-pyrazolo[1,5-a]pyrimidin-2-yl)-(6,7-dihydro-4H-furo[3,2-c]pyridin-5-yl)-methanone

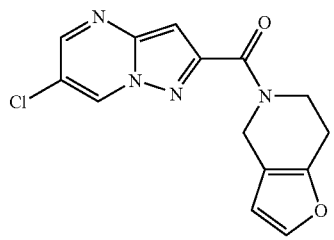

In close analogy to the procedure described in Example 1, 6-chloro-pyrazolo[1,5-a]pyrimidine-2-carboxylic acid is reacted with 4,5,6,7-tetrahydro-furo[3,2-c]pyridine to provide the title compound in moderate yield.
LC/MS: m/z=304 (MH$^+$)

Example 31

(6-Bromo-pyrazolo[1,5-a]pyrimidin-2-yl)-(6,7-dihydro-4H-furo[3,2-c]pyridin-5-yl)-methanone

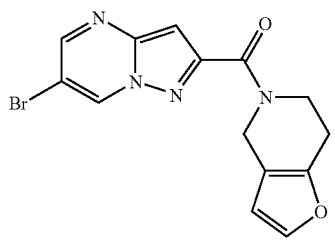

In close analogy to the procedure described in Example 1, 6-bromo-pyrazolo[1,5-a]pyrimidine-2-carboxylic acid is reacted with 4,5,6,7-tetrahydro-furo[3,2-c]pyridine to provide the title compound in moderate yield.
LC/MS: m/z=348 (MH$^+$)

Example 32

(6-Bromo-pyrazolo[1,5-a]pyrimidin-2-yl)-(6-methyl-6,7-dihydro-4H-furo[3,2-c]pyridin-5-yl)-methanone

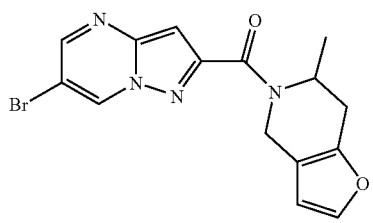

In close analogy to the procedure described in Example 1, 6-bromo-pyrazolo[1,5-a]pyrimidine-2-carboxylic acid is reacted with 6-methyl-4,5,6,7-tetrahydro-furo[3,2-c]pyridine to provide the title compound in moderate yield.
LC/MS: m/z=362 (MH$^+$)

The stereo-isomers of this compound are separated. The S-configurated compound has a different activity than the R-configurated compound.

Example 33

(6-Chloro-pyrazolo[1,5-a]pyrimidin-2-yl)-(6-methyl-6,7-dihydro-4H-furo[3,2-c]pyridin-5-yl)-methanone

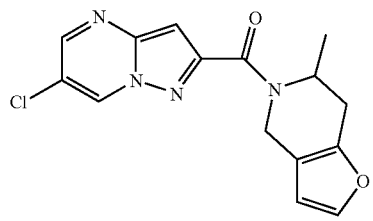

In close analogy to the procedure described in Example 1, 6-chloro-pyrazolo[1,5-a]pyrimidine-2-carboxylic acid is reacted with 6-methyl-4,5,6,7-tetrahydro-furo[3,2-c]pyridine to provide the title compound in moderate yield.
LC/MS: m/z=318 (MH$^+$)

The stereo-isomers of this compound are separated. The S-configurated compound has a different activity than the R-configurated compound.

Example 34

(6-Bromo-pyrazolo[1,5-a]pyrimidin-2-yl)-(1,4,6,7-tetrahydro-pyrrolo[3,2-c]pyridin-5-yl)-methanone

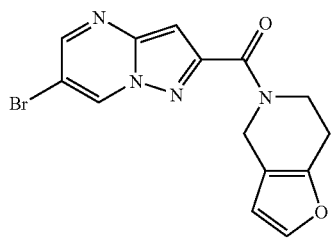

In close analogy to the procedure described in Example 1, 6-bromo-pyrazolo[1,5-a]pyrimidine-2-carboxylic acid is reacted with 4,5,6,7-tetrahydro-1H-pyrrolo[3,2-c]pyridine to provide the title compound in moderate yield.
LC/MS: m/z=348 (MH$^+$)

The stereo-isomers of this compound are separated. The S-configurated compound has a different activity than the R-configurated compound.

Example 35

(6-Chloro-pyrazolo[1,5-a]pyrimidin-2-yl)-(1,4,6,7-tetrahydro-pyrrolo[3,2-c]pyridin-5-yl)-methanone

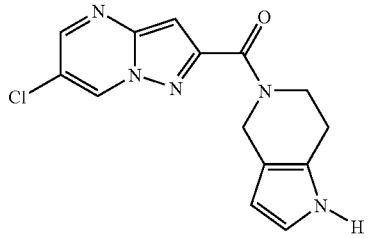

In close analogy to the procedure described in Example 1, 6-chloro-pyrazolo[1,5-a]pyrimidine-2-carboxylic acid is reacted with 4,5,6,7-tetrahydro-1H-pyrrolo[3,2-c]pyridine to provide the title compound in moderate yield.

LC/MS: m/z=317 (MH$^+$)

The stereo-isomers of this compound are separated. The S-configurated compound has a different activity than the R-configurated compound.

Example 36

(6-Chloro-pyrazolo[1,5-a]pyrimidin-2-yl)-(4-methyl-1,4,6,7-tetrahydro-pyrrolo[3,2-c]pyridin-5-yl)-methanone

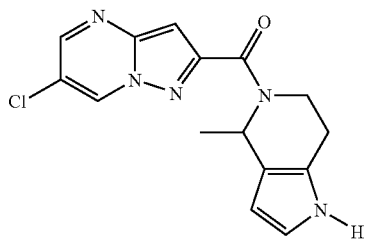

In close analogy to the procedure described in Example 1, 6-chloro-pyrazolo[1,5-a]pyrimidine-2-carboxylic acid is reacted with 4-methyl-4,5,6,7-tetrahydro-1H-pyrrolo[3,2-c]pyridine to provide the title compound in moderate yield.

LC/MS: m/z=331 (MH$^+$)

The stereo-isomers of this compound are separated. The S-configurated compound has a different activity than the R-configurated compound.

Example 37

(6-Bromo-pyrazolo[1,5-a]pyrimidin-2-yl)-(4-methyl-1,4,6,7-tetrahydro-pyrrolo[3,2-c]pyridin-5-yl)-methanone

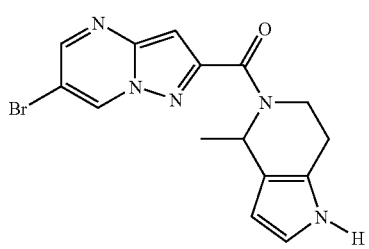

In close analogy to the procedure described in Example 1, 6-bromo-pyrazolo[1,5-a]pyrimidine-2-carboxylic acid is reacted with 4-methyl-4,5,6,7-tetrahydro-1H-pyrrolo[3,2-c]pyridine to provide the title compound in moderate yield.

LC/MS: m/z=375 (MH$^+$)

The stereo-isomers of this compound are separated. The S-configurated compound has a different activity than the R-configurated compound.

Example 38

(6-Bromo-pyrazolo[1,5-a]pyrimidin-2-yl)-(8-methyl-5,8-dihydro-6H-[1,7]naphthyridin-7-yl)-methanone

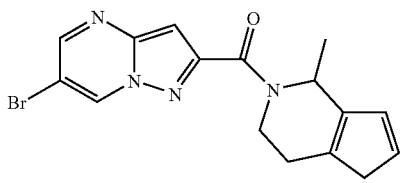

In close analogy to the procedure described in Example 1, 6-bromo-pyrazolo[1,5-a]pyrimidine-2-carboxylic acid is reacted with 1-Methyl-2,3,4,5-tetrahydro-1H-[2]pyrindine to provide the title compound in moderate yield.

LC/MS: m/z 360 (MH$^+$)

The stereo-isomers of this compound are separated. The S-configurated compound has a different activity than the R-configurated compound.

Example 39

(6-Chloro-pyrazolo[1,5-a]pyrimidin-2-yl)-(1-methyl-3,4-dihydro-1H-[2,7]naphthyridin-2-yl)-methanone

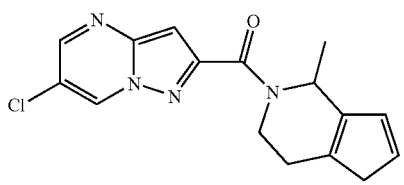

In close analogy to the procedure described in Example 1, 6-chloro-pyrazolo[1,5-a]pyrimidine-2-carboxylic acid is reacted with 1-Methyl-2,3,4,5-tetrahydro-1H-[2]pyrindine to provide the title compound in moderate yield.

LC/MS: m/z=316 (MH$^+$). The stereo-isomers of this compound are separated. The S-configurated compound has a different activity than the R-configurated compound.

Example 40

5-[(6-Bromopyrazolo[1,5-a]pyrimidin-2-yl)carbonyl]-3-phenyl-4,5,6,7-tetrahydroisoxazolo[4,5-c]pyridine

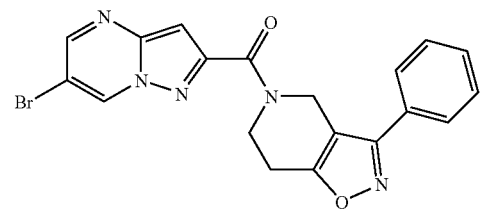

In close analogy to the procedure described in Example 1, 6-bromo-pyrazolo[1,5-a]pyrimidine-2-carboxylic acid is reacted with 3-Phenyl-4,5,6,7-tetrahydro-isoxazolo[4,5-c]pyridine to provide the title compound.

Yield: 69%

LC/MS: m/z=529 (MH+)

Example 41

(6-Bromo-pyrazolo[1,5-a]pyrimidin-2-yl)-(4-methyl-6,7-dihydro-4H-thieno[3,2-c]pyridin-5-yl)-methanone, in the form of the S-configurated isomer,

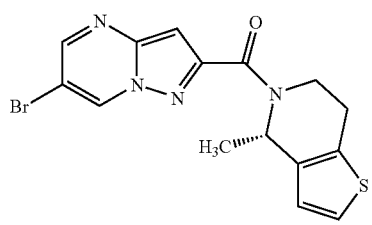

is prepared by the following reaction scheme, in which R stands for e.g. hydrogen.

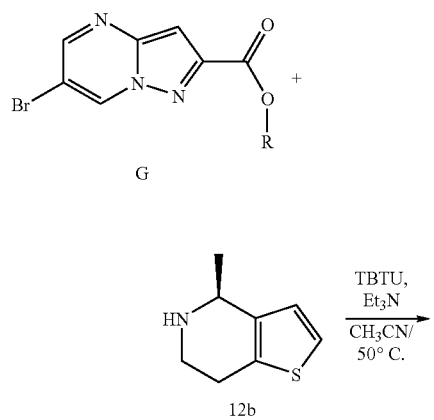

The compound 13 is synthesized and isolated by the same method as for compound 14 in the amount of 48 mg (~55%) as white crystals (m.p. 136-137° C.). M/z (APCI+) 377 (MH+).

$^1$H NMR (DMSO-d$_6$, 400 MHz) δH 1.45 (m, 3H), 2.9-2.7 (m, 2H), 3.5-3.4 (t, 1H), 4.7-4.3 (m, 1H), 5.6-5.2 (m, 1H), 7.0-6.7 (m, 1H), 7.0 (m, 1H), 7.4-7.3 (m, 1H), 8.6 (s, 1H), 9.6 (s, 1H). HPLC (Chiralcel OD-H 4.6×250 mm 5 mkm, hexane/IPA 65/35, 1 ml/min, ambient t, UV at 245 nm); RT 21.480 min.; e.e.>99.5%.

Example 42

(6-Bromo-pyrazolo[1,5-a]pyrimidin-2-yl)-(4-methyl-6,7-dihydro-4H-thieno[3,2-c]pyridin-5-yl)-methanone, in the form of the R-configurated isomer

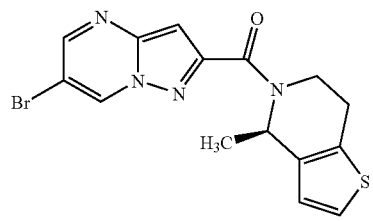

The compound is prepared as following:

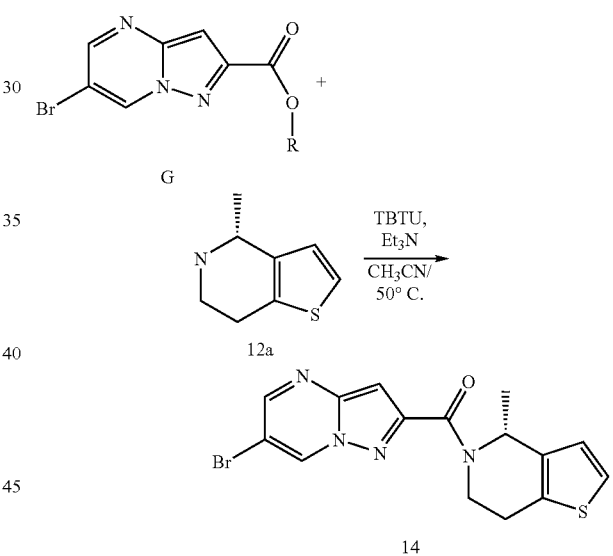

pyrazolopyrimidine-carboxylic acid G (R=H; 103 mg, 0.427 mmol), amine 12a (R-configuration; hydrochloride, 81 mg, 0.427 mmol), TBTU (223 mg, 0.694 mmol) and Et$_3$N (113 mg, 1.12 mmol) are stirred in dry acetonitrile for ~3 hrs at 50° C. The reaction is monitored by TLC. When the reaction is over the reaction mixture is concentrated in vacuum. A compound 14 is isolated by preparative column chromatography (silica gel 60/100, eluent: hexane-hexane/ethyl acetate, 1/4). As a result, 93 mg is obtained (~58%) as white crystals (M.p. 142-144° C. m/z (APCI+) 377 (MH+).

$^1$H NMR (DMSO-d$_6$, 400 MHz) δH 1.5 (m, 3H), 2.9-2.7 (m, 2H), 3.4-3.4 (t, 1H), 4.7-4.4 (m, 1H), 5.6-5.3 (m, 1H), 7.0-6.8 (m, 1H), 7.0 (m, 1H), 7.4-7.3 (m, 1H), 8.7 (s, 1H), 9.6 (s, 1H). HPLC (Chiralcel OD-H 4.6×250 mm 5 mkm, hexane/IPA 65/35, 1 ml/min, ambient t, UV at 245 nm) RT 25,453 min., e.e>99.0%.

Example 43

(6-Chloro-pyrazolo[1,5-a]pyrimidin-2-yl)-(2,4-dimethyl-6,7-dihydro-4H-furo[3,2-c]pyridin-5-yl)-methanone

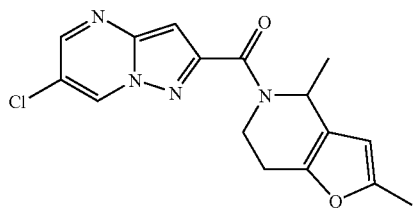

In close analogy to the procedure described in Example 11, 6-chloro-pyrazolo[1,5-a]pyrimidine-2-carboxylic acid is reacted with 2,4-Dimethyl-4,5,6,7-tetrahydro-furo[3,2-c]pyridine to provide the title compound.

Yield: 10%

LC/MS: m/z=331 (MH+)

$^1$H NMR (CDCl$_3$) δ: 1.28, 1.46-1.51, 1.59, 2.26, 2.59, 2.97, 3.21, 3.45, 4.52, 4.96, 5.24, 5.57, 5.70, 5.87, 7.06, 8.49, 8.72.

The stereo-isomers of this compound are separated. The S-configurated compound has a different activity than the R-configurated compound.

Example 44

(6-Bromo-pyrazolo[1,5-a]pyrimidin-2-yl)-(2,4-dimethyl-6,7-dihydro-4H-furo[3,2-c]pyridin-5-yl)-methanone

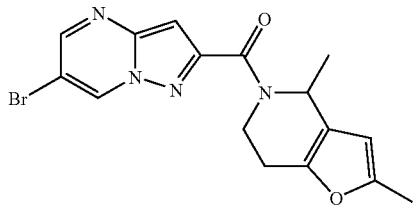

In close analogy to the procedure described in Example 1, 6-bromo-pyrazolo[1,5-a]pyrimidine-2-carboxylic acid is reacted with 2,4-Dimethyl-4,5,6,7-tetrahydro-furo[3,2-c]pyridine to provide the title compound.

Yield: 12%

LC/MS: m/z=377 (MH+)

$^1$H NMR (CDCl$_3$) δ: 1.26, 1.45-1.51, 2.26, 2.61, 2.97, 3.21, 3.46, 4.52, 4.96, 5.24, 5.57, 5.70, 5.87, 7.05, 8.53, 8.83.

The stereo-isomers of this compound are separated. The S-configurated compound has a different activity than the R-configurated compound.

Example 45

(6-Chloro-pyrazolo[1,5-a]pyrimidin-2-yl)-(3,4-dimethyl-6,7-dihydro-4H-thieno[3,2-c]pyridin-5-yl)-methanone

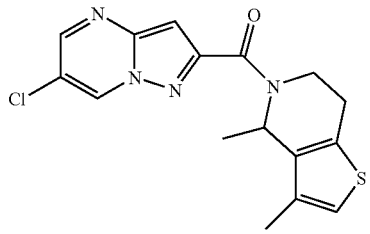

In close analogy to the procedure described in Example 1, 6-chloro-pyrazolo[1,5-a]pyrimidine-2-carboxylic acid is reacted with 2,4-dimethyl-4,5,6,7-tetrahydro-thieno[3,2-c]pyridine to provide the title compound.

Yield: 68%

LC/MS: m/z=347 (MH$^+$)

$^1$H NMR (d$_6$-DMSO) δ: 1.41, 2.16, 2.70-3.00, 3.45-3.55, 4.25-4.37, 5.46-5.59, 6.86-7.10, 8.66, 9.55.

The stereo-isomers of this compound are separated. The S-configurated compound has a different activity than the R-configurated compound.

Example 46

(6-Bromo-pyrazolo[1,5-a]pyrimidin-2-yl)-(1,7,7-trimethyl-1,3,4,7-tetrahydro-[2]pyrindin-2-yl)-methanone

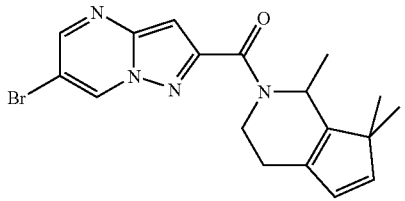

In close analogy to the procedure described in Example 1, 6-bromo-pyrazolo[1,5-a]pyrimidine-2-carboxylic acid is reacted with 1,7,7-trimethyl-2,3,4,7-tetrahydro-1H-[2]pyrindine to provide the title compound.

LC/MS: m/z=388 (MH$^+$)

The stereo-isomers of this compound are separated. The S-configurated compound has a different activity than the R-configurated compound.

Example 47

(6-Chloro-pyrazolo[1,5-a]pyrimidin-2-yl)-(1,7,7-trimethyl-1,3,4,7-tetrahydro-[2]pyrindin-2-yl)-methanone

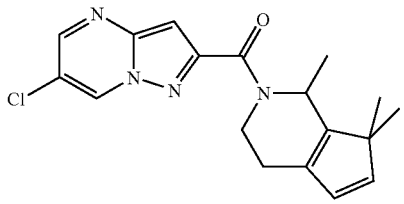

In close analogy to the procedure described in Example 1, 6-chloro-pyrazolo[1,5-a]pyrimidine-2-carboxylic acid is reacted with 1,7,7-trimethyl-2,3,4,7-tetrahydro-1H-[2]pyrindine to provide the title compound.

LC/MS: m/z=343 (MH$^+$)

The stereo-isomers of this compound are separated. The S-configurated compound has a different activity than the R-configurated compound.

Example 48

(6-Bromo-pyrazolo[1,5-a]pyrimidin-2-yl)-(1,7,7-trimethyl-1,3,4,7-tetrahydro-[2]pyrindin-2-yl)-methanone

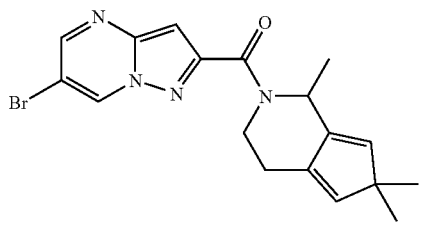

In close analogy to the procedure described in Example 1, 6-bromo-pyrazolo[1,5-a]pyrimidine-2-carboxylic acid is reacted with 1,6,6-trimethyl-2,3,4,6-tetrahydro-1H-[2]pyrindine to provide the title compound.

LC/MS: m/z=388 (MH$^+$)

The stereo-isomers of this compound are separated. The S-configurated compound has a different activity than the R-configurated compound.

Example 49

(6-Chloro-pyrazolo[1,5-a]pyrimidin-2-yl)-(1,7,7-trimethyl-1,3,4,7-tetrahydro-[2]pyrindin-2-yl)-methanone

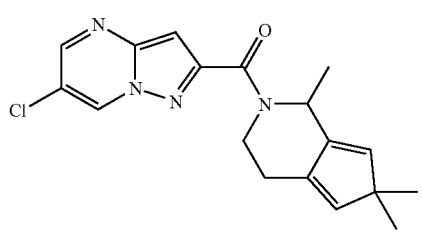

In close analogy to the procedure described in Example 1, 6-chloro-pyrazolo[1,5-a]pyrimidine-2-carboxylic acid is reacted with 1,6,6-trimethyl-2,3,4,6-tetrahydro-1H-[2]pyrindine to provide the title compound.

LC/MS: m/z=343 (MH$^+$)

The stereo-isomers of this compound are separated. The S-configurated compound has a different activity than the R-configurated compound.

Example 50

(6-Bromo-pyrazolo[1,5-a]pyrimidin-2-yl)-(1,5,5-trimethyl-1,3,4,5-tetrahydro-[2]pyrindin-2-yl)-methanone

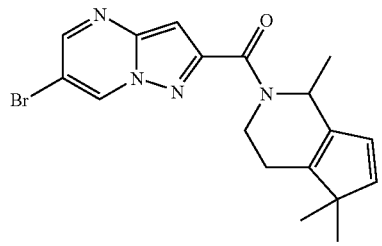

In close analogy to the procedure described in Example 1, 6-bromo-pyrazolo[1,5-a]pyrimidine-2-carboxylic acid is reacted with 1,5,5-trimethyl-2,3,4,5-tetrahydro-1H-[2]pyrindine to provide the title compound.

LC/MS: m/z=388 (MH$^+$)

The stereo-isomers of this compound are separated. The S-configurated compound has a different activity than the R-configurated compound.

Example 51

(6-Chloro-pyrazolo[1,5-a]pyrimidin-2-yl)-(1,5,5-trimethyl-1,3,4,5-tetrahydro-[2]pyrindin-2-yl)-methanone

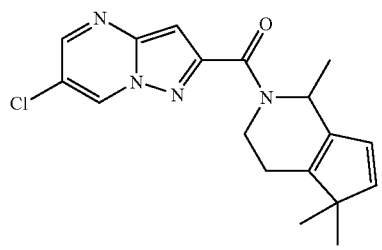

In close analogy to the procedure described in Example 1, 6-chloro-pyrazolo[1,5-a]pyrimidine-2-carboxylic acid is reacted with 1,5,5-trimethyl-2,3,4,5-tetrahydro-1H-[2]pyrindine to provide the title compound.

LC/MS: m/z=343 (MH$^+$)

The stereo-isomers of this compound are separated. The S-configurated compound has a different activity than the R-configurated compound.

Example 52

(6-Bromo-pyrazolo[1,5-a]pyrimidin-2-yl)-[4-methyl-1-(1H-tetrazol-5-yl)-1,4,6,7-tetrahydro-pyrrolo[3,2-c]pyridin-5-yl]-methanone

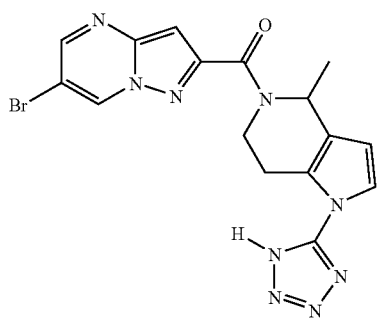

(6-Bromo-pyrazolo[1,5-a]pyrimidin-2-yl)-(4-methyl-1,4,6,7-tetrahydro-pyrrolo[3,2-c]pyridin-5-yl)-methanone is reacted with 1H tetrazole under Buchwald reaction conditions to provide the title compound.

The stereo-isomers of this compound are separated. The S-configurated compound has a different activity than the R-configurated compound.

LC/MS: m/z=429 (MH+)

(see S. L. Buchwald, Acc. Chem. Res. 1998, 31, 805; S. L. Buchwald, J. Organomet. Chem. 1999, 576, 125, 37; S. L. Buchwald, Angew. Chem. Int. Ed. Engl. 1999, 38, 2413).

Example 53

(6-Chloro-pyrazolo[1,5-a]pyrimidin-2-yl)-[4-methyl-1-(1H-tetrazol-5-yl)-1,4,6,7-tetrahydro-pyrrolo[3,2-c]pyridin-5-yl]-methanone

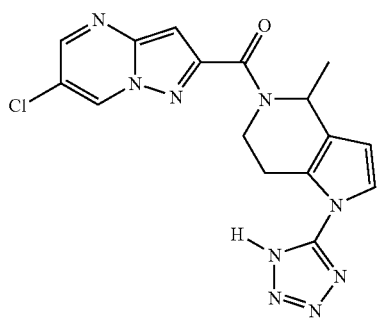

In close analogy to the procedure described in Example 52, (6-chloro-pyrazolo[1,5-a]pyrimidin-2-yl)-(4-methyl-1,4,6,7-tetrahydro-pyrrolo[3,2-c]pyridin-5-yl)-methanone is reacted with 1H tetrazole to provide the title compound.

LC/MS: m/z=384 (MH+)

The stereo-isomers of this compound are separated. The S-configurated compound has a different activity than the R-configurated compound.

Example 54

(6-Bromo-pyrazolo[1,5-a]pyrimidin-2-yl)-[7-methyl-1-(1H-tetrazol-5-yl)-1,4,5,7-tetrahydro-pyrrolo[2,3-c]pyridin-6-yl]-methanone

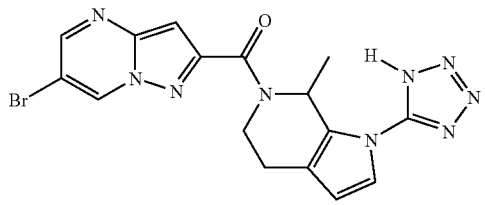

In close analogy to the procedure described in Example 52, (6-bromo-pyrazolo[1,5-a]pyrimidin-2-yl)-(7-methyl-1,4,5,7-tetrahydro-pyrrolo[2,3-c]pyridin-6-yl)-methanone is reacted with 1H tetrazole to provide the title compound.

LC/MS: m/z=429 (MH+)

The stereo-isomers of this compound are separated. The S-configurated compound has a different activity than the R-configurated compound.

Example 55

(6-Chloro-pyrazolo[1,5-a]pyrimidin-2-yl)-[7-methyl-1-(1H-tetrazol-5-yl)-1,4,5,7-tetrahydro-pyrrolo[2,3-c]pyridin-6-yl]-methanone

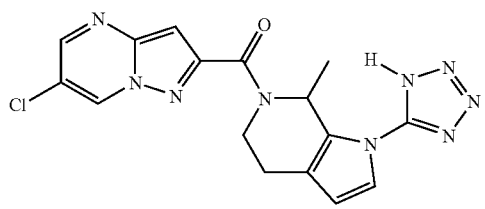

In close analogy to the procedure described in Example 52, (6-chloro-pyrazolo[1,5-a]pyrimidin-2-yl)-(7-methyl-1,4,5,7-tetrahydro-pyrrolo[2,3-c]pyridin-6-yl)-methanone is reacted with 1H tetrazole to provide the title compound.

LC/MS: m/z=384 (MH+)

The stereo-isomers of this compound are separated. The S-configurated compound has a different activity than the R-configurated compound.

The stereo-isomers of this compound are separated. The S-configurated compound has a different activity than the R-configurated compound.

Example 56

(6-Bromo-pyrazolo[1,5-a]pyrimidin-2-yl)-[4-methyl-1-(1H-tetrazol-5-yl)-2,4,6,7-tetrahydro-pyrrolo[3,4-c]pyridin-5-yl]-methanone

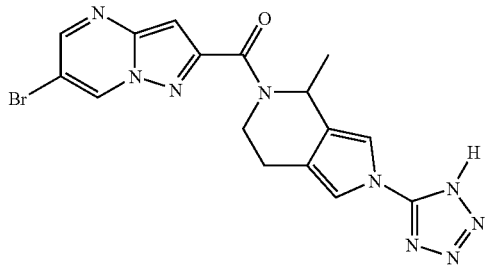

In close analogy to the procedure described in Example 52, (6-bromo-pyrazolo[1,5-a]pyrimidin-2-yl)-(4-methyl-2,4,6,7-tetrahydro-pyrrolo[3,4-c]pyridin-5-yl)-methanone is reacted with 1H tetrazole to provide the title compound.
LC/MS: m/z=429 (MH+)
The stereo-isomers of this compound are separated. The S-configurated compound has a different activity than the R-configurated compound.

Example 57

(6-Chloro-pyrazolo[1,5-a]pyrimidin-2-yl)-[4-methyl-1-(1H-tetrazol-5-yl)-2,4,6,7-tetrahydro-pyrrolo[3,4-c]pyridin-5-yl]-methanone

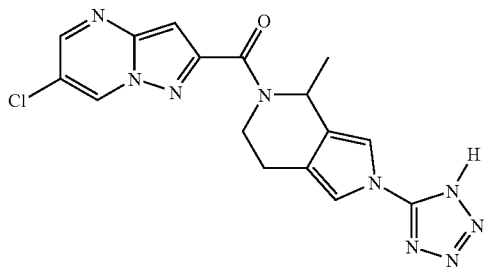

In close analogy to the procedure described in Example 52, (6-chloro-pyrazolo[1,5-a]pyrimidin-2-yl)-(4-methyl-2,4,6,7-tetrahydro-pyrrolo[3,4-c]pyridin-5-yl)-methanone is reacted with 1H tetrazole to provide the title compound.
LC/MS: m/z=384 (MH+)
The stereo-isomers of this compound are separated. The S-configurated compound has a different activity than the R-configurated compound.

Example 58

(2-Bromo-7-methyl-4,7-dihydro-5H-furo[2,3-c]pyridin-6-yl)-(6-bromo-pyrazolo[1,5-a]pyrimidin-2-yl)-methanone

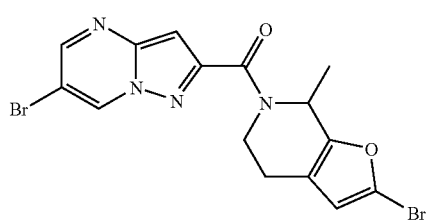

In close analogy to the procedure described in Example 1, 6-bromo-pyrazolo[1,5-a]pyrimidine-2-carboxylic acid is reacted with 2-bromo-7-methyl-4,5,6,7-tetrahydrofuro[2,3-c]pyridine to provide the title compound.
LC/MS: m/z=441 (MH+)
The stereo-isomers of this compound are separated. The S-configurated compound has a different activity than the R-configurated compound.

Example 59

(2-Chloro-7-methyl-4,7-dihydro-5H-furo[2,3-c]pyridin-6-yl)-(6-bromo-pyrazolo[1,5-a]pyrimidin-2-yl)-methanone

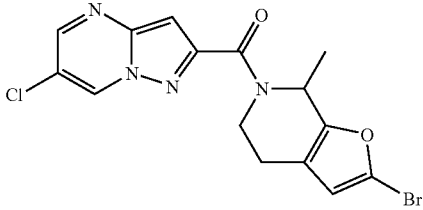

In close analogy to the procedure described in Example 1, 6-chloro-pyrazolo[1,5-a]pyrimidine-2-carboxylic acid is reacted with 2-bromo-7-methyl-4,5,6,7-tetrahydrofuro[2,3-c]pyridine to provide the title compound.
LC/MS: m/z=396 (MH+)
The stereo-isomers of this compound are separated. The S-configurated compound has a different activity than the R-configurated compound.

Example 60

2-Bromo-7-methyl-4,7-dihydro-5H-furo[2,3-c]pyridin-6-yl)-(6-chloro-pyrazolo[1,5-a]pyrimidin-2-yl)-methanone

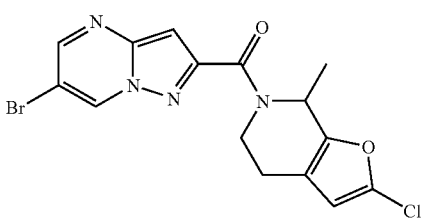

In close analogy to the procedure described in Example 1, 6-bromo-pyrazolo[1,5-a]pyrimidine-2-carboxylic acid is reacted with 2-chloro-7-methyl-4,5,6,7-tetrahydrofuro[2,3-c]pyridine to provide the title compound.
LC/MS: m/z=396 (MH+)
The stereo-isomers of this compound are separated. The S-configurated compound has a different activity than the R-configurated compound.

Example 61

2-Chloro-7-methyl-4,7-dihydro-5H-furo[2,3-c]pyridin-6-yl)-(6-chloro-pyrazolo[1,5-a]pyrimidin-2-yl)-methanone

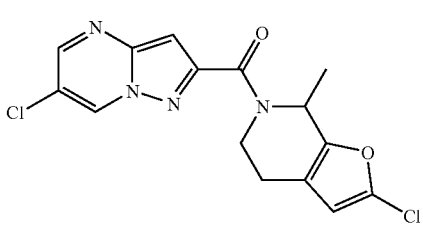

In close analogy to the procedure described in Example 1, 6-chloro-pyrazolo[1,5-a]pyrimidine-2-carboxylic acid is reacted with 2-chloro-7-methyl-4,5,6,7-tetrahydrofuro[2,3-c]pyridine to provide the title compound.

LC/MS: m/z=351 (MH+)

The stereo-isomers of this compound are separated. The S-configurated compound has a different activity than the R-configurated compound.

Example 62

(2-Bromo-7-methyl-4,7-dihydro-5H-thieno[2,3-c]pyridin-6-yl)-(6-bromo-pyrazolo[1,5-a]pyrimidin-2-yl)-methanone

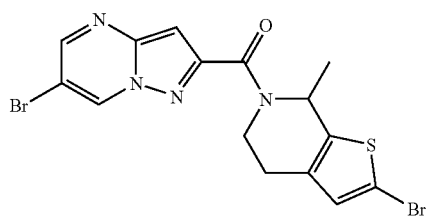

In close analogy to the procedure described in Example 1, 6-bromo-pyrazolo[1,5-a]pyrimidine-2-carboxylic acid is reacted with 2-bromo-7-methyl-4,5,6,7-tetrahydrothieno[2,3-c]pyridine to provide the title compound.

LC/MS: m/z=457 (MH+)

The stereo-isomers of this compound are separated. The S-configurated compound has a different activity than the R-configurated compound.

Example 63

(2-Chloro-7-methyl-4,7-dihydro-5H-thieno[2,3-c]pyridin-6-yl)-(6-bromo-pyrazolo[1,5-a]pyrimidin-2-yl)-methanone

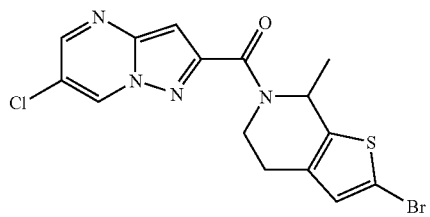

In close analogy to the procedure described in Example 1, 6-chloro-pyrazolo[1,5-a]pyrimidine-2-carboxylic acid is reacted with 2-bromo-7-methyl-4,5,6,7-tetrahydrothieno[2,3-c]pyridine to provide the title compound.

LC/MS: m/z=412 (MH+)

The stereo-isomers of this compound are separated. The S-configurated compound has a different activity than the R-configurated compound.

Example 64

(2-Bromo-7-methyl-4,7-dihydro-5H-thieno[2,3-c]pyridin-6-yl)-(6-chloro-pyrazolo[1,5-a]pyrimidin-2-yl)-methanone

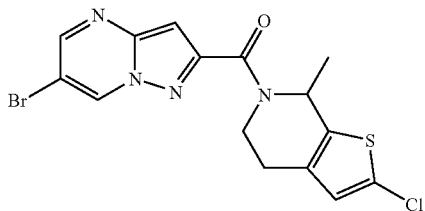

In close analogy to the procedure described in Example 1, 6-bromo-pyrazolo[1,5-a]pyrimidine-2-carboxylic acid is reacted with 2-chloro-7-methyl-4,5,6,7-tetrahydrothieno[2,3-c]pyridine to provide the title compound.

LC/MS: m/z=412 (MH+)

The stereo-isomers of this compound are separated. The S-configurated compound has a different activity than the R-configurated compound.

Example 65

(2-Chloro-7-methyl-4,7-dihydro-5H-thieno[2,3-c]pyridin-6-yl)-(6-chloro-pyrazolo[1,5-a]pyrimidin-2-yl)-methanone

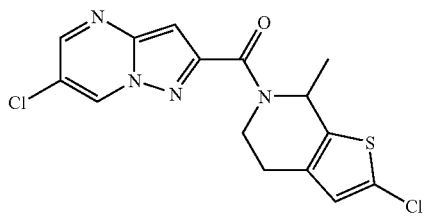

In close analogy to the procedure described in Example 1, 6-chloro-pyrazolo[1,5-a]pyrimidine-2-carboxylic acid is reacted with 2-chloro-7-methyl-4,5,6,7-tetrahydrothieno[2,3-c]pyridine to provide the title compound.

LC/MS: m/z=367 (MH+)

The stereo-isomers of this compound are separated. The S-configurated compound has a different activity than the R-configurated compound.

Example 66

(3-Bromo-7-methyl-4,7-dihydro-5H-furo[2,3-c]pyridin-6-yl)-(6-bromo-pyrazolo[1,5-a]pyrimidin-2-yl)-methanone

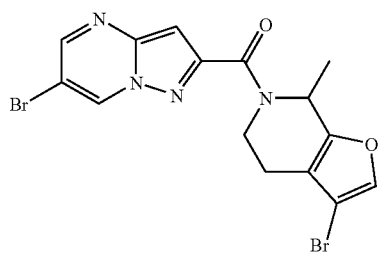

In close analogy to the procedure described in Example 1, 6-bromo-pyrazolo[1,5-a]pyrimidine-2-carboxylic acid is reacted with 3-bromo-7-methyl-4,5,6,7-tetrahydrofuro[2,3-c]pyridine to provide the title compound.

LC/MS: m/z=441 (MH+)

The stereo-isomers of this compound are separated. The S-configurated compound has a different activity than the R-configurated compound.

Example 67

(3-Chloro-7-methyl-4,7-dihydro-5H-furo[2,3-c]pyridin-6-yl)-(6-bromo-pyrazolo[1,5-a]pyrimidin-2-yl)-methanone

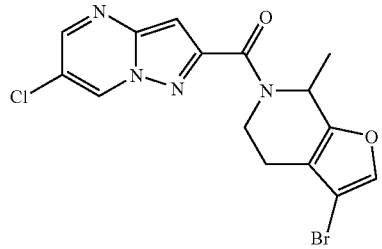

In close analogy to the procedure described in Example 1, 6-chloro-pyrazolo[1,5-a]pyrimidine-2-carboxylic acid is reacted with 3-bromo-7-methyl-4,5,6,7-tetrahydrofuro[2,3-c]pyridine to provide the title compound.

LC/MS: m/z=396 (MH+)

The stereo-isomers of this compound are separated. The S-configurated compound has a different activity than the R-configurated compound.

Example 68

(3-Bromo-7-methyl-4,7-dihydro-5H-furo[2,3-c]pyridin-6-yl)-(6-chloro-pyrazolo[1,5-a]pyrimidin-2-yl)-methanone

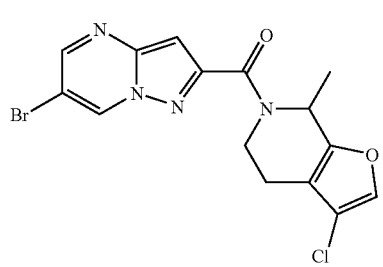

In close analogy to the procedure described in Example 1, 6-bromo-pyrazolo[1,5-a]pyrimidine-2-carboxylic acid is reacted with 3-chloro-7-methyl-4,5,6,7-tetrahydrofuro[2,3-c]pyridine to provide the title compound.

LC/MS: m/z=396 (MH+)

The stereo-isomers of this compound are separated. The S-configurated compound has a different activity than the R-configurated compound.

Example 69

(3-Chloro-7-methyl-4,7-dihydro-5H-furo[2,3-c]pyridin-6-yl)-(6-chloro-pyrazolo[1,5-a]pyrimidin-2-yl)-methanone

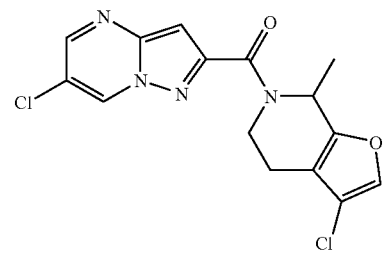

In close analogy to the procedure described in Example 1, 6-chloro-pyrazolo[1,5-a]pyrimidine-2-carboxylic acid is reacted with 3-chloro-7-methyl-4,5,6,7-tetrahydrofuro[2,3-c]pyridine to provide the title compound.

LC/MS: m/z=351 (MH+)

The stereo-isomers of this compound are separated. The S-configurated compound has a different activity than the R-configurated compound.

Example 70

(3-Bromo-7-methyl-4,7-dihydro-5H-thieno[2,3-c]pyridin-6-yl)-(6-bromo-pyrazolo[1,5-a]pyrimidin-2-yl)-methanone

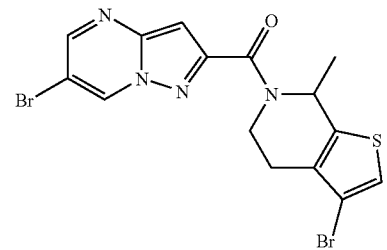

In close analogy to the procedure described in Example 1, 6-bromo-pyrazolo[1,5-a]pyrimidine-2-carboxylic acid is reacted with 3-bromo-7-methyl-4,5,6,7-tetrahydrothieno[2,3-c]pyridine to provide the title compound.

LC/MS: m/z=457 (MH+)

The stereo-isomers of this compound are separated. The S-configurated compound has a different activity than the R-configurated compound.

Example 71

(3-Chloro-7-methyl-4,7-dihydro-5H-thieno[2,3-c]pyridin-6-yl)-(6-bromo-pyrazolo[1,5-a]pyrimidin-2-yl)-methanone

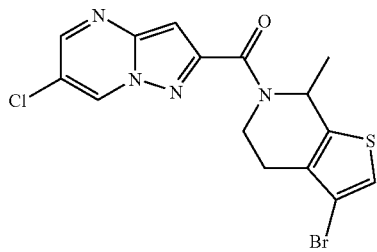

In close analogy to the procedure described in Example 1, 6-chloro-pyrazolo[1,5-a]pyrimidine-2-carboxylic acid is reacted with 3-bromo-7-methyl-4,5,6,7-tetrahydrothieno[2,3-c]pyridine to provide the title compound.
LC/MS: m/z=412 (MH+)
The stereo-isomers of this compound are separated. The S-configurated compound has a different activity than the R-configurated compound.

Example 72

(3-Bromo-7-methyl-4,7-dihydro-5H-thieno[2,3-c]pyridin-6-yl)-(6-chloro-pyrazolo[1,5-a]pyrimidin-2-yl)-methanone

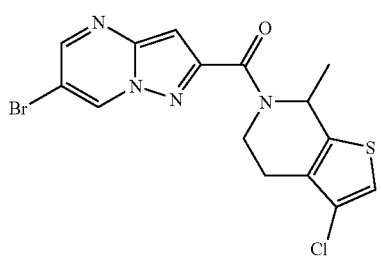

In close analogy to the procedure described in Example 1, 6-bromo-pyrazolo[1,5-a]pyrimidine-2-carboxylic acid is reacted with 3-chloro-7-methyl-4,5,6,7-tetrahydrothieno[2,3-c]pyridine to provide the title compound.
LC/MS: m/z=412 (MH+)
The stereo-isomers of this compound are separated. The S-configurated compound has a different activity than the R-configurated compound.

Example 73

(3-Chloro-7-methyl-4,7-dihydro-5H-thieno[2,3-c]pyridin-6-yl)-(6-chloro-pyrazolo[1,5-a]pyrimidin-2-yl)-methanone

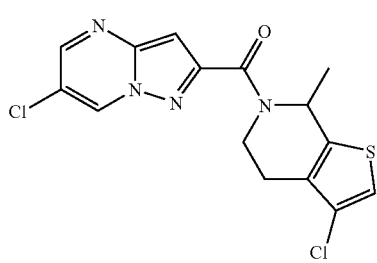

In close analogy to the procedure described in Example 1, 6-chloro-pyrazolo[1,5-a]pyrimidine-2-carboxylic acid is reacted with 3-chloro-7-methyl-4,5,6,7-tetrahydrothieno[2,3-c]pyridine to provide the title compound.
LC/MS: m/z=367 (MH+)
The stereo-isomers of this compound are separated. The S-configurated compound has a different activity than the R-configurated compound.

Example 74

1-[5-(6-Bromo-pyrazolo[1,5-a]pyrimidine-2-carbonyl)-4-methyl-4,5,6,7-tetrahydropyrrolo[3,2-c]pyridin-1-yl]-ethanone

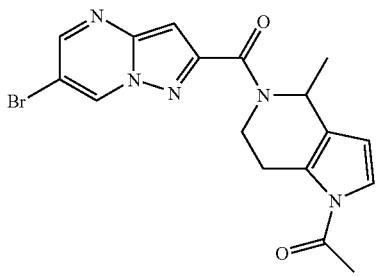

(6-Bromo-pyrazolo[1,5-a]pyrimidin-2-yl)-(4-methyl-1,4,6,7-tetrahydro-pyrrolo[3,2-c]pyridin-5-yl)-methanone is reacted with acetic acid to provide the title compound.
LC/MS: m/z=403 (MH+)
The stereo-isomers of this compound are separated. The S-configurated compound has a different activity than the R-configurated compound.

Example 75

1-[5-(6-Chloro-pyrazolo[1,5-a]pyrimidine-2-carbonyl)-4-methyl-4,5,6,7-tetrahydropyrrolo[3,2-c]pyridin-1-yl]-ethanone

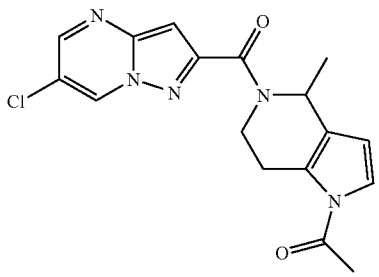

(6-Chloro-pyrazolo[1,5-a]pyrimidin-2-yl)-(4-methyl-1,4,6,7-tetrahydro-pyrrolo[3,2-c]pyridin-5-yl)-methanone is reacted with acetic acid to provide the title compound.
LC/MS: m/z=358 (MH+)
The stereo-isomers of this compound are separated. The S-configurated compound has a different activity than the R-configurated compound.

Example 76

1-[6-(6-Bromo-pyrazolo[1,5-a]pyrimidine-2-carbonyl)-7-methyl-4,5,6,7-tetrahydropyrrolo[2,3-c]pyridin-1-yl]-ethanone

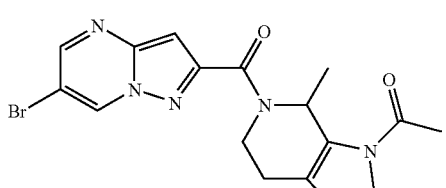

(6-Bromo-pyrazolo[1,5-a]pyrimidin-2-yl)-(7-methyl-1,4,5,7-tetrahydro-pyrrolo[2,3-c]pyridin-6-yl)-methanone is reacted with acetic acid to provide the title compound.

LC/MS: m/z=403 (MH$^+$)

The stereo-isomers of this compound are separated. The S-configurated compound has a different activity than the R-configurated compound.

Example 77

1-[6-(6-Chloro-pyrazolo[1,5-a]pyrimidine-2-carbonyl)-7-methyl-4,5,6,7-tetrahydropyrrolo[2,3-c]pyridin-1-yl]-ethanone

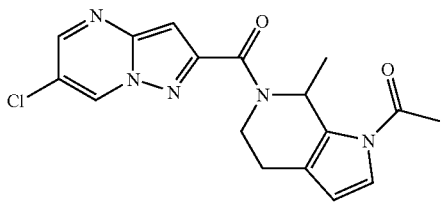

(6-Chloro-pyrazolo[1,5-a]pyrimidin-2-yl)-(7-methyl-1,4,5,7-tetrahydro-pyrrolo[2,3-c]pyridin-6-yl)-methanone is reacted with acetic acid to provide the title compound.

LC/MS: m/z=358 (MH$^+$)

The stereo-isomers of this compound are separated. The S-configurated compound has a different activity than the R-configurated compound.

Example 78

(6-Bromo-pyrazolo[1,5-a]pyrimidin-2-yl)-(4-methyl-6,7-dihydro-4H-oxazolo[4,5-c]pyridin-5-yl)-methanone

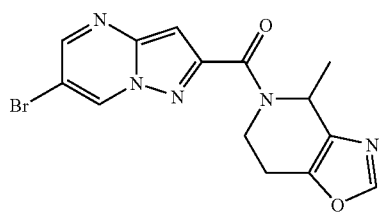

(6-Bromo-pyrazolo[1,5-a]pyrimidin-2-yl)-(7-methyl-1,4,5,7-tetrahydro-pyrrolo[2,3-c]pyridin-6-yl)-methanone is reacted with 4-methyl-4,5,6,7-tetrahydro-oxazolo[4,5-c]pyridine to provide the title compound.

LC/MS: m/z=363 (MH$^+$)

The stereo-isomers of this compound are separated. The S-configurated compound has a different activity than the R-configurated compound.

Example 79

(6-Bromo-pyrazolo[1,5-a]pyrimidin-2-yl)-(2-fluoro-4-methyl-6,7-dihydro-4H-oxazolo[4,5-c]pyridin-5-yl)-methanone

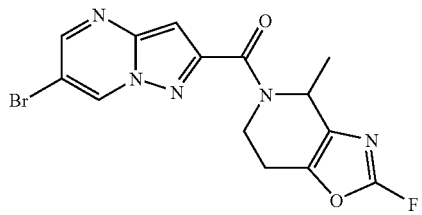

(6-Bromo-pyrazolo[1,5-a]pyrimidin-2-yl)-(7-methyl-1,4,5,7-tetrahydro-pyrrolo[2,3-c]pyridin-6-yl)-methanone is reacted with 2-fluoro-4-methyl-4,5,6,7-tetrahydrooxazolo[4,5-c]pyridine to provide the title compound.

LC/MS: m/z=318 (MH$^+$)

The stereo-isomers of this compound are separated. The S-configurated compound has a different activity than the R-configurated compound.

Example 80

(6-Bromo-pyrazolo[1,5-a]pyrimidin-2-yl)-(2-chloro-4-methyl-6,7-dihydro-4H-oxazolo[4,5-c]pyridin-5-yl)-methanone

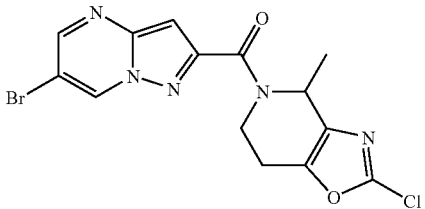

(6-Bromo-pyrazolo[1,5-a]pyrimidin-2-yl)-(7-methyl-1,4,5,7-tetrahydro-pyrrolo[2,3-c]pyridin-6-yl)-methanone is reacted with 2-chloro-4-methyl-4,5,6,7-tetrahydrooxazolo[4,5-c]pyridine to provide the title compound.

LC/MS: m/z=397 (MH$^+$)

The stereo-isomers of this compound are separated. The S-configurated compound has a different activity than the R-configurated compound.

Example 81

(6-Bromo-pyrazolo[1,5-a]pyrimidin-2-yl)-(2,4-dimethyl-6,7-dihydro-4H-oxazolo[4,5-c]pyridin-5-yl)-methanone

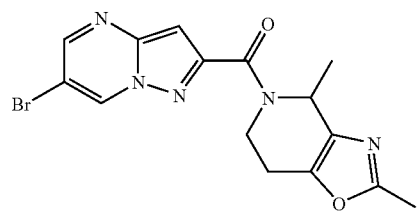

(6-Bromo-pyrazolo[1,5-a]pyrimidin-2-yl)-(7-methyl-1,4,5,7-tetrahydro-pyrrolo[2,3-c]pyridin-6-yl)-methanone is reacted with 2,4-dimethyl-4,5,6,7-tetrahydro-oxazolo[4,5-c]pyridine to provide the title compound.

LC/MS: m/z=377 (MH$^+$)

The stereo-isomers of this compound are separated. The S-configurated compound has a different activity than the R-configurated compound.

Example 82

(6-Bromo-pyrazolo[1,5-a]pyrimidin-2-yl)-(4-methyl-2-trifluoromethyl-6,7-dihydro-4H-oxazolo[4,5-c]pyridin-5-yl)-methanone

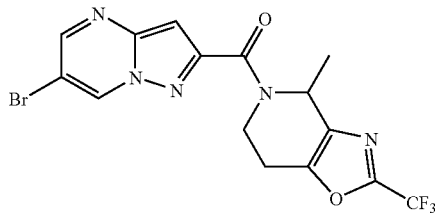

(6-Bromo-pyrazolo[1,5-a]pyrimidin-2-yl)-(7-methyl-1,4,5,7-tetrahydro-pyrrolo[2,3-c]pyridin-6-yl)-methanone is reacted with 4-methyl-2-trifluoromethyl-4,5,6,7-tetrahydrooxazolo[4,5-c]pyridine to provide the title compound.

LC/MS: m/z=431 (MH$^+$)

The stereo-isomers of this compound are separated. The S-configurated compound has a different activity than the R-configurated compound.

Example 83

(6-Bromo-pyrazolo[1,5-a]pyrimidin-2-yl)-(2-methoxy-4-methyl-6,7-dihydro-4H-oxazolo[4,5-c]pyridin-5-yl)-methanone

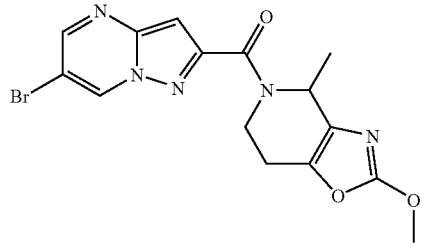

(6-Bromo-pyrazolo[1,5-a]pyrimidin-2-yl)-(7-methyl-1,4,5,7-tetrahydro-pyrrolo[2,3-c]pyridin-6-yl)-methanone is reacted with 2-methoxy-4-methyl-4,5,6,7-tetrahydrooxazolo[4,5-c]pyridine to provide the title compound.

LC/MS: m/z=393 (MH$^+$).

The stereo-isomers of this compound are separated. The S-configurated compound has a different activity than the R-configurated compound.

The pure stereoisomeric forms (including optical isomers) of the compounds and the intermediates of this invention may be obtained by the application of art-known procedures. Diastereomers may be separated by physical separation methods such as selective crystallization and chromatographic techniques, e.g. liquid chromatography using chiral stationary phases. Enantiomers (optically active isomers) may be separated from each other by selective crystallization of their diastereomeric salts with optically active acids. Alternatively, enantiomers may be separated by chromatographic techniques using chiral stationary phases.

Said pure stereoisomeric forms may also be derived from the corresponding pure stereoisomeric form of appropriate starting materials, provided that the reaction occur stereoselectively. Stereoisomeric forms of Formula (I) are included within the scope of this invention.

For therapeutic use, salts of the compounds of Formula I are those wherein the counterion is pharmaceutically acceptable. However, salts of acids and bases, which are non-pharmaceutically acceptable, may also find use, for example, in the preparation and purification of pharmaceutically acceptable compounds. All salts whether pharmaceutically acceptable or not are included within the ambit of the present invention.

The pharmaceutically acceptable salts as mentioned above are meant to comprise the therapeutically active non-toxic salt forms, which the compounds of formula I are able to form. The latter can conveniently be obtained by treating the base form with such appropriate acids as inorganic acids, e.g. hydrohalic acids such as hydrochloric, hydrobromic and the like; sulfuric acid; nitric acid; phosphoric acid and the like; or organic acids such as acetic, propanoic, hydroxyacetic, 2-hydroxypropanoic, oxopropanoic, oxalic, malonic, succinic, maleic, fumaric, malic, tartaric, 2-hydroxy-1,2,3-propanetricarboxylic, methanesulfonic, ethanesulfonic, benzenesulfonic, 4-methylbenzenesulfonic, cyclohexanesulfonic, 2-hydroxybenzoic, 4-amino-2-hydroxybenzoic and the like acids. Conversely, the salt form can be converted by treatment with alkali into the free base form.

Pharmaceutical Compositions

The active ingredients of formula (I) of the invention, together with one or more conventional adjuvants, carriers, or diluents, may be placed into the form of pharmaceutical compositions and unit dosages thereof, and in such form may be employed as solids, such as coated or uncoated tablets or filled capsules, or liquids, such as solutions, suspensions, emulsions, elixirs, or capsules filled with the same, all for oral use; in the form of suppositories or capsules for rectal administration or in the form of sterile injectable solutions for parenteral (including intravenous or subcutaneous) use.

Such pharmaceutical compositions and unit dosage forms thereof may comprise conventional or new ingredients in conventional or special proportions, with or without additional active compounds or principles, and such unit dosage forms may contain any suitable effective amount of the active ingredient commensurate with the intended daily dosage range to be employed. Tablets containing one (1) to one hundred (100) milligrams of active ingredient or, more broadly, zero point five (0.5) to five hundred (500) milligrams per tablet, are accordingly suitable representative unit dosage forms.

The term "carrier" applied to pharmaceutical compositions of the invention refers to a diluent, excipient, or vehicle with which an active compound is administered. Such pharmaceutical carriers can be sterile liquids, such as water, saline solutions, aqueous dextrose solutions, aqueous glycerol solutions, and oils, including those of petroleum, animal, vegetable or synthetic origin, such as peanut oil, soybean oil, mineral oil, sesame oil and the like. A. R. Gennaro, 20$^{th}$ Edition, describes suitable pharmaceutical carriers in "Remington: The Science and Practice of Pharmacy".

Method of Treating and Pharmaceutical Formulations

Due to their high degree of activity and their low toxicity, together presenting a most favorable therapeutic index, the active principles of formula (I) of the invention may be administered to a subject, e.g., a living animal (including a human) body, in need thereof, for the treatment, alleviation, or amelioration, palliation, or elimination of an indication or condition which is susceptible thereto, or representatively of an indication or condition set forth elsewhere in this application, preferably concurrently, simultaneously, or together with one or more pharmaceutically-acceptable excipients, carriers, or diluents, especially and preferably in the form of a pharmaceutical composition thereof, whether by oral, rectal, or parental (including intravenous and subcutaneous) or in some cases even topical route, in an effective amount. Suitable dosage ranges are 1-1000 milligrams daily, preferably 10-500 milligrams daily, and especially 50-500 milligrams daily, depending as usual upon the exact mode of administration, form in which administered, the indication toward which the administration is directed, the subject involved and the body weight of the subject involved, and the preference and experience of the physician or veterinarian in charge.

The term "therapeutically effective" applied to dose or amount refers to that quantity of a compound or pharmaceutical composition that is sufficient to result in a desired activity upon administration to a living animal body in need thereof.

The active agents of formula (I) of the present invention may be administered orally, topically, parenterally, or mucosally (e.g., buccally, by inhalation, or rectally) in dosage unit formulations containing conventional non-toxic pharmaceutically acceptable carriers. It is usually desirable to use the oral route. The active agents may be administered orally in the form of a capsule, a tablet, or the like (see Remington: The Science and Practice of Pharmacy, 20th Edition). The orally administered medicaments may be administered in the form of a time-controlled release vehicle, including diffusion-controlled systems, osmotic devices, dissolution-controlled matrices, and erodible/degradable matrices.

For oral administration in the form of a tablet or capsule, the active drug component of formula (I) may be combined with a non-toxic, pharmaceutically acceptable excipients such as binding agents (e.g., pregelatinized maize starch, polyvinylpyrrolidone or hydroxypropyl methylcellulose); fillers (e.g., lactose, sucrose, glucose, mannitol, sorbitol and other reducing and non-reducing sugars, microcrystalline cellulose, calcium sulfate, or calcium hydrogen phosphate); lubricants (e.g., magnesium stearate, talc, or silica, steric acid, sodium stearyl fumarate, glyceryl behenate, calcium stearate, and the like); disintegrants (e.g., potato starch or sodium starch glycolate); or wetting agents (e.g., sodium lauryl sulphate), coloring and flavoring agents, gelatin, sweeteners, natural and synthetic gums (such as acacia, tragacanth or alginates), buffer salts, carboxymethylcellulose, polyethyleneglycol, waxes, and the like. For oral administration in liquid form, the drug components may be combined with non-toxic, pharmaceutically acceptable inert carriers (e.g., ethanol, glycerol, water), suspending agents (e.g., sorbitol syrup, cellulose derivatives or hydrogenated edible fats), emulsifying agents (e.g., lecithin or acacia), non-aqueous vehicles (e.g., almond oil, oily esters, ethyl alcohol or fractionated vegetable oils), preservatives (e.g., methyl or propyl-p-hydroxybenzoates or sorbic acid), and the like. Stabilizing agents such as antioxidants (BHA, BHT, propyl gallate, sodium ascorbate, citric acid) may also be added to stabilize the dosage forms.

The tablets containing as active compound a compound of formula (I) may be coated by methods well known in the art. The compositions of the invention containing as active compound a compound of formula (I) may be also introduced in beads, microspheres or microcapsules, e.g., fabricated from polyglycolic acid/lactic acid (PGLA). Liquid preparations for oral administration may take the form of, for example, solutions, syrups, emulsions or suspensions, or they may be presented as a dry product for reconstitution with water or other suitable vehicle before use. Preparations for oral administration may be suitably formulated to give controlled or postponed release of the active compound.

The active drugs of formula (I) may also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines, as is well known.

Drugs of the invention containing as active compound a compound of formula (I) may also be delivered by the use of monoclonal antibodies as individual carriers to which the compound molecules are coupled. Active drugs may also be coupled with soluble polymers as targetable drug carriers. Such polymers include polyvinyl-pyrrolidone, pyran copolymer, polyhydroxy-propyl methacrylamide-phenol, polyhydroxy-ethyl-aspartamide-phenol, or polyethyleneoxide-polylysine substituted with palmitoyl residues. Furthermore, active drug may be coupled to a class of biodegradable polymers useful in achieving controlled release of a drug, for example, polylactic acid, polyglycolic acid, copolymers of polylactic and polyglycolic acid, polyepsilon caprolactone, polyhydroxybutyric acid, polyorthoesters, polyacetals, polyhydropyrans, polycyanoacrylates, and cross-linked or amphipathic block copolymers of hydrogels.

For administration by inhalation, the therapeutics according to the present invention containing as active compound a compound of formula (I) may be conveniently delivered in the form of an aerosol spray presentation from pressurized packs or a nebulizer, with the use of a suitable propellant, e.g., dichlorodifluoromethane, trichlorofluoromethane, dichlorotetra-fluoroethane, carbon dioxide, or other suitable gas. In the case of a pressurized aerosol, the dosage unit may be determined by providing a valve to deliver a metered amount. Capsules and cartridges of, e.g., gelatin for use in an inhaler or insufflator can be formulated containing a powder mix of the compound and a suitable powder base such as lactose or starch.

The formulations of the invention containing a compound of formula (I) may be delivered parenterally, i.e., by intravenous (i.v.), intracerebroventricular (i.c.v.), subcutaneous (s.c.), intraperitoneal (i.p.), intramuscular (i.m.), subdermal (s.d.), or intradermal (i.d.) administration, by direct injection, via, for example, bolus injection or continuous infusion. Formulations for injection can be presented in unit dosage form, e.g., in ampoules or in multi-dose containers, with an added preservative. The compositions can take such forms as excipients, suspensions, solutions, or emulsions in oily or aqueous vehicles, and can contain formulatory agents such as suspending, stabilizing and/or dispersing agents. Alternatively, the active ingredient can be in powder form for reconstitution with a suitable vehicle, e.g., sterile pyrogen-free water, before use.

Compositions of the present invention containing a compound of formula (I) may also be formulated for rectal administration, e.g., as suppositories or retention enemas (e.g., containing conventional suppository bases such as cocoa butter or other glycerides).

The compositions containing a compound of formula (I) may, if desired, be presented in a pack or dispenser device, which may contain one or more unit dosage forms containing the active ingredient and/or may contain different dosage levels to facilitate dosage titration. The pack may, for example, comprise metal or plastic foil, such as a blister pack. The pack or dispenser device may be accompanied by instructions for administration. Compositions of the invention formulated in a compatible pharmaceutical carrier may also be prepared, placed in an appropriate container, and labeled for treatment of an indicated condition.

As disclosed herein, the dose of the components in the compositions of the present invention is determined to ensure that the dose administered continuously or intermittently will not exceed an amount determined after consideration of the results in test animals and the individual conditions of a patient. A specific dose naturally varies depending on the dosage procedure, the conditions of a patient or a subject animal such as age, body weight, sex, sensitivity, feed, dosage period, drugs used in combination, seriousness of the disease. The appropriate dose and dosage times under certain conditions can be determined by the test based on the above-described indices but may be refined and ultimately decided according to the judgment of the practitioner and each patient's circumstances (age, general condition, severity of symptoms, sex, etc.) according to standard clinical techniques.

Toxicity and therapeutic efficacy of the compositions of the invention can be determined by standard pharmaceutical procedures in experimental animals, e.g., by determining the $LD_{50}$ (the dose lethal to 50% of the population) and the $ED_{50}$ (the dose therapeutically effective in 50% of the population). The dose ratio between therapeutic and toxic effects is the therapeutic index and it may be expressed as the ratio $ED_{50}/LD_{50}$. Compositions that exhibit large therapeutic indices are preferred.

Examples of Representative Pharmaceutical Compositions

With the aid of commonly used solvents, auxiliary agents and carriers, the reaction products can be processed into tablets, coated tablets, capsules, drip solutions, suppositories, injection and infusion preparations, and the like and can be therapeutically applied by the oral, rectal, parenteral, and additional routes. Representative pharmaceutical compositions according to the present invention follow:

(a) Tablets suitable for oral administration which contain the active ingredient, may be prepared by conventional tabletting techniques.

(b) For suppositories, any usual suppository base may be employed for incorporation thereinto by usual procedure of the active ingredient, such as a polyethyleneglycol which is a solid at normal room temperature but which melts at or about body temperature.

(c) For parental (including intravenous and subcutaneous) sterile solutions, the active ingredient together with conventional ingredients in usual amounts are employed, such as for example sodium chloride and double-distilled water q.s., according to conventional procedure, such as filtration, aseptic filling into ampoules or IV-drip bottles, and autoclaving for sterility.

Other suitable pharmaceutical compositions will be immediately apparent to one skilled in the art.

Formulation Examples for the Compounds of Formula (I)

The following examples are given by way of illustration. As active ingredient, the compound according to example 76 can be used.

Example 1

Tablet Formulation

A suitable formulation for a tablet containing 10 milligrams of active ingredient is as follows:

|  | mg |
|---|---|
| Active Ingredient | 10 |
| Lactose | 61 |
| Microcrystalline Cellulose | 25 |
| Talcum | 2 |
| Magnesium stearate | 1 |
| Colloidal silicon dioxide | 1 |

Example 2

Coated Tablet Formulation

Another suitable formulation for a tablet containing 100 mg is as follows:

|  | mg |
|---|---|
| Active Ingredient | 100 |
| Polyvinylpyrrolidone, crosslinked | 10 |
| Potato starch | 20 |
| Polyvinylpyrrolidone | 19 |
| Magnesium stearate | 1 |
| Microcrystalline Cellulose | 50 |

Film coated and colored.
The film coating material consists of:

|  | mg |
|---|---|
| Hypromellose | 10 |
| Microcryst. Cellulose | 5 |
| Talcum | 5 |
| Polyethylene glycol | 2 |
| Color pigments | 5 |

Example 3

Capsule Formulation

A suitable formulation for a capsule containing 50 milligrams of active ingredient is as follows:

|  | mg |
|---|---|
| Active Ingredient | 50 |
| Corn starch | 26 |
| Dibasic calcium phosphate | 50 |

-continued

|  | mg |
| --- | --- |
| Talcum | 2 |
| Colloidal silicon dioxide | 2 |

This formulation is filled in a gelatin capsule.

Example 4

Solution for Injection

A suitable formulation for an injectable solution is as follows:

| Active Ingredient | mg | 10 |
| --- | --- | --- |
| Sodium chloride | mg | q.s. |
| Water for Injection | ml | add 1.0 |

Example 5

Liquid Oral Formulation

A suitable formulation for 1 liter of an oral solution containing 2 milligrams of active ingredient in one milliliter of the mixture is as follows:

|  | mg |
| --- | --- |
| Active Ingredient | 2 |
| Saccharose | 250 |
| Glucose | 300 |
| Sorbitol | 150 |
| Orange flavor | 10 |
| Colorant | q.s. |
| Purified water | add 1000 ml |

Example 6

Liquid Oral Formulation

Another suitable formulation for 1 liter of a liquid mixture containing 20 milligrams of active ingredient in one milliliter of the mixture is as follows:

|  | g |
| --- | --- |
| Active Ingredient | 20.00 |
| Tragacanth | 7.00 |
| Glycerol | 50.00 |
| Saccharose | 400.00 |
| Methylparaben | 0.50 |
| Propylparaben | 0.05 |
| Black currant-flavor | 10.00 |
| Soluble Red color | 0.02 |
| Purified water | add 1000 ml |

Example 7

Liquid Oral Formulation

Another suitable formulation for 1 liter of a liquid mixture containing 2 milligrams of active ingredient in one milliliter of the mixture is as follows:

|  | g |
| --- | --- |
| Active Ingredient | 2 |
| Saccharose | 400 |
| Bitter orange peel tincture | 20 |
| Sweet orange peel tincture | 15 |
| Purified water | add 1000 ml |

Example 8

Aerosol Formulation 180 g of the aerosol solution contain:

|  | g |
| --- | --- |
| Active Ingredient | 10 |
| Oleic acid | 5 |
| Ethanol | 81 |
| Purified Water | 9 |
| Tetrafluoroethane | 75 |

15 ml of the solution are filled into aluminum aerosol cans, capped with a dosing valve, purged with 3.0 bar.

Example 9

Trans-Dermal-System Formulation 100 g of the solution contain:

|  | g |
| --- | --- |
| Active Ingredient | 10.0 |
| Ethanol | 57.5 |
| Propyleneglycol | 7.5 |
| Dimethylsulfoxide | 5.0 |
| Hydroxyethylcellulose | 0.4 |
| Purified water | 19.6 |

1.8 ml of the solution is placed on a fleece covered by an adhesive backing foil. The system is closed by a protective liner which will be removed before use.

Example 10

Nanoparticle Formulation 10 g of polybutylcyanoacrylate nanoparticles contain:

|  | g |
| --- | --- |
| Active Ingredient | 1.00 |
| Poloxamer | 0.10 |
| Butylcyanoacrylate | 8.75 |
| Mannitol | 0.10 |
| Sodium chloride | 0.05 |

Polybutylcyanoacrylate nanoparticles are prepared by emulsion polymerization in a water/0.1 N HCl/ethanol mixture as polymerizsation medium. The nanoparticles in the suspension are finally lyophilized under vacuum.

Example 11

Suspension Formulation 1.0 g of the suspension contains the following:

|  | g |
| --- | --- |
| Active Ingredient | 0.10 |
| Hypromellose | 0.01 |
| Purified water | Ad 1.0 g |

Hypromellose is dispersed in water homogeneously with a high speed mixer/blender. After about one hour of hydration time of the hypromellose, the active ingredient is blended homogeneously into the hypromellose solution. The viscosity of the suspension can be adjusted by the amount of hypromellose, resulting in a very stable suspension with a very slow tendency of particle sedimentation and particle agglomeration.

Example 12

Solution for Injection 1.0 ml of solution contain:

|  | g |
| --- | --- |
| Active Ingredient | 0.05 |
| Mannitol | q.s. |
| DMSO | 0.10 |
| Water for injection | Ad 1.0 ml |

The active ingredient is dissolved in DMSO by stirring and heating (solution 1). The mannitol is dissolved in WFI (solution 2). After cooling down to room temperature solution 1 is mixed with solution 2 by continuous stirring. The solution is sterilized by filtration of by autoclaving.

Pharmacology

The active principles of the present invention, and pharmaceutical compositions containing them and method of treating therewith, are characterized by unique and advantageous properties. The compounds and pharmaceutical compositions thereof exhibit, in standard accepted reliable test procedures, the following valuable properties and characteristics Methods Binding Assays for the Characterization of mGluR5 Antagonists

[$^3$H]-MPEP (2-methyl-6-(phenylethynyl)pyridine) binding to transmembrane allosteric modulatory sites of mGluR5 receptors in cortical membranes.

Preparation of Rat Cortical Membranes:

Male Sprague-Dawley rats (200-250 g) are decapitated and their brains are removed rapidly. The cortex is dissected and homogenized in 20 volumes of ice-cold 0.32 M sucrose using a glass-Teflon homogenizer. The homogenate is centrifuged at 1000×g for 10 minutes. The pellet is discarded and the supernatant centrifuged at 20,000×g for 20 minutes. The resulting pellet is re-suspended in 20 volumes of distilled water and centrifuged for 20 minutes at 8000×g. Then the supernatant and the buffy coat are centrifuged at 48,000×g for 20 minutes in the presence of 50 mM Tris-HCl, pH 8.0. The pellet is then re-suspended and centrifuged two to three more times at 48,000×g for 20 minutes in the presence of 50 mM Tris-HCl, pH 8.0. All centrifugation steps are carried out at 4° C. After resuspension in 5 volumes of 50 mM Tris-HCl, pH 8.0 the membrane suspension is frozen rapidly at −80° C.

On the day of assay the membranes are thawed and washed four times by resuspension in 50 mM Tris-HCl, pH 8.0 and centrifugation at 48,000×g for 20 minutes and finally re-suspended in 50 mM Tris-HCl, pH 7.4. The amount of protein in the final membrane preparation (500-700 μg/ml) is determined according to the method of Lowry (Lowry O. H. et al. 1951. J. Biol. Chem. 193, 256-275).

[$^3$H]-MPEP Assay

Incubations are started by adding [$^3$H]-MPEP (50.2 Ci/mmol, 5 nM, Tocris, GB) to vials with 125-250 μg protein (total volume 0.25 ml) and various concentrations of the agents. Alternatively, assays are performed with [$^3$H]-MMPEP (2-(3-methoxyphenylethynyl)-6-methylpyridine hydrochloride) as radioligand. The incubations are continued at room temperature for 60 minutes (equilibrium is achieved under the conditions used). Non-specific binding is defined by the addition of unlabeled MPEP (10 μM). Incubations are terminated using a Millipore filter system. The samples are rinsed twice with 4 ml of ice-cold assay buffer over glass fibre filters (Schleicher & Schuell, Germany) under a constant vacuum. Following separation and rinse, the filters are placed into scintillation liquid (5 ml Ultima Gold, Perkin Elmer, Germany) and radioactivity retained on the filters is determined with a conventional liquid scintillation counter (Canberra Packard, Germany).

Characterization:

Specific binding is extremely high i.e. normally>85% and essentially independent of buffer (Tris or HEPES both 50 mM) and pH (6.8-8.9). There is a clear saturable protein dependence and the chosen protein concentration used for subsequent assays (500-700 μg/ml) is within the linear portion of this dependence. Cold MPEP displaces hot ligand with an $IC_{50}$ of 11.2±0.64 nM. The $K_d$ of [$^3$H]-MPEP of 13.6 nM is determined by Scatchard analysis and used according to the Cheng Prussoff relationship to calculate the affinity of displacers as $K_d$ values ($IC_{50}$ of cold MPEP equates to a $K_i$ of 8.2 nM). $B_{max}$ is 0.56 pm/mg protein.

Functional Assays of mGluR5 Receptors

Cytosolic Calcium Studies with Stably Transfected Cells:

Chinese hamster ovary cells (CHO-K1 cells), stably transfected for inducible expression of a human metabotropic glutamate receptor mGluR5, are seeded into black clear bottom 96 well plates at a density of 35.000 cells per well. The standard growth medium used (Dulbecco's modified Eagle Medium, DMEM plus L-proline) contains the appropriate inducer isopropyl-β-D-thiogalactopyranosid (IPTG) to achieve optimal receptor expression. One day after seeding the growth medium is exchanged for reconstituted Ca-Kit (Molecular Devices, USA) and incubated for one hour. Ca-Kit is reconstituted in an assay buffer containing 20 mM HEPES pH 7.4, glutamic-pyruvate transaminase, pyridoxal phosphate and sodium pyruvate in Hank's balanced salt solution (HBBS). Agonistic compounds to the receptor elicit increases in cytosolic calcium which can be measured as increases in fluorescence signals by use of a fluorescence imaging plate reader (Molecular Devices). To analyze their potency to modulate the Ca-response test compounds, dissolved in a final DMSO concentration of 0.5%, are added on-line 5 minutes before the agonist to the receptor (L-quisqualic acid at a concentration giving 80% of the maximal signal).

Astrocyte Culture:

Primary astrocyte cultures are prepared from cortices of newborn rats as described by Booher and Sensenbrenner (1972, Neurobiology 2(3):97-105). Briefly, Sprague-Dawley rat pups (2-4 d old) are decapitated and neocortices are dissected, disintegrated with a nylon filter (pore size 80 µm) and carefully triturated. The cell suspension is plated on poly-D-lysine pre-coated flasks (Costar, Netherlands) and cultivated in Dulbecco's Modified Eagle's Medium (DMEM, Invitrogen, Germany) supplemented with 10% foetal calf serum (FCS, Sigma, Germany), 4 mM glutamine and 50 µg/ml gentamycin (both Biochrom, Germany) at 37° C. in a humidified atmosphere of 5% $CO_2$/95% air for 7 d with exchanging the medium at day 2 and 6.

After 7 days in vitro (DIV), cells are shaken overnight at 250 rpm to remove oligodendrocytes and microglia. The next day, astrocytes are rinsed twice with CMF-PBS (calcium- and magnesium-free phosphate buffered saline, Biochrom, Germany), trypsinized and subplated on poly-D-lysine pre-coated 96-well plates (Greiner, Germany) at a density of 40,000 cells/well. 24 h after establishing the secondary culture the astrocytes are rinsed with $PBS^{++}$ (phosphate buffered saline, Biochrom, Germany) and fed with astrocyte-defined medium (ADM) consisting of DMEM containing 1×G5-supplement (Invitrogen, Germany), 0.5 µg/ml heparan sulfate, and 1.5 µg/ml fibronectin (both Sigma, Germany) (Miller et al., (1993) Brain Res. 618(1):175-8). 3 d later the medium is exchanged and the cells incubated for another 2-3 d, so that at the time of experiments astrocytes are 14-15 DIV.

Immunocytochemistry

Immunostaining is performed to confirm the presence of astrocytic markers such as the glial fibrillary acidic protein (GFAP) as well as to monitor the expression of mGluR5 receptors.

Cytosolic Calcium Studies with Astrocytes:

The increase of cytosolic calcium after stimulation with the mGluR5 agonist L-quisqualate is measured using a fluorometric imaging plate reader (FLIPR) and the Ca-Kit (both Molecular Devices). Prior to addition of agonist or antagonist the medium is aspirated and cells are loaded for 2 h at RT with 150 µl of loading buffer consisting of Ca-sensitive dye reconstituted in sodium chloride (123 mM), potassium chloride (5.4 mM), magnesium chloride (0.8 mM), calcium chloride (1.8 mM), D-glucose (15 mM), and HEPES (20 mM), pH 7.3. Subsequently, plates are transferred to FLIPR to detect calcium increase with the addition of L-quisqualate (100 nM) measured as relative fluorescence units (RFU). If antagonists are tested, these compounds are pre-incubated for 10 minutes at RT before addition of the respective agonist.

For positive modulators, concentration-response curves for quisqualate are performed in the presence and absence of 10 µM modulator to determine the extent of potentiation/agonist potency increase. Thereafter, concentration-response curves for the positive modulator are performed in the presence of a fixed concentration of quisqualate showing the biggest window for potentiation (normally 10-30 nM).

Data Analysis

The fluorescence signal increase after addition of agonist reflects the increase of cytosolic calcium. Inconsistencies in the amount of cells per well are normalised by using the spatial uniformity correction of the FLIPR software. The mean of replicated temporal data (n=3-5) is calculated and used for graphical representation. For the evaluation of the pharmacology, the calcium changes in response to different concentrations of agonist or antagonist are determined using a maximum minus minimum (MaxMin) calculation.

All responses (RFU-values) are determined as percentage of control (=maximum response). $EC_{50}$ and $IC_{50}$ are calculated according to the logistic equation using GraFit 5.0 (Erithacus Software, GB) or Prism 4.0 (GraphPad Software, USA). The compounds of the present invention have a potency ($IC_{50}$) within a range of about 0.5 nM to about 100 µM.

Results for representative compounds of the invention are shown in Tables A1-A3.

In conclusion, from the foregoing, it is apparent that the present invention provides novel and valuable applications and uses of the compounds of the present invention, which compounds comprise the active principle according to the present invention, as well as novel pharmaceutical compositions thereof and methods of preparation thereof and of treating therewith.

The high order of activity of the active agent of the present invention and compositions thereof, as evidenced by the tests reported, is indicative of utility based on its valuable activity in human beings as well as in lower animals. Clinical evaluation in human beings has not been completed. It will be clearly understood that the distribution and marketing of any compound or composition falling within the scope of the present invention for use in human beings will of course have to be predicated upon prior approval by governmental agencies which are responsible for and authorized to pass judgment on such questions.

The instant compounds of formula (I) represent a novel class of mGluR5 modulators. In view of their potency, they will be useful therapeutics in a wide range of disorders, in particular CNS disorders, which involve excessive glutamate induced excitation.

These compounds accordingly find application in the treatment of the disorders of a living animal body, especially a human, as listed earlier in the description.

These compounds also find application in the treatment of indications in a living animal body, especially a human, wherein a particular condition does not necessarily exist but wherein a particular physiological parameter may be improved through administration of the instant compounds, including cognitive enhancement.

Neuroprotection as well as cognitive enhancement can also be achieved by combining application of these compounds with NMDA receptor antagonists like Memantine and Neramexane.

The method-of-treating a living animal body with a compound of the invention, for the inhibition of progression or alleviation of the selected ailment therein, is as previously stated by any normally-accepted pharmaceutical route, employing the selected dosage which is effective in the alleviation of the particular ailment desired to be alleviated. Use of the compounds of the present invention in the manufacture of a medicament for the treatment of a living animal for inhibition of progression or alleviation of selected ailments or conditions, particularly ailments or conditions susceptible to treatment with a Group I mGluR modulator is carried out in the usual manner comprising the step of admixing an effective amount of a compound of the invention with a pharmaceutically-acceptable diluent, excipient, or carrier, and the method-of-treating, pharmaceutical compositions, and use of a compound of the present invention in the manufacture of a medicament.

Representative pharmaceutical compositions prepared by admixing the active ingredient with a suitable pharmaceutically-acceptable excipient, diluent, or carrier, include tablets, capsules, solutions for injection, liquid oral formulations, aerosol formulations, TDS formulations, and nanoparticle formulations, thus to produce medicaments for oral, injectable, or dermal use, also in accord with the foregoing.

TABLE A1

(Cytosolic Calcium studies with stably transfected cells)

| Compound | Chemical Name | mGluR5_FLIPR_h_CHO_NAM_IC50 [µM] |
|---|---|---|
| | 6-bromo-2-[(4-methyl-6,7-dihydrothieno[3,2-c]pyridin-5(4H)-yl)carbonyl]pyrazolo[1,5-a]pyrimidine; | 0.0807 |
| | (6-Bromo-pyrazolo[1,5-a]pyrimidin-2-yl)-(2,4-dimethyl-6,7-dihydro-4H-thieno[3,2-c]pyridin-5-yl)-methanone; | 0.1044 |
| | (6-Chloro-pyrazolo[1,5-a]pyrimidin-2-yl)-(2,4-dimethyl-6,7-dihydro-4H-thieno[3,2-c]pyridin-5-yl)-methanone; | 0.0929 |
| | (6-Bromo-pyrazolo[1,5-a]pyrimidin-2-yl)-(4-ethyl-6,7-dihydro-4H-thieno[3,2-c]pyridin-5-yl)-methanone; | 0.0636 |
| | (6-Chloro-pyrazolo[1,5-a]pyrimidin-2-yl)-(4-ethyl-6,7-dihydro-4H-thieno[3,2-c]pyridin-5-yl)-methanone; | 0.0820 |
| | (6-Chloro-pyrazolo[1,5a]pyrimidin-2-yl)-(4-methyl-6,7-dihydro-4H-thieno[3,2-c]pyridin-5-yl)-methanone; | 0.0440 |

TABLE A1-continued (Cytosolic Calcium studies with stably transfected cells)

| Compound | | Chemical Name | mGluR5_FLIPR_h_CHO_NAM_IC50 [µM] |
|---|---|---|---|
| | | 6-chloro-2-[(4-methyl-6,7-dihydrofuro[3,2-c]pyridin-5(4H)-yl)carbonyl]pyrazolo[1,5-a]pyrimidine; | 0.2055 |
| | | 6-bromo-2-[(4-methyl-6,7-dihydrofuro[3,2-c]pyridin-5(4H)-yl)carbonyl]pyrazolo[1,5-a]pyrimidine; | 0.1072 |
| | Chiral | (6-Bromo-pyrazolo[1,5-a]pyrimidin-2-yl)-(4-methyl-6,7-dihydro-4H-thieno[3,2-c]pyridin-5-yl)-methanone; R-isomer; optical rotation: −22.2°; | 0.0234 |
| | | (6-Bromo-pyrazolo[1,5-a]pyrimidin-2-yl)-(2,4-dimethyl-6,7-dihydro-4H-furo[3,2-c]pyridin-5-yl)-methanone; | 0.1473 |
| | Chiral | (6-Bromo-pyrazolo[1,5a]pyrimidin-2-yl)-(4-methyl-6,7-dihydro-4H-thieno[3,2-c]pyridin-5-yl)-methanone; S-isomer; optical rotation: +22.2°. | 4.4167 |

TABLE A2

(Astrocyte culture test)

| Compound | Chemical Name | mGluR5_FLIPR_r_rpA_ IC50 [µM] |
|---|---|---|
| | 6-bromo-2-[(4-methyl-6,7-dihydrothieno[3,2-c]pyridin-5(4H)-yl)carbonyl]pyrazolo[1,5-a]pyrimidine | 0.023 |
| | (6-Bromo-pyrazolo[1,5-a]pyrimidin-2-yl)-(2,4-dimethyl-6,7-dihydro-4H-thieno[3,2-c]pyridin-5-yl)-methanone | 0.0228 |
| | (6-Chloro-pyrazolo[1,5-a]pyrimidin-2-yl)-(2,4-dimethyl-6,7-dihydro-4H-thieno[3,2-c]pyridin-5-yl)-methanone | 0.021 |
| | (6-Bromo-pyrazolo[1,5-a]pyrimidin-2-yl)-(4-ethyl-6,7-dihydro-4H-thieno[3,2-c]pyridin-5-yl)-methanone | 0.021 |
| | (6-Chloro-pyrazolo[1,5-a]pyrimidin-2-yl)-(4-ethyl-6,7-dihydro-4H-thieno[3,2-c]pyridin-5-yl)-methanone | 0.021 |
| | (6-Chloro-pyrazolo[1,5-a]pyrimidin-2-yl)-(4-methyl-6,7-dihydro-4H-thieno[3,2-c]pyridin-5-yl)-methanone | 0.024 |

TABLE A2-continued (Astrocyte culture test)

| Compound | Chemical Name | mGluR5_FLIPR_r_rpA_ IC50 [μM] |
|---|---|---|
| | 6-chloro-2-[(4-methyl-6,7-dihydrofuro[3,2-c]pyridin-5(4H)-yl)carbonyl]pyrazolo[1,5-a]pyrimidine | 0.064 |
| | 6-bromo-2-[(4-methyl-6,7-dihydrofuro[3,2-c]pyridin-5(4H)-yl)carbonyl]pyrazolo[1,5-a]pyrimidine | 0.0805 |
| Chiral | (6-Bromo-pyrazolo[1,5-a]pyrimidin-2-yl)-(4-methyl-6,7-dihydro-4H-thieno[3,2-c]pyridin-5-yl)-methanone (R-isomer) | 0.02 |
| | (6-Bromo-pyrazolo[1,5-a]pyrimidin-2-yl)-(2,4-dimethyl-6,7-dihydro-4H-furo[3,2-c]pyridin-5-yl)-methanone | 0.036 |

TABLE A3

(Results from $^3$H-MPEP-Assay)

| Compound | Chemical Name | mGluR5_M_MPEP_r_CTX IC50 [μM] |
|---|---|---|
| | 6-bromo-2-[(4-methyl-6,7-dihydrothieno[3,2-c]pyridin-5(4H)-yl)carbonyl]pyrazolo[1,5-a]pyrimidine | 0.08 |

TABLE A3-continued (Results from ³H-MPEP-Assay)

| Compound | Chemical Name | mGluR5_M_MPEP_r_CTX IC50 [μM] |
|---|---|---|
| 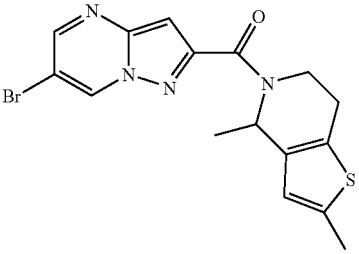 | (6-Bromo-pyrazolo[1,5-a]pyrimidin-2-yl)-(2,4-dimethyl-6,7-dihydro-4H-thieno[3,2-c]pyridin-5-yl)-methanone | 0.012 |
| 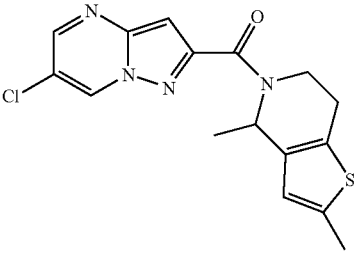 | (6-Chloro-pyrazolo[1,5-a]pyrimidin-2-yl)-(2,4-dimethyl-6,7-dihydro-4H-thieno[3,2-c]pyridin-5-yl)-methanone | 0.02 |
| 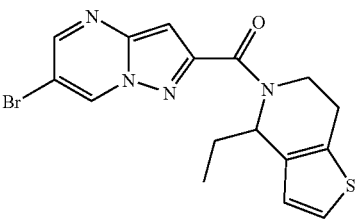 | (6-Bromo-pyrazolo[1,5-a]pyrimidin-2-yl)-(4-ethyl-6,7-dihydro-4H-thieno[3,2-c]pyridin-5-yl)-methanone | 0.117 |
| 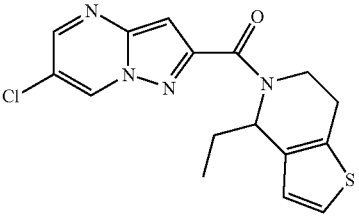 | (6-Chloro-pyrazolo[1,5-a]pyrimidin-2-yl)-(4-ethyl-6,7-dihydro-4H-thieno[3,2-c]pyridin-5-yl)-methanone | 0.15 |
| 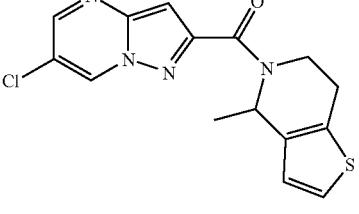 | (6-Chloro-pyrazolo[1,5-a]pyrimidin-2-yl)-(4-methyl-6,7-dihydro-4H-thieno[3,2-c]pyridin-5-yl)-methanone | 0.055 |
| 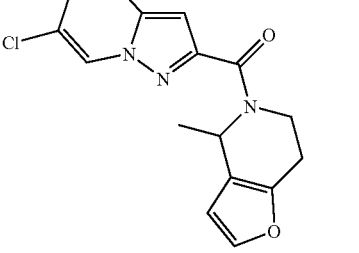 | 6-chloro-2-[(4-methyl-6,7-dihydrofuro[3,2-c]pyridin-5(4H)-yl)carbonyl]pyrazolo[1,5-a]pyrimidine | 0.11 |

TABLE A3-continued (Results from ³H-MPEP-Assay)

| Compound | | Chemical Name | mGluR5_M_MPEP_r_CTX IC50 [µM] |
|---|---|---|---|
| | | 6-bromo-2-[(4-methyl-6,7-dihydrofuro[3,2-c]pyridin-5(4H)-yl)carbonyl]pyrazolo[1,5-a]pyrimidine | 0.214 |
| 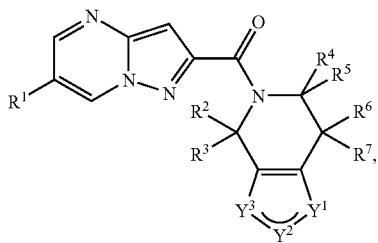 | Chiral | (6-Bromo-pyrazolo[1,5-a]pyrimidin-2-yl)-(4-methyl-6,7-dihydro-4H-thieno[3,2-c]pyridin-5-yl)-methanone (R-isomer) | 0.01 |
| | | (6-Bromo-pyrazolo[1,5-a]pyrimidin-2-yl)-(2,4-dimethyl-6,7-dihydro-4H-furo[3,2-c]pyridin-5-yl)-methanone | 0.017 |

We claim:

1. A compound selected from those of formula (I)

(I)

wherein
$Y^1$, $Y^2$ and $Y^3$ independently represent $CR^{10}$, $CR^{11}$, $CR^{10}R^{11}$, $NR^{12}$, S or O, whereby at least one of $Y^1$, $Y^2$ and $Y^3$ represents $CR^{10}$;
or $Y^1$ and $Y^2$ together represent a group $R^{10}C=N$; $R^{10}C=CR^{11}$; $R^{10}R^{11}C-C(=O)$ or $R^{12}N-(C=O)$;
or $Y^2$ and $Y^3$ together represent a group $R^{10}C=N$; $R^{10}C=CR^{11}$; $R^{10}R^{11}C-C(=O)$ or $R^{12}N-(C=O)$;
$R^1$ represents chloro or bromo;
$R^2$ represents hydrogen, $C_{1-6}$alkyl, $C_{3-7}$cycloalkyl or trifluoromethyl;
$R^3$ represents hydrogen, $C_{1-6}$alkyl, $C_{3-7}$cycloalkyl or trifluoromethyl; or
$R^2$ and $R^3$ together with the carbon atom of the ring represent a carbonyl group;
$R^4$ represents hydrogen, $C_{1-6}$alkyl, $C_{3-7}$cycloalkyl or trifluoromethyl;
$R^5$ represents hydrogen, $C_{1-6}$alkyl, $C_{3-7}$cycloalkyl or trifluoromethyl; or
$R^4$ and $R^5$ together with the carbon atom of the ring represent a carbonyl group;
$R^6$ represents hydrogen, $C_{1-6}$alkyl, $C_{3-7}$cycloalkyl or trifluoromethyl;
$R^7$ represents hydrogen, $C_{1-6}$alkyl, $C_{3-7}$cycloalkyl or trifluoromethyl;
$R^6$ and $R^7$ together with the carbon atom of the ring represent a carbonyl group;
$R^2$ or $R^3$ together with $R^6$ or $R^7$ may form a bivalent radical of type $CH_2-CH_2$ or $CH_2-O$;
$R^{10}$ and $R^{11}$ independently represent hydrogen, halogen, amino, hydroxy, nitro, cyano, trifluoromethyl, trifluoromethoxy, aryl, $C_{1-6}$alkyl, $C_{3-7}$-cycloalkyl, $C_{2-6}$alkenyl, $C_{2-6}$alkynyl, $C_{1-6}$alkoxy, $C_{3-7}$-cycloalkyloxy, $C_{2-6}$alkenyloxy, $C_{2-6}$alkynyloxy, heteroaryl, heterocyclyl, aryloxy, heteroaryloxy, heterocyclyloxy, $C_{1-6}$alkylamino, di-$C_{1-6}$ alkylamino, $C_{3-7}$-cycloalkylamino, di-$C_{3-7}$-cycloalkylamino, $C_{1-6}$alkyl-$C_{3-7}$-cycloalkylamino, $C_{2-6}$alkenylamino, $C_{2-6}$alkynylamino, di-$C_{2-6}$alkenylamino, di-$C_{2-6}$alkynylamino, $C_{1-6}$alkyl-$C_{2-6}$-alkenylamino, $C_{1-6}$alkyl-$C_{2-6}$-alkynylamino, $C_{2-6}$alkenyl-$C_{3-7}$-cycloalkylamino, $C_{2-6}$alkynyl-$C_{3-7}$-cycloalkylamino, $C_{2-6}$alkenyl-$C_{2-6}$-alkynylamino, arylamino, diarylamino, aryl-$C_{1-6}$alkylamino, aryl-$C_{2-6}$alkenylamino, aryl-$C_{2-6}$alkynylamino, aryl-$C_{3-7}$-cycloalkylamino, heteroarylamino, diheteroaryl-amino, heteroaryl-$C_{1-6}$alkylamino, heteroaryl-$C_{2-6}$alkenylamino, heteroaryl-$C_{2-6}$ alkynylamino, heteroaryl-$C_{3-7}$-cycloalkylamino, heteroarylarylamino, hetero-cyclylamino, diheterocyclylamino, heterocyclyl-$C_{1-6}$ alkylamino, heterocyclyl-$C_{2-6}$ alkenylamino, heterocyclyl-$C_{2-6}$alkynylamino, heterocyclyl-$C_{3-7}$-cycloalkylamino, heterocyclylarylamino, heterocyclylhetero-arylamino, acyl, acyloxy, acylamino, $C_{1-6}$ alkoxycarbonyl, $C_{3-7}$-cycloalkoxy-carbonyl, $C_{2-6}$alkenyloxycarbonyl, $C_{2-6}$alkynyl-oxycarbonyl, aryloxycarbonyl, heteroaryloxycarbonyl, heterocyclyloxycarbonyl, aminocarbonyl, $C_{1-6}$alkylamino-carbonyl, di-$C_{1-6}$alkylaminocarbonyl, $C_{3-7}$-cycloalkylaminocarbonyl, di-$C_{3-7}$-cycloalkylaminocarbonyl, $C_{1-6}$ alkyl-$C_{3-7}$-cycloalkylaminocarbonyl, $C_{2-6}$alkenyl-aminocarbonyl, $C_{2-6}$alkynylaminocarbonyl, di-$C_{2-6}$alkenylaminocarbonyl, di-$C_{2-6}$alkynylaminocarbonyl, $C_{1-6}$alkyl-$C_{2-6}$-alkenyl-aminocarbonyl, $C_{1-6}$ alkyl-$C_{2-6}$-alkynyl-aminocarbonyl, $C_{2-6}$alkenyl-$C_{3-7}$-cycloalkyl-aminocarbonyl, $C_{2-6}$alkynyl-$C_{3-7}$-cycloalkylaminocarbonyl, $C_{2-6}$alkenyl-$C_{2-6}$-alkynylaminocarbonyl, arylaminocarbonyl, diarylaminocarbonyl, aryl-$C_{1-6}$alkylaminocarbonyl, aryl-$C_{2-6}$alkenylaminocarbonyl, aryl-$C_{2-6}$alkynylaminocarbonyl, aryl-$C_{3-7}$-cycloalkylaminocarbonyl heteroarylaminocarbonyl, dihetero-arylaminocarbonyl, heteroaryl-$C_{1-6}$alkylaminocarbonyl, heteroaryl-$C_{2-6}$ alkenyl-aminocarbonyl, heteroaryl-$C_{2-6}$alkynylaminocarbonyl, heteroaryl-$C_{3-7}$-cycloalkyl-aminocarbonyl, heteroarylarylaminocarbonyl, heterocyclylaminocarbonyl, dihetero-cyclylamino-carbonyl, heterocyclyl-$C_{1-6}$alkylaminocarbonyl, heterocyclyl-$C_{2-6}$alkenylamino-carbonyl, heterocyclyl-$C_{2-6}$alkynylaminocarbonyl, heterocyclyl-$C_{3-7}$-cycloalkyl-aminocarbonyl, heterocyclylarylaminocarbonyl, heterocyclylhetero-arylamino-carbonyl, $C_{1-6}$alkylsulfinyl, $C_{3-7}$-cycloalkylsulfinyl, $C_{2-6}$alkenylsulfinyl, $C_{2-6}$-alkynylsulfinyl, arylsulfinyl, heteroarylsulfinyl, heterocyclylsulfinyl, $C_{1-6}$alkylsulfonyl, $C_{3-7}$-cycloalkylsulfonyl, $C_{2-6}$alkenylsulfonyl, $C_{2-6}$alkynylsulfonyl, arylsulfonyl, heteroarylsulfonyl, heterocyclylsulfonyl, $C_1$-$C_6$alkylsulfonylamino or arylsulfonylamino; and
$R^{12}$ represents hydrogen, $C_{1-6}$alkyl, $C_{3-7}$cycloalkyl, $C_{2-6}$alkenyl, $C_{2-6}$alkynyl, acyl, aryl, heteroaryl, heterocyclyl, $C_{1-6}$alkylamino-carbonyl, di-$C_{1-6}$alkylaminocarbonyl, $C_{1-6}$alkylsulfonyl, arylsulfonyl or heteroarylsulfonyl;
and optical isomers and pharmaceutically acceptable salts thereof.

2. The compound of claim 1, wherein $Y^2$ represents $CR^{10}$ and $Y^3$ represents $CR^{11}$ or wherein $Y^2$ and $Y^3$ together represent a group $R^{10}C=CR^{11}$.

3. The compound of claim 1, wherein $Y^2$ and $Y^3$ together represent a group $R^{10}C=CR^{11}$ and wherein $Y^1$ represents a group $CR^{11}$, $NR^{12}$, S or O.

4. The compound of claim 1, wherein one of the groups $Y^1$, $Y^2$ and $Y^3$ represents a group $CR^{10}$ and one of the groups $Y^1$, $Y^2$ and $Y^3$ represents a group $CR^{11}$, wherein one of the two radicals $R^{10}$ and $R^{11}$ represents hydrogen and the other represents a group from halogen, amino, hydroxy, nitro, cyano, trifluoromethyl, trifluoromethoxy, phenyl, $C_{1-6}$alkyl and $C_{1-6}$alkoxy.

5. The compound of claim 1, wherein $R^2$, $R^3$, $R^4$ and $R^5$ independently represent hydrogen, methyl, ethyl or trifluoromethyl; and
$R^6$ and $R^7$ independently represent hydrogen or methyl.

6. The compound of claim 1, wherein $R^2$, $R^3$, $R^4$, $R^5$, $R^6$ and $R^7$ independently represent hydrogen, methyl or ethyl.

7. The compound of claim 1, wherein $R^2$ and $R^3$ independently represent hydrogen, methyl or ethyl.

8. The compound of claim 1, wherein $R^2$ represents methyl or ethyl and $R^3$ represents hydrogen and which has at least one chiral carbon atom.

9. The compound of claim 1, wherein one of the groups $Y^2$ and $Y^3$ represents a group $CR^{10}$ and one of the groups $Y^2$ and $Y^3$ represents a group $CR^{11}$, wherein $R^{10}$ and $R^{11}$ represent hydrogen, methyl, fluoro, bromo, trifluoromethyl or phenyl, and wherein $Y^1$ represents a group $CR^{11}$, NH, S or O.

10. The compound of claim 1, wherein $R^1$ represents chloro.

11. The compound of claim 1, wherein $R^1$ represents bromo.

12. The compound of claim 1, wherein $Y^1$ represents O, S or NH.

13. The compound of claim 1, wherein $Y^1$ represents O or S, and $Y^2$ and $Y^3$ together represent a group $R^{10}C=CR^{11}$ or $R^{10}C=N$.

14. The compound of claim 1, wherein $R^2$, $R^3$, $R^4$ and $R^5$ independently represent hydrogen, methyl, ethyl or trifluoromethyl; $R^6$ and $R^7$ independently represent hydrogen or methyl and $R^{10}$ and $R^{11}$ independently represent hydrogen, methyl, fluoro, bromo, trifluoromethyl or phenyl.

15. The compound of claim 1, which is selected from:
(6-Bromo-pyrazolo[1,5-a]pyrimidin-2-yl)-(4-methyl-6,7-dihydro-4H-thieno[3,2-c]pyridin-5-yl)-methanone,
(6-Chloro-pyrazolo[1,5-a]pyrimidin-2-yl)-(4-methyl-6,7-dihydro-4H-thieno[3,2-c]pyridin-5-yl)-methanone,
(6-Chloro-pyrazolo[1,5-a]pyrimidin-2-yl)-(6,7-dihydro-4H-thieno[3,2-c]pyridin-5-yl)-methanone,
(6-Bromo-pyrazolo[1,5-a]pyrimidin-2-yl)-(6,7-dihydro-4H-thieno[3,2-c]pyridin-5-yl)-methanone,
(6-Chloro-pyrazolo[1,5-a]pyrimidin-2-yl)-(4,4-dimethyl-6,7-dihydro-4H-thieno[3,2-c]pyridin-5-yl)-methanone,
(6-Bromo-pyrazolo[1,5-a]pyrimidin-2-yl)-(4,4-dimethyl-6,7-dihydro-4H-thieno[3,2-c]pyridin-5-yl)-methanone,
(6-Chloro-pyrazolo[1,5-a]pyrimidin-2-yl)-(6-methyl-6,7-dihydro-4H-thieno[3,2-]pyridin-5-yl)-methanone,
(6-Bromo-pyrazolo[1,5-a]pyrimidin-2-yl)-(6-methyl-6,7-dihydro-4H-thieno[3,2-]pyridin-5-yl)-methanone,
(6-Bromo-pyrazolo[1,5-a]pyrimidin-2-yl)-(4-ethyl-6,7-dihydro-4H-thieno[3,2-c]pyridin-5-yl)-methanone,
(6-Chloro-pyrazolo[1,5-a]pyrimidin-2-yl)-(4-ethyl-6,7-dihydro-4H-thieno[3,2-c]pyridin-5-yl)-methanone,
(6-Bromo-pyrazolo[1,5-a]pyrimidin-2-yl)-(4-trifluoromethyl-6,7-dihydro-4H-thieno[3,2-c]pyridin-5-yl)-methanone,
(6-Chloro-pyrazolo[1,5-a]pyrimidin-2-yl)-(4-trifluoromethyl-6,7-dihydro-4H-thieno[3,2-c]pyridin-5-yl)-methanone,
6-Bromo-pyrazolo[1,5-a]pyrimidin-2-yl)-(6,6-dimethyl-6,7-dihydro-4H-thieno[3,2-c]pyridin-5-yl)-methanone,
6-Chloro-pyrazolo[1,5-a]pyrimidin-2-yl)-(6,6-dimethyl-6,7-dihydro-4H-thieno[3,2-c]pyridin-5-yl)-methanone,
(6-Bromo-pyrazolo[1,5-a]pyrimidin-2-yl)-(2,4-dimethyl-6,7-dihydro-4H-thieno[3,2-c]pyridin-5-yl)-methanone,
(6-Chloro-pyrazolo[1,5-a]pyrimidin-2-yl)-(2,4-dimethyl-6,7-dihydro-4H-thieno[3,2-c]pyridin-5-yl)-methanone,
(6-Bromo-pyrazolo[1,5-a]pyrimidin-2-yl)-(3,4-dimethyl-6,7-dihydro-4H-thieno[3,2-c]pyridin-5-yl)-methanone,
(6-Bromo-pyrazolo[1,5-a]pyrimidin-2-yl)-(2,3,4-trimethyl-6,7-dihydro-4H-thieno[3,2-c]pyridin-5-yl)-methanone,
(6-Chloro-pyrazolo[1,5-a]pyrimidin-2-yl)-(2,3,4-trimethyl-6,7-dihydro-4H-thieno[3,2-c]pyridin-5-yl)-methanone,
(6-Bromo-pyrazolo[1,5-a]pyrimidin-2-yl)-(2-fluoro-4-methyl-6,7-dihydro-4H-thieno[3,2-c]pyridin-5-yl)-methanone, (6-Chloro-pyrazolo[1,5-a]pyrimidin-2-yl)-(2-fluoro-4-methyl-6,7-dihydro-4H-thieno[3,2-c]pyridin-5-yl)-methanone,
(6-Bromo-pyrazolo[1,5-a]pyrimidin-2-yl)-(3-fluoro-4-methyl-6,7-dihydro-4H-thieno[3,2-c]pyridin-5-yl)-methanone,
(6-Chloro-pyrazolo[1,5-a]pyrimidin-2-yl)-(3-fluoro-4-methyl-6,7-dihydro-4H-thieno[3,2-c]pyridin-5-yl)-methanone,
(6-Bromo-pyrazolo[1,5-a]pyrimidin-2-yl)-(2,3-difluoro-4-methyl-6,7-dihydro-4H-thieno[3,2-c]pyridin-5-yl)-methanone,
(6-Chloro-pyrazolo[1,5-a]pyrimidin-2-yl)-(2,3-difluoro-4-methyl-6,7-dihydro-4H-thieno[3,2-c]pyridin-5-yl)-methanone,
(6-Bromo-pyrazolo[1,5-a]pyrimidin-2-yl)-(4-methyl-2-trifluoromethyl-6,7-dihydro-4H-thieno[3,2-c]pyridin-5-yl)-methanone,
(6-Chloro-pyrazolo[1,5-a]pyrimidin-2-yl)-(4-methyl-2-trifluoromethyl-6,7-dihydro-4H-thieno[3,2-c]pyridin-5-yl)-methanone,
(6-Bromo-pyrazolo[1,5-a]pyrimidin-2-yl)-(4-methyl-6,7-dihydro-4H-furo[3,2-c]pyridin-5-yl)-methanone,
(6-Chloro-pyrazolo[1,5-a]pyrimidin-2-yl)-(4-methyl-6,7-dihydro-4H-furo[3,2-c]pyridin-5-yl)-methanone,
(6-Chloro-pyrazolo[1,5-a]pyrimidin-2-yl)-(6,7-dihydro-4H-furo[3,2-c]pyridin-5-yl)-methanone,
(6-Bromo-pyrazolo[1,5-a]pyrimidin-2-yl)-(6,7-dihydro-4H-furo[3,2-c]pyridin-5-yl)-methanone,
(6-Bromo-pyrazolo[1,5-a]pyrimidin-2-yl)-(6-methyl-6,7-dihydro-4H-furo[3,2-c]pyridin-5-yl)-methanone,
(6-Chloro-pyrazolo[1,5-a]pyrimidin-2-yl)-(6-methyl-6,7-dihydro-4H-furo[3,2-c]pyridin-5-yl)-methanone,
(6-Chloro-pyrazolo[1,5-a]pyrimidin-2-yl)-(2,4-dimethyl-6,7-dihydro-4H-furo[3,2-c]pyridin-5-yl)-methanone,
(6-Bromo-pyrazolo[1,5-a]pyrimidin-2-yl)-(2,4-dimethyl-6,7-dihydro-4H-furo[3,2-c]pyridin-5-yl)-methanone,
(6-Bromo-pyrazolo[1,5-a]pyrimidin-2-yl)-(1,4,6,7-tetrahydro-pyrrolo[3,2-c]pyridin-5-yl)-methanone,
(6-Chloro-pyrazolo[1,5-a]pyrimidin-2-yl)-(1,4,6,7-tetrahydro-pyrrolo[3,2-c]pyridin-5-yl)-methanone,
(6-Chloro-pyrazolo[1,5-a]pyrimidin-2-yl)-(4-methyl-1,4,6,7-tetrahydro-pyrrolo[3,2-c]pyridin-5-yl)-methanone,
(6-Bromo-pyrazolo[1,5-a]pyrimidin-2-yl)-(4-methyl-1,4,6,7-tetrahydro-pyrrolo[3,2-c]pyridin-5-yl)-methanone,
(6-Bromo-pyrazolo[1,5-a]pyrimidin-2-yl)-(8-methyl-5,8-dihydro-6H-[1,7]naphthyridin-7-yl)-methanone,
(6-Chloro-pyrazolo[1,5-a]pyrimidin-2-yl)-(8-methyl-5,8-dihydro-6H-[1,7]naphthyridin-7-yl)-methanone,
(6-Bromo-pyrazolo[1,5-a]pyrimidin-2-yl)-(1-methyl-3,4-dihydro-1H-[2,7]naphthyridin-2-yl)-methanone,
(6-Chloro-pyrazolo[1,5-a]pyrimidin-2-yl)-(1-methyl-3,4-dihydro-1H-[2,7]naphthyridin-2-yl)-methanone,
(6-Bromo-pyrazolo[1,5-a]pyrimidin-2-yl)-(1-methyl-3,4-dihydro-1H-[2,6]naphthyridin-2-yl)-methanone,
(6-Chloro-pyrazolo[1,5-a]pyrimidin-2-yl)-(1-methyl-3,4-dihydro-1H-[2,6]naphthyridin-2-yl)-methanone,
5-[(6-Bromopyrazolo[1,5-a]pyrimidin-2-yl)carbonyl]-3-phenyl-4,5,6,7-tetrahydro-isoazolo[4,5-c]pyridine,
5-[(6-Bromopyrazolo[1,5-a]pyrimidin-2-yl)carbonyl]-3-phenyl-4,5,6,7-tetrahydroisoxazolo[4,5-c]pyridine,
6-Bromo-2-[(4-methyl-6,7-dihydrothieno[3,2-c]pyridin-5(4H)-yl)carbonyl]pyrazolo[1,5-a]pyrimidine,
(6-Bromo-pyrazolo[1,5-a]pyrimidin-2-yl)-(2,4-dimethyl-6,7-dihydro-4H-thieno[3,2-c]pyridin-5-yl)-methanone,
(6-Bromo-pyrazolo[1,5-a]pyrimidin-2-yl)-(3,4-dimethyl-6,7-dihydro-4H-thieno[3,2-c]pyridin-5-yl)-methanone,
(6-Chloro-pyrazolo[1,5-a]pyrimidin-2-yl)-(2,4-dimethyl-6,7-dihydro-4H-thieno[3,2-c]pyridin-5-yl)-methanone,
(6-Bromo-pyrazolo[1,5-a]pyrimidin-2-yl)-(4-ethyl-6,7-dihydro-4H-thieno[3,2-c]pyridin-5-yl)-methanone,
(6-Chloro-pyrazolo[1,5-a]pyrimidin-2-yl)-(4-ethyl-6,7-dihydro-4H-thieno[3,2-c]pyridin-5-yl)-methanone,
(6-Chloro-pyrazolo[1,5-a]pyrimidin-2-yl)-(4-methyl-6,7-dihydro-4H-thieno[3,2-c]pyridin-5-yl)-methanone,
6-Chloro-2-[(4-methyl-6,7-dihydrofuro[3,2-c]pyridin-5(4H)-yl)carbonyl]pyrazolo[1,5-a]pyrimidine,
6-Chloro-2-[(2,3,4-trimethyl-6,7-dihydrothieno[3,2-c]pyridin-5(4H)-yl)carbonyl]pyrazolo[1,5-a]pyrimidine,
6-Bromo-2-[(4-methyl-6,7-dihydrofuro[3,2-c]pyridin-5(4H)-yl)carbonyl]pyrazolo[1,5-a]pyrimidine,
6-Bromo-2-[(2,3,4-trimethyl-6,7-dihydrothieno[3,2-c]pyridin-5(4H)-yl)carbonyl]pyrazolo[1,5-a]pyrimidine,
(6-Bromo-pyrazolo[1,5-a]pyrimidin-2-yl)-(4-methyl-6,7-dihydro-4H-thieno[3,2-c]pyridin-5-yl)-methanone,
(6-Bromo-pyrazolo[1,5-a]pyrimidin-2-yl)-(4-methyl-6,7-dihydro-4H-thieno[3,2-c]pyridin-5-yl)-methanone,
(6-Bromo-pyrazolo[1,5-a]pyrimidin-2-yl)-(6-methyl-6,7-dihydro-4H-thieno[3,2-c]pyridin-5-yl)-methanone,
(6-Chloro-pyrazolo[1,5-a]pyrimidin-2-yl)-(4-trifluoromethyl-6,7-dihydro-4H-thieno[3,2-c]pyridin-5-yl)-methanone,
(6-Chloro-pyrazolo[1,5-a]pyrimidin-2-yl)-(6-methyl-6,7-dihydro-4H-thieno[3,2-c]pyridin-5-yl)-methanone,
(6-Chloro-pyrazolo[1,5-a]pyrimidin-2-yl)-(2,4-dimethyl-6,7-dihydro-4H-furo[3,2-c]pyridin-5-yl)-methanone,
(6-Bromo-pyrazolo[1,5-a]pyrimidin-2-yl)-(2,4-dimethyl-6,7-dihydro-4H-furo[3,2-c]pyridin-5-yl)-methanone,
(6-Bromo-pyrazolo[1,5-a]pyrimidin-2-yl)-(4-methyl-6,7-dihydro-4H-oxazolo[4,5-c]pyridin-5-yl)-methanone,
(6-Bromo-pyrazolo[1,5-a]pyrimidin-2-yl)-(2-fluoro-4-methyl-6,7-dihydro-4H-oxazolo[4,5-c]pyridin-5-yl)-methanone,
(6-Bromo-pyrazolo[1,5-a]pyrimidin-2-yl)-(2-chloro-4-methyl-6,7-dihydro-4H-oxazolo[4,5-c]pyridin-5-yl)-methanone,
(6-Bromo-pyrazolo[1,5-a]pyrimidin-2-yl)-(2,4-dimethyl-6,7-dihydro-4H-oxazolo[4,5-c]pyridin-5-yl)-methanone,
(6-Bromo-pyrazolo[1,5-a]pyrimidin-2-yl)-(2,4-dimethyl-6,7-dihydro-4H-oxazolo[4,5-c]pyridin-5-yl)-methanone,
(6-Bromo-pyrazolo[1,5-a]pyrimidin-2-yl)-(2-methoxy-4-methyl-6,7-dihydro-4H-oxazolo[4,5-c]pyridin-5-yl)-methanone,
(6-Bromo-pyrazolo[1,5-a]pyrimidin-2-yl)-(1-methyl-1,3,4,5-tetrahydro-[2]pyrindin-2-yl)-methanone,
(6-Bromo-pyrazolo[1,5-a]pyrimidin-2-yl)-(1-methyl-1,3,4,7-tetrahydro-[2]pyrindin-2-yl)-methanone,
(6-Chloro-pyrazolo[1,5-a]pyrimidin-2-yl)-(1-methyl-1,3,4,5-tetrahydro-[2]pyrindin-2-yl)-methanone,
(6-Chloro-pyrazolo[1,5-a]pyrimidin-2-yl)-(1-methyl-1,3,4,7-tetrahydro-[2]pyrindin-2-yl)-methanone,
(6-Bromo-pyrazolo[1,5-a]pyrimidin-2-yl)-(1,5,5-trimethyl-1,3,4,5-tetrahydro-[2]pyrindin-2-yl)-methanone,
(6-Bromo-pyrazolo[1,5-a]pyrimidin-2-yl)-(1,7,7-trimethyl-1,3,4,7-tetrahydro-[2]pyrindin-2-yl)-methanone,
(6-Chloro-pyrazolo[1,5-a]pyrimidin-2-yl)-(1,5,5-trimethyl-1,3,4,5-tetrahydro-[2]pyrindin-2-yl)-methanone,
(6-Chloro-pyrazolo[1,5-a]pyrimidin-2-yl)-(1,7,7-trimethyl-1,3,4,7-tetrahydro-[2]pyrindin-2-yl)-methanone,
(6-Bromo-pyrazolo[1,5-a]pyrimidin-2-yl)-[7-methyl-1-(1H-tetrazol-5-yl)-1,4,5,7-tetrahydro-pyrrolo[2,3-c]pyridin-6-yl]-methanone,
(6-Chloro-pyrazolo[1,5-a]pyrimidin-2-yl)-[7-methyl-1-(1H-tetrazol-5-yl)-1,4,5,7-tetrahydro-pyrrolo[2,3-c]pyridin-6-yl]-methanone, (6-Bromo-pyrazolo[1,5-a]pyrimidin-2-yl)-[4-methyl-1-(1H-tetrazol-5-yl)-1,4,6,7-tetrahydro-pyrrolo[3,2-c]pyridin-5-yl]-methanone, (6-Chloro-pyrazolo[1,5-a]pyrimidin-2-yl)-[4-methyl-1-(1H-tetrazol-5-yl)-1,4,6,7-tetrahydro-pyrrolo[3,2-c]pyridin-5-yl]-methanone, (6-Bromo-pyrazolo[1,5-a]pyrimidin-2-yl)-[4-methyl-1-(1H-tetrazol-5-yl)-2,4,6,7-tetrahydro-pyrrolo[3,4-c]pyridin-5-yl]-methanone, (6-Chloro-pyrazolo[1,5-a]pyrimidin-2-yl)-[4-methyl-1-(1H-tetrazol-5-yl)-2,4,6,7-tetrahydro-pyrrolo[3,4-c]pyridin-5-yl]-methanone, and optical isomers, pharmaceutically-acceptable acid and base addition salts thereof.

16. The compound of claim 1, which is selected from those of formula (IA),

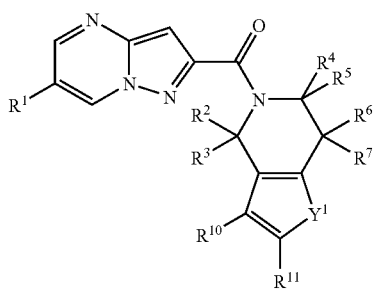

(IA)

wherein $Y^1$ represents NH, S, or O;

$R^1$ represents chloro or bromo;

$R^2$ represents hydrogen, $C_{1-6}$alkyl, or trifluoromethyl;

$R^3$ represents hydrogen, $C_{1-6}$alkyl, or trifluoromethyl;

$R^4$ represents hydrogen, $C_{1-6}$alkyl, or trifluoromethyl;

$R^5$ represents hydrogen, $C_{1-6}$alkyl, or trifluoromethyl;

$R^6$ represents hydrogen, $C_{1-6}$alkyl, or trifluoromethyl;

$R^7$ represents hydrogen, $C_{1-6}$alkyl, or trifluoromethyl and $R^{10}$ and $R^{11}$ independently represent hydrogen, halogen, amino, hydroxy, nitro, cyano, trifluoromethyl, trifluoromethoxy, phenyl, $C_{1-6}$alkyl or $C_{1-6}$alkoxy, and optical isomers and pharmaceutically acceptable salts thereof.

17. The compound of claim 16, wherein $R^2$, $R^3$, $R^4$ and $R^5$ independently represent hydrogen or methyl; $R^6$ and $R^7$ represent hydrogen; and $R^{10}$ and $R^{11}$ independently represent hydrogen, halogen, trifluoromethyl or $C_{1-6}$alkyl.

18. A pharmaceutical composition comprising as active ingredient at least one compound of claim 1, together with one or more pharmaceutically acceptable excipients.

19. A pharmaceutical composition comprising a combination of at at least one compound of claim 1 and at least one N-methyl-D-asparate (NMDA) receptor antagonist, together with one or more pharmaceutically acceptable excipients.

\* \* \* \* \*